US006558935B1

(12) United States Patent
Tang et al.

(10) Patent No.: US 6,558,935 B1
(45) Date of Patent: May 6, 2003

(54) HUMAN TRANSFERASE PROTEINS

(75) Inventors: Y. Tom Tang, San Jose, CA (US); Neil C. Corley, Castro Valley, CA (US); Karl J. Guegler, Menlo Park, CA (US); Mariah R. Baughn, San Leandro, CA (US); Preeti Lal, Santa Clara, CA (US); Henry Yue, Sunnyvale, CA (US); Jennifer L. Hillman, Mountain View, CA (US); Yalda Azimzai, Castro Valley, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/786,240

(22) PCT Filed: Sep. 9, 1999

(86) PCT No.: PCT/US99/20989

§ 371 (c)(1),
(2), (4) Date: Mar. 12, 2002

(87) PCT Pub. No.: WO00/14251

PCT Pub. Date: Mar. 16, 2000

Related U.S. Application Data

(60) Provisional application No. 60/133,642, filed on May 11, 1999, provisional application No. 60/155,248, filed on Nov. 4, 1998, and provisional application No. 60/172,220, filed on Sep. 10, 1998.

(51) Int. Cl.[7] .............................. C12N 9/10; C12N 1/21; C12N 15/00; C07H 21/04

(52) U.S. Cl. ................. 435/193; 435/320.1; 435/252.3; 435/252.33; 435/91.1; 435/325; 536/23.1; 536/23.2; 536/23.5; 530/350

(58) Field of Search ............................... 435/193, 91.1, 435/320.1, 252.3, 252.33, 325; 536/23.1, 23.2, 23.5; 530/350

(56) References Cited

PUBLICATIONS

Jardim et al., The Conserved Serine–Tyrosine Dipeptide in *Leishmania donovani* Hypoxanthine–guanine Phosphoribosyltransferase Is Essential for Catalytic Activity, J. Biol. Chem. vol. 272, No. 14, pp. 8967–8973, Apr. 1997.*

Giang et al., "A Second Mammalian N–Myristoyltransferase" *The Journal of Biological Chemistry* 273:6595–6598 (1998).

Giang et al., (Direct Submission), GenBank Sequence Database Accession GI 3005064, NCBI, Accession No. AF043325, Oct. 2000.

* cited by examiner

*Primary Examiner*—Richard Hutson
(74) *Attorney, Agent, or Firm*—Incyte Genomics, Inc.

(57) ABSTRACT

The invention provides human transferase proteins (TRNSFS) and polynucleotides which identify and encode TRNSFS. The invention also provides expression vectors, host cells, antibodies, agonists, and antagonists. The invention also provide methods for diagnosing, treating, or preventing disorders, associated with expression of TRNSFS.

5 Claims, 6 Drawing Sheets

FIGURE 1A

```
1    MAEDSESAASQQSLEDDQDTCGIDGDNEEETEHA           1632930
1    MMEGNG----------NGHEHCS-DCENEEDNSYN          GI 2443814

36   KG--SPGGYLGAKKKKKKQKRKKEKPNSGGTKSDS          1632930
25   RGGLSPANDTGAKKKKKKQKKKEK---GSETDS            GI 2443814

69   ASDSQEIKIQQPSKNPSVPMQKLQDIQRAMELLSA          1632930
56   AQD-------QPVKMNSLPAERIQEIQKAIELFSV          GI 2443814

104  CQGPARNIDEAAKHRYQFWDTQPVPKLDEVITSHG          1632930
84   GQGPAKTMEEASKRSYQFWDTQPVPKLGEVVNTHG          GI 2443814

139  AIEPDKVNVRQEPYSLPQGFMDTLDLSDAEVLKE           1632930
119  PVEPDKDNIRQEPYTLPQGFTWDALDLGDRGVLKE          GI 2443814

174  LYTLLNENYVEDDDNMFRFDYSPEFLLWALRPPGW          1632930
154  LYTLLNENYVEDDDNMFRFDYSPEFLLWALRPPGW          GI 2443814

209  LLQWHCGVRVSSNKKLVGFISAIPANIRIYDSVKK          1632930
189  LPQWHCGVRVSRKLVGFISAIPANIHIYDTEKK            GI 2443814

244  MVEINFLCVHKKLRSKRVAPVLIREITRRVNLEGI          1632930
224  MVEINFLCVHKKLRSKRVAPVLIREITRRVHLEGI          GI 2443814
```

FIGURE 1A

| | | |
|---|---|---|
| 279 | F Q A V Y T A G V V L P K P I A T C R Y W H R S L N P R K L V E V K F | 1632930 |
| 259 | F Q A V Y T A G V V L P K P V G T C R Y W H R S L N P R K L I E V K F | GI 2443814 |
| 314 | S H L S R N M T L Q R T M K L Y R L P D V T K T S G L R P M E P K D I | 1632930 |
| 294 | S H L S R N M T M Q R T M K L Y R L P E T P K T A G L R P M E T K D I | GI 2443814 |
| 349 | K S V R E L I N T Y L K Q F H L A P V M D E E E V A H W F L P R E H I | 1632930 |
| 329 | P V H Q L L T R Y L K Q F H L T P V M S Q E E V E H W F Y P Q E N I | GI 2443814 |
| 384 | I D T F V V E S P N G K L T D F L S F Y T L P S T V M H H P A H K S L | 1632930 |
| 364 | I D T F V V E N A N G E V T D F L S F Y T L P S T I M N H P T H K S L | GI 2443814 |
| 419 | K A A Y S F Y N I H T E T P L L D L M S D A L I L A K S K G F D V F N | 1632930 |
| 399 | K A A Y S F Y N V H T Q T P L L D L M S D A L V L A K M K G F D V F N | GI 2443814 |
| 454 | A L D L M E N K T F L E K L K F G I G D G N L Q Y Y L Y N W R C P G T | 1632930 |
| 434 | A L D L M E N K T F L E K L K F G I G D G N L Q Y Y L Y N W K C P S M | GI 2443814 |
| 489 | D S E K V G L V L Q | 1632930 |
| 469 | G A E K V G L V L Q | GI 2443814 |

FIGURE 1B

| | | | | | | | | | | | | | | |
|---|---|---|---|---|---|---|---|---|---|---|---|---|---|---|
| 1 | M | - | - | - | - | - | - | - | - | K | A | L | I | L | V | G | G | Y | G | T | 2682663 |
| 1 | M | - | - | - | - | - | - | - | - | K | A | L | I | L | V | G | G | F | G | T | g26422159 |
| 1 | M | V | V | S | P | L | P | S | M | K | A | L | I | L | V | G | G | Y | G | T | g2804432 |
| 13 | R | L | R | P | L | T | L | S | T | P | K | P | L | V | D | F | C | N | K | P | 2682663 |
| 13 | R | L | R | P | L | T | L | S | F | P | K | P | L | V | D | F | A | N | K | P | g26422159 |
| 21 | R | L | R | P | L | T | L | T | Q | P | K | P | L | V | E | F | A | N | K | P | g2804432 |
| 33 | L | L | H | Q | V | E | A | L | A | A | A | G | V | D | H | V | I | L | A | | 2682663 |
| 33 | M | I | L | H | Q | I | E | A | L | K | A | V | G | V | D | E | V | V | L | A | g26422159 |
| 41 | M | M | L | H | Q | M | E | A | L | A | E | V | G | V | D | T | V | L | A | | g2804432 |
| 53 | V | S | Y | M | S | Q | V | L | E | K | E | M | K | A | Q | E | Q | R | L | G | 2682663 |
| 53 | I | N | Y | Q | P | E | V | M | L | N | F | L | K | D | F | E | T | K | L | E | g26422159 |
| 61 | V | S | Y | R | A | E | Q | L | E | Q | E | M | T | V | H | A | D | R | L | G | g2804432 |
| 73 | H | I | R | I | S | M | S | H | E | E | P | L | G | T | A | G | P | L | A | L | 2682663 |
| 73 | H | I | K | I | T | C | S | Q | E | T | E | E | P | L | G | T | A | G | P | L | g26422159 |
| 81 | V | K | L | I | F | S | L | E | E | E | P | L | G | T | A | G | P | L | A | L | g2804432 |
| 93 | A | R | - | D | L | L | S | E | T | A | D | P | F | F | V | L | N | S | D | V | 2682663 |
| 93 | A | R | - | D | K | L | L | D | G | S | G | E | P | F | F | V | L | N | S | D | V | g26422159 |
| 101 | A | R | - | K | H | L | - | E | G | D | A | P | F | F | V | L | N | S | D | V | g2804432 |

HUMAN TRANSFERASE PROTEINS

This application is the national stage entry of PCT/US99/20989, filed Sep. 9, 1999, which claims the benefit of Ser. No. 60/172,220, filed Sep. 10, 1998, U.S. Ser. No. 60/155,248, filed Nov. 4, 1998, and U.S. Ser. No. 60/133,642, filed May 11, 1999.

TECHNICAL FIELD

This invention relates to nucleic acid and amino acid sequences of human transferase proteins and to the use of these sequences in the diagnosis, treatment, and prevention of cancer, developmental disorders, gastrointestinal disorders, genetic disorders, immunological disorders, neurological disorders, reproductive disorders, and smooth muscle disorders.

BACKGROUND OF THE INVENTION

Transferase Proteins

Transferases are enzymes that catalyze the transfer of molecular groups from a donor to an acceptor molecule. The reaction may involve an oxidation, reduction, or cleavage of covalent bonds and is often specific to a substrate or to particular sites on a type of substrate. Transferase proteins participate in reactions essential to such functions as synthesis and degradation of cell components, and regulation of cell functions, including cell signaling, cell proliferation, inflammation, apoptosis, secretion and excretion. Transferases are involved in key steps in disease processes involving these functions. These enzymes are frequently classified according to the type of group transferred. For example, methyl transferases transfer one-carbon methyl groups, amino transferases transfer nitrogenous amino groups, and similarly denominated enzymes transfer aldehyde or ketone, acyl, glycosyl, alkyl or aryl, isoprenyl, saccharyl, phosphorous-containing, sulfur-containing, or selenium-containing groups, as well as small enzymatic groups such as Coenzyme A.

One example of a glycosyl transferase is O-linked N-acetylglucosamine (O-GlcNAc) transferase, an enzyme that catalyzes the reaction of monosaccharide N-acetylglucosamine linking to the hydroxyl group of a serine or threonine residue. O-GlcNAc and N-acetyl-β-D-glucosaminidase (O-GlcNAcase), regulate the attachment and removal, respectively, of O-GlcNAc from proteins in a manner analagous to regulation of protein phosphorylation by kinases and phosphotases. O-GlcNAc transferase has been localized primarily in the nucleus and the cytosol of cells and has been shown to play a role in several cellular systems such as transcription, nuclear transport, and cytoskeletal organization. O-GlcNAc transferase is a heterodimer consisting of two catalytic 110-kDa (p110) subunits and one 78-kDa (p78) subunit. The gene encoding this enzyme is highly conserved. The amino terminus of the p110 subunit has homology to the tetratricopeptide repeat (TPR) motif while the carboxyl terminus has no significant homology (Kreppel, L. K. et al. (1997) J. Biol. Chem. 272:9308–9315). Proteins containing the TPR motif interact through this TPR domain to form regulatory complexes. TPR motifs are believed to play a role in modulation of cellular processes such as cell cycle, transcription, and protein transport (Das, A. K. et al. (1998) EMBO J 17:1192–1199).

The enzyme hypoxanthine-guanine phosphoribosyltransferase (HGPRT) is a purine salvage enzyme that catalyzes the conversion of hypoxanthine and guanine to their respective mononucleotides. HGPRT is ubiquitous, is known as a 'housekeeping' gene, and is frequently used as an internal control for reverse transcriptase polymerase chain reactions. There is a serine-tyrosine dipeptide that is conserved among all members of the HGPRT family and is essential for the phosphoribosylation of purine bases(Jardim, A. and Ullman, B. (1997) J. Biol. Chem. 272:8967–8973). A partial deficiency of HGPRT can lead to overproduction of uric acid, causing a severe form of gout. An absence of HGPRT causes Lesch-Nyhan syndrome, characterized by hyperuricaemia, mental retardation, choreoathetosis, and compulsive self-mutilation (Sculley, D. G. et al. (1992) Hum Genet 90:195–207).

Polyprenyl transferases catalyze the addition of polyprenyl groups to molecules. For example, the enzyme 1,4-dihydroxy-2-napthoate octaprenyltransferase catalyzes the conversion of the soluble 1,4-dihydroxy-2-napthoic acid (DHNA) to the membrane-bound demethylmenaquinone by attaching a 40-C side chain to DHNA, a key step in the biosynthesis of menaquinone (vitamin K2). This octaprenyltransferase is a membrane protein in *Escherichia coli* that is necessary for the synthesis of menaquinone (Suvarna, K. et al. (1998) J. Bacteriol. 180:2782–2787). Quinones, in many cases, take part in the oxidation-reduction cycles essential to living organisms (Morrison, R. T. and Boyd, R. N. (1987) *Organic Chemistry*, Allyn and Bacon, Inc., Newton, Mass., pp. 1092–1093). Other octaprenyltransferase have been shown to allow the synthesis of quinones under anaerobic conditions and, therefore, may play a role in anaerobic metabolism (Alexander, K. and Young, I. G. (1978) Biochemistry 17:4750–4755).

The synthesis of 3'-phosphoadenosine-5'-phosphosulfate (PAPS) requires two enzymes, adenosine triphosphate (ATP) sulfurylase and adenosine 5'-phosphosulfate (APS) kinase. ATP sulfurylase catalyzes the formation of APS from ATP and free sulfate. APS kinase phosphorylates APS to produce PAPS, the sole source of donor sulfate in higher organisms. In bacteria, fungi, yeast, and plants, these two enzymes are separate polypeptides. In animals, ATP sulfurylase and APS kinase are present in a single protein. The bifunctional enzyme found in mammals shows extensive homology to known sequences of both ATP sulfurylases and APS kinases. APS kinase peptide sequences are well conserved and contain an ATP-GTP binding motif (P-loop) flanked by cysteine residues and a PAPS-dependent enzyme motif. ATP sulfurylase peptide sequences have a PP-motif found in ATP sulfurylases and PAPS reductases (Rosenthal, E. and Leustek, T. (1995) Gene 165:243–248; Li, H. et al. (1995) J. Biol. Chem. 270:29453–29459; Deyrup, A. T. et al. (1998) J. Biol. Chem. 273:9450–9456; Bork, P. and Koonin, E. V. (1994) Proteins 20:347–355).

The enzyme phosphatidylethanolamine N-methyltransferase (PEMT) catalyzes the methylation of phosphatidylethanolamine. Hepatocytes in the liver synthesize phosphatidylcholine (PC) by stepwise methylation of phosphatidylethanolamine and have abundant activity for PEMT. Other cells and tissues express minimal activities for PEMT. All mammalian cells, including hepatocytes, synthesize PC from choline via the CDP-choline pathway. Evidence suggests that one function of hepatic PEMT is to maintain PC synthesis and generate choline when dietary supply of choline is insufficient, as occurs during pregnancy, lactation, or starvation (Walkey, C. J. et al. (1998) J. Biol. Chem. 273:27043–27046). Forms of PEMT may also play a role in hepatocyte proliferation and liver cancer (Walkey, C. J. et al. (1999) Biochim. Biophys. Acta 1436:405–412). In the brain, decreased PEMT activity has been associated with Alzheimer's disease (Guan, Z. Z. et al. (1999) Neurochem. Int. 34:41–47).

Sulfotransferase enzymes catalyze the transfer of sulfur-containing groups to molecules. For example, HNK-1 sulfotransferase (HNK-1ST) forms the HNK-1 carbohydrate epitope by adding a sulfate group to glycoproteins and glycolipids. The HNK-1 epitope was discovered by an antibody against human natural killer cells and is found in neural adhesion molecules, including N-CAM and myelin-associate glycoprotein. The HNK-1 carbohydrate epitope was recognized to have functional significance as an autoantigen involved in peripheral demyelinative neuropathy. The HNK-1ST is a type II membrane protein with a consensus sequence shared by Golgi-associated sulfotransferases. The human and rat HNK-1STs share 90% homology in amino acid sequence. Human HNK-1ST was predominantly detected in fetal brain and in adult brain, testis, and ovary. (See Ong, E. et al. (1998) J. Biol. Chem. 273:5190–5195.)

Camnitine palmitoyitransferase I (CPT I) is an enzyme that catalyzes the transfer of fatty acyl groups from coenzyme A to carnitine, the rate-determining step in mitochondrial fatty acid β-oxidation (a major source of energy production in the cell). CPT I has two structural genes (α and β) that are differentially expressed in tissues that utilize fatty, acids as fuel. The α structure is expressed most highly in the liver, pancreatic β cells, and heart. The β structural gene of CPT I is predominately expressed in skeletal muscle, adipose tissue, heart, and testis (Yu, G. S. et al. (1998) J. Biol. Chem. 273:32901–32909). CPT I deficiency is a life-threatening disorder that appears to be treatable with medium-chain triglycerides. The disorder first presents, between 8 and 18 months, with Reye syndrome-like episodes associated with fasting due to viral infection or diarrhea. Coma, seizures, hepatomegaly, and hypoketotic hypoglycemia characterize these episodes. Persistent neurological defects are common (Online Mendelian Inheritance in Man entry #255120; ExPASy Enzyme:EC 2.3.1.21).

The enzyme glycine N-methyltransferase catalyzes the transfer of the methyl group from S-adenosyimethionine to glycine to form S-adenosylhomocteine and sarcosine. Glycine N-methyltransferase is a tetramer of identical subunits, has a nucloetide binding region, and is localized in the liver. Amino acid sequence homology is found between glycine N-methlytransferases from rat, rabbit, pig, and human livers. Glycine N-methyltransferase can exist as a dimer which binds polycyclic aromatic hydrocarbons (PAHs) and acts as a transcriptional activator (Ogawa, H. et al. (1998) Int. J. Biochem. Cell Biol. 30:13–26; Bhat, R. and Bresnick, E. (1997) J. Biol. Chem. 272:21221–21226).

Myristoyl CoA:protein N-myristoyl-transferase

N-acylation with the 14-carbon fatty acid, myristate is found on the amino groups of N-terminal glycines of a number of proteins that are essential to normal cell functioning and/or are potential therapeutic targets of disease. Examples of such proteins include subunits of heterotrimeric G proteins, GTP-binding arfl, human immunodeficiency virus gag and nef proteins, myristolated alanine-rich C kinase substrate (MARCKS), the protein phosphatase calcineurin B, the pp60$^{src}$ protein tyrosine kinase, the retinal calcium-binding recoverin, the caveolae-associated endothelial nitric oxide synthase, the catalytic subunit of cAMP-dependent protein kinase, and mitochondria-associated cytochrome b5 reductase. (Glover, C. J. et al. (1997) J. Biol. Chem. 272:28680–28689.) N-myristoylated proteins ate associated with a variety of organelles with the myristate moiety required for such diverse functions as specific protein-protein or protein-lipid interactions, ligand-induced protein conformnational changes, and correct subcellular targeting.

Protein myristoylation occurs almost exclusively cotranslationally during protein synthesis of the first 100 amino acids. The reaction is catalyzed by the enzyme myristoyl CoA:protein N-myristoyl-transferase (NMT) 1 (EC 2.3.1.97). (Towler, D. A. et al. (1987) Proc. Natl. Acad. Sci. 84:2708–2712.) Immunofluorescence microscopy reveals NMT to be distributed uniformly throughout the cytoplasm of yeast and mammalian cells. This finding, plus evidence that N-myristoylation occurs on nascent polypeptides bound to free polyribosomes, establish that NMT is physically localized and functionally active in the cell cytoplasm. (Wilcox, C. et al. (1987) Science 238:1275–1278.)

Protein N-myristoylation appears to be a tightly regulated process involving i) the coordinated participation of several different enzvmes/proteins, e.g. N-methionylaminopeptidase, fatty acid synthetase, long chain acyl-CoA synthetase, acyl-CoA-binding proteins; ii) access of NMT to pools of myristoyl-CoA substrate; and iii) N-myristoyiation of nascent polypeptide substrates during protein synthesis to avoid potential interfering reactions such as N-acetylation and polypeptide folding. The ability of NMT to function in regulated N-myristoylation has implied the existence of mechanisms designed to ensure targeting of NMT to the appropriate protein synthesis machinery. These mechanisms may involve interactions with other cooperating components that facilitate the recognition and efficient N-myristoylation of the rapidly growing polypeptide substrates. (Glover, et al. supra.) Protein N-myristoylation activity may be a chemotherapeutic target for cancer, infectious diseases, and immune disorders. Antagonists of NMT may reduce posttranslational myristoylation of oncoproteins and other growth-activating cellular proteins. (Felsted, R. L. et al., (1995) J. Natl. Cancer Inst. 87:1571–1573; Furuishi, K. et al., (1997) Biochem. Biophys. Res. Comm. 237:504–511.)

Mannose-1-phosphate guanvitransferase

Many secretory proteins and membrane proteins are glycosylated proteins that have covalently attached carbohydrate chains, or oligosaccharides. Some of these glycoproteins have only one or a few carbohydrate groups while others have numerous oligosaccharide side chains, which may be linear or branched. The sugar residues of many plasma membrane glycoproteins orient these proteins in membranes. Sugar residues of glycoproteins are hydrophilic and strongly prefer to be located near the aqueous or extracellular surface rather than the hydrocarbon core of the plasma membrane. Because there is a high energy barrier to the rotation of a glycoprotein from one side of the membrane to the other, the carbohydrate groups of membrane glycoproteins help to maintain the asymmetric character of biological membranes. One of the best-characterized glycoproteins is glycophorin, a protein found in the membrane of red blood cells. Many soluble glycoproteins are known as well, including carrier proteins, antibodies, and many of the proteins contained in lysosomes. Carbohydrate groups of plasma membrane glycoproteins play a major role in cell-cell recognition. Oligosaccharides are involved in many inflammatory processes and may also provide targets for tumor immunotherapy.

Glycoproteins are often linked to their oligosaccharides through asparagine (N) residues. These N-linked oligosaccharides are very diverse, but the many pathways by which they all form have a common first step. A 14 residue core oligosaccharide, containing two N-acetylglucosamine, nine mannose, and three glucose residues, is transferred from a dolichol phosphate donor molecule to certain N residues on the proteins (reviewed in Lehninger, A. L. et al. (1993)

*Principles of Biochemistry*, Worth Publishers, New York, N.Y., pp. 931). Glycosylation is the most extensive of all post-translational modifications in proteins and is essential for the secretion, antigenicity, and clearance of glycoproteins.

A variety of enzymes which are involved in sugar metabolism participate directly or iridirectly in glycosylation, such as certain pyrophosphorylases. ADP-glucose pyrophosphorylases play an important role in the biosynthesis of alpha 1,4-glucans (glycogen or starch) in bacteria and plants. Specifically, ADP-glucose pyrophosphorylases catalyze the synthesis of the activated glucosyl donor, ADP-glucose, from glucose-1-phosphate and ATP. ADP-glucose pyrophosphorylases are tetrameric, allosterically regulated enzymes. There are a number of conserved regions in the sequence of bacterial and plant ADP-glucose pyrophosphorylase subunits. Additionally, there are three regions which are considered signature patterns (ExPASy PROSITE database, documents PS00808-PS00810). The first two regions are N-terminal and have been proposed to be part of the allosteric and substrate-binding sites in the *Escherichia coli* enzyme. The third pattern corresponds to a conserved region in the central part of the enzymes.

In eukaryotic cells, mannose-1-phosphate guanyltransferase is involved in eariy steps of protein glycosylation. This enzyme participates in mannose metabolism, and its enzymatic products are channeled into glycdprotein synthesis. Mannose-1-phosphate guanyltransferase (MPG), also referred to as NDP-hexose pyrophosphorylase or GDP-mannose pyrophosphorylase B, catalyzes the conversion of GTP and α-D-mannose 1-phosphate into diphosphate and CDP-ethanolamine. This enzyme is very similar to CDP-glucose pyrophosphorylase and may be involved in the regulation of cell cycle progression. A cDNA coding for MPG 1 was recently isolated from a *Trichoderma reesei* cDNA library (Kruszewska, J. S. et al. (1998) Curr. Genet. 33:445–500). The nucleotide sequence of the 1.6 kb cDNA revealed an ORF which encodes a protein of 364 amino acids. Sequence comparisons demonstrate that this protein shares 70% identity with the yeast *Saccharomvces cerevisiae* MPG 1 gene and 75% identity with the *Schizosaccharomvces pombe* gene. MPGs are conserved among diverse organisms. For example, recent genome sequencing projects have identified MPG homologs in the plant *Arabidousis thaliana* and thenematode *Caenorhabditis elerans* (SEQ ID NO:32 and SEQ ID NO:33, respectively).

Alterations in glycosylation are known to occur in a number of disorders and diseases such as carbohydrate-deficient glycoprotein syndromes (CDGSs). In the biochemical pathway upstream of MPG is an important enzyme called phosphomannomutase (PMM) which provides the mannose 1-phosphate required for the reaction catalyzed by MPG. PMM catalyzes the conversion of D-mannose 6-phosphate to D-mannose 1-phosphate and has been implicated in CDGSs. CDGSs are a group of hereditary multisystem disorders (Matthijs, G. et al. (1 997) Nat. Genet. 16:88–92). The clinical phenotype of most CDGSs is dominated by severe psychomotor and mental retardation, as well as blood coagulation abnormalities as seen in thrombosis, bleeding, or stroke-like episodes. The characteristic biochemical abnormality of CDGSs is the hypoglycosylation of glycoproteins. Depending on the type of CDGS, the carbohydrate side chains of glycoproteins are either truncated or completely missing from the protein core.

A new type of CDGS, designated as CDGS type 1B, has recently been described (Niehues, R. et al. (1998) Clin. Invest. 101:1414–1420). The clinical phenotype of this new disorder is fundamentally different from other types of CDGS in that no psychomotor or mental retardation is present. Instead, CDGS type 1B is a gastrointestinal disorder characterized by protein-losing enteropathy. Some patients who are affected with CDGS type 1B suffer from thrombosis and life-threatening bleeding. A deficiency of phosphomannose isomerase was identified as the most likely cause of this syndrome, and a therapy was developed in the form of oral administration of mannose (Niehues, supra). Mannose treatment can correct the clinical phenotype in CDGS type 1B. It is noteworthy that CDGS is the first inherited disorder in human metabolism that shows a decrease in available mannose. The above findings indicate that increasing blood mannose levels might correct some protein giycosylation deficiencies.

The discovery of new human transferase proteins and the polynucleotides encoding them satisfies a need in the art by providing new compositions which are useful in the diagnosis, prevention, and treatment of cancer, developmental disorders, gastrointestinal disorders, genetic disorders, immunological disorders, neurological disorders, reproductive disorders, and smooth muscle disorders.

SUMMARY OF THE INVENTION

The invention features substantially purified polypeptides, human transferase proteins, referred to collectively as "TRNSFS" and individually as "TRNSFS-1," "TRNSFS-2," "TRNSFS-3," "TRNSFS-4," "TRNSFS-5," "TRNSFS-6," "TRNSFS-7," "TRNSFS-8," "TRNSFS-9," "TRNSFS-10," "TRNSFS-11," "TRNSFS-12," "TRNSFS-13," "TRNSFS-14," and "TRNSFS-15." In one aspect, the invention provides a substantially purified polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 (SEQ ID NO:1–15), and fragments thereof.

The invention further provides a substantially purified variant having at least 90% amino acid identity to at least one of the amino acid sequences selected from the group consisting of SEQ ID NO:1–15 and fragments thereof. The invention also provides an isolated and purified polynucleotide encoding the polypeptide comprising an amino acid sequence selected from the group consisting of SEQ ID NO:1–1 5 and fragments thereof. The invention also includes an isolated and purified polynuclebtide variant having at least 90% polynucleotide sequence identity to the polynucleotide encoding the polypeptide comprising an amino acid sequence selected from the group consisting of SEQ ID NO:1–15 and fragments thereof.

Additionally, the invention provides an isolated and purified polynucleotide which hybridizes under stringent conditions to the polynucleotide encoding the polypepptide comprising an amino acid sequence selected from the group consisting of SEQ ID NO:1–15 and fragments thereof. The invention also provides an isolated and purified polynucleotide having a sequence which is complementary to the polynucleotide encoding the polypeptide comprising the amino acid sequence selected from the group consisting of SEQ ID NO:1–15 and fragments thereof.

The invention also provides a method for detecting a polynucleotide in a sample containing nucleic acids, the method comprising the steps of (a) hybridizing the complement of the poiynucieotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention also provides an isolated and purified polynucleotide comprising a polynucleotide sequence selected from the group consisting of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30 (SEQ ID NO:16–30), and fragments thereof. The invention further provides an isolated and purified polynucleotide variant having at least 90% polynucleotide sequence identity to the polynucieotide sequence selected from the group consisting of SEQ ID NO:16–30 and fragments thereof. The invention also provides an isolated and purified polynucleotide having a sequence which is complementary to the polynucleotide comprising a polynucleotide sequence selected from the group consisting of SEQ ID NO:16–30 and fragments thereof.

The invention further provides an expression vector containing at least a fragment of the polynucleotide encoding the polypeptide comprising an amino acid sequence selected from the group consisting of SEQ ID NO:1–15 and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1–15 and fragments thereof, in conjunction with a suitable pharmaceutical carrier.

The invention further includes a purified antibody which binds to a polypeptide selected from the group consisting of SEQ ID NO:1–15 and fragments thereof. The invention also provides a purified agonist and a purified antagonist to the polypeptide.

The invention also provides a method for treating or preventing a disorder associated with decreased expression or activity of TRNSFS, the method comprising administering to a subject in need of such treatment an effective amount of a pharmaceutical composition comprising a substantially purified polypeptide having the amino acid sequence selected from the group consisting of SEQ ID NO:1–15 and fragments thereof, in conjunction with a suitable pharmaceutical carrier.

The invention also provides a method for treating or preventing a disorder associated with increased expression or activity of TRNSFS, the method comprising administering to a subject in need of such treatment an effective amount of an antagonist of a polypeptide having an amino acid sequence selected from the group consisting of SEQ ID NO:1–15 and fragments thereof.

BRIEF DESCRIPTION OF THE FIGURES AND

FIGS. 1A and 1B show the amino acid sequence alignment between TRNSFS-1 (1632930; SEQ ID NO:1 and human myristoyl CoA:protein N-myristoyltransferase (GI 2443814; SEQ ID NO:31), produced using the multisequence alignment program of LASERGENE software (DNASTAR, Madison Wis.).

Figure 2B:
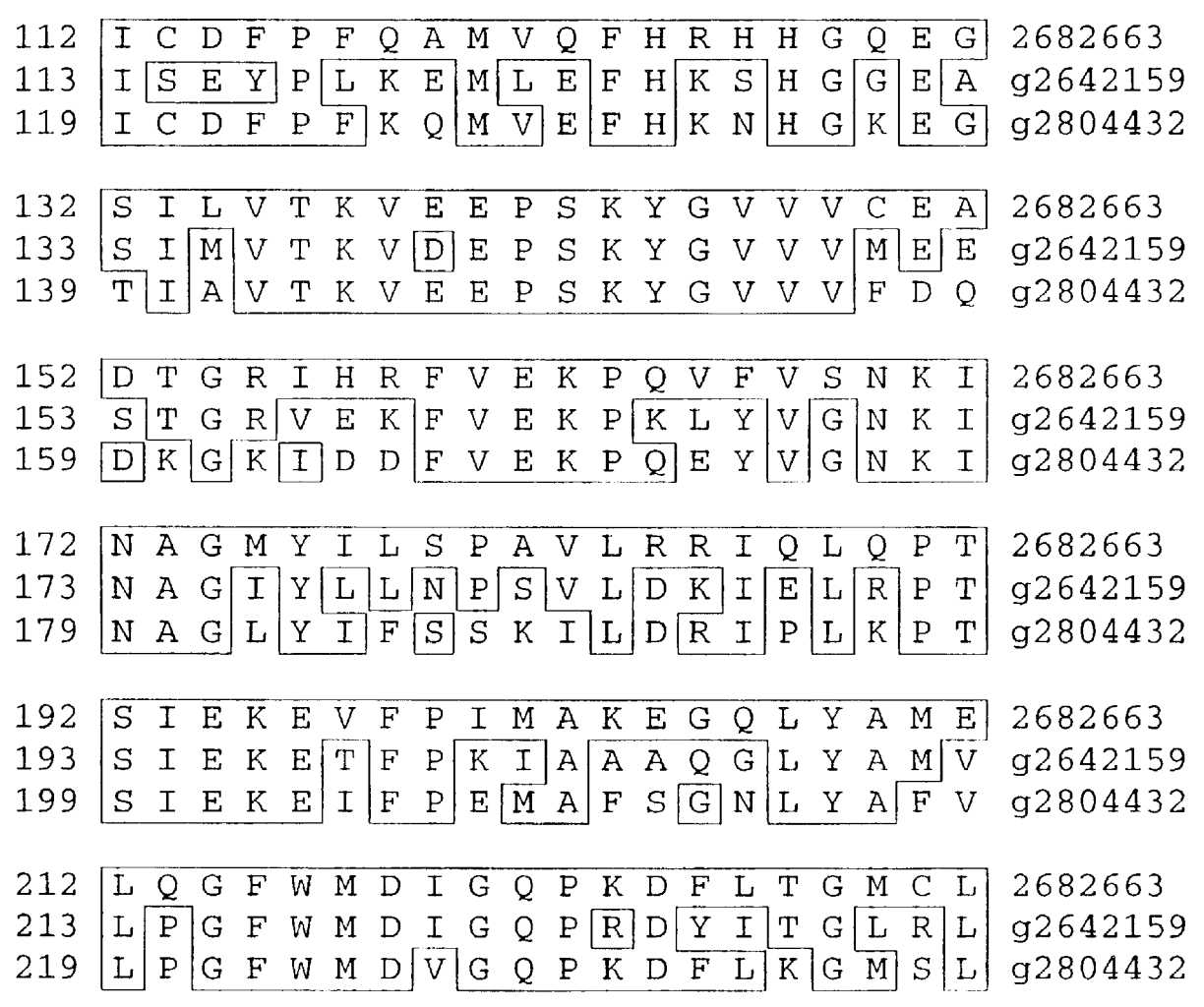

FIGS. 2A, 2B, 2C and 2D show the amino acid sequence alignments among TRNSFS-2 (2682663; SEQ ID NO:2), Arabidopsis thaliana MPG (GI 2642159; SEQ ID NO:32), and *Caenorhabditis elegans* MPG (GI 2804432; SEQ ID NO:33), produced using the multisequence alignment program of LASERGENE software (DNASTAR Inc, Madison Wis.).

Table 1 shows polypeptide and nucleotide sequence identification numbers (SEQ ID NO), clone identification numbers (clone IDs), cDNA libraries, and cDNA fragments used to assemble full-length sequences encoding TRNSFS.

Table 2 shows features of each polypeptide sequence, including potential motifs, homologous sequences, and methods and algorithms used for identification of TRNSFS.

Table 3 shows useful fragments of each nucleic acid sequence; the tissue-specific expression patterns of each nucleic acid sequence as determined by northern analysis; diseases, disorders, or conditions associated with these tissues; and the vector into which each cDNA was cloned.

Table 4 describes the tissues used to construct the cDNA libraries from which cDNA clones encoding TRNSFS were isolated.

Table 5 shows the tools, programs, and algorithms used to analyze TRNSFS, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"TRNSFS" refers to the amino acid sequences of substantially purified TRNSFS obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to TRNSFS, increases or prolongs the duration of the effect of TRNSFS. Agonists may include proteins, nucleic acids, carbohydrates, or any other molecules which bind to and modulate the effect of TRNSFS.

An "allelic variant" is an alternative form of the gene encoding TRNSFS. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding TRNSFS include those sequences with deletions, insertions, or substitutions of different nucleotides, resulting in a polynucleotide the same as TRNSFS or apolypeptide with at least one functional characteristic of TRNSFS. Included within this definition are polymorphisms which may or may not be readily detectable using a particular oligonucleotide probe of the polynucleotide encoding TRNSFS, and improper or unexpected hybridization to alleiic variants, with a locus other than the normal locus for the polynucleotide sequence encoding TRNSFS. The encoded protein may also be "altered," and may contain deletions, insertions, or substitutions of amino acid residues which produce a silent change and result in a functionally equivalent TRNSFS. Deliberate amino acid substitutions may be made on the basis of similarity in polarity, charge, solubility, hydrophobicity, hydrophilicity, and/or the amphipathic nature of the residues, as long as the biological or immunological activity of TRNSFS is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of TRNSFS which are preferably at least 5 to about 15 amino acids in length, most preferably at least 14 amino acids, and which retain some biological activity or immunological activity of TRNSFS. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to TRNSFS, decreases the amount or the duration of the effect of the biological or immunological activity of TRNSFS. Antagonists may include proteins, nucleic acids, carbohydrates, antibodies, or any other molecules which decrease the effect of TRNSFS.

The term "antibody" refers to intact molecules as well as to fragments thereof, such as Fab. $F(ab')_2$, and Fv fragments, which are capable of binding the epitopic determinant. Antibodies that bind TRNSFS polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or,translation. The designation "negative" can refer to the antisense strand, and the designation "positive" can refer to the sense strand.

The term "biologically active" refers to a protein having structural, regulatory, or biochemical functions of a naturally occurring molecule. Likewise, "immunologically active" refers to the capability of the natural, recombinant, or synthetic TRNSFS, or of any oligopeptide thereof, to induce a specific immune response in appropriate animals or cells and to bind with specific antibodies.

The terms "complementary" and "complementarity" refer to the natural binding of polynucleotides by base pairing. For example, the sequence "5' A-G-T 3'" bonds to the complementary sequence "3'T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" and a "composition comprising a given amino acid sequence" refer broadly to any composition containing the given polynucteotide or amino acid sequence. The composition may comprise a dry formulation or an aqueous solution. Compositions comprising polynucleotide sequences encoding TRNSFS or fragments of TRNSFS may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution. dry milk, salmon spern DNA, etc.).

"Consensus sequence" refers to a nucleic acid sequence which has been resequenced to resolve uncalled bases, extended, using the XL-PCR kit (Perkin-Elmer. Norwalk Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding TRNSFS, by northern analysis is indicative of the presence of nucleic acids encoding TRNSFS in a sample, and thereby correlates with expression of the transcript from the polynucleotide encoding TRNSFS.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarilty. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial decree of complementarity (e.g., less than about 30% similarity or identity). In the absence of non-specific binding, the substantially similar sequence or probe will not hybridize to the second non-complementary target sequence.

The phrases "percent identity" and "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237–244.) Parameters for each method may be the default parameters provided by MEGALIGN or may be specified by the user. The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" and "array element" in a microarray context, refer to hybridizable polynucleotides arranged on the surface of a substrate.

The term "modulate" refers to a change in the activity of TRNSFS. For example, modulation may cause an increase or a decrease in protein activity, binding characteristics, or any other biological, functional, or immunological properties of TRNSFS.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense' strand, to peptide nucleic acid (FNA), or to any DNA-like or RNA-like material. In this context, "fragments" refers to those nucleic acid sequences which comprise a region of unique polynucleotide sequence that specifically identifies SEQ ID NO:16–30, for example, as distinct from any other sequence in the same genome. For example, a fragment of SEQ ID NO:16–30 is useful in hybridization and amplification. technologies and in analogous methods that distinguish SEQ ID NO:16–30 from related polynucleotide sequences. A fragment of SEQ ID NO:16–30 is at least about 15–20 nucleotides in length. The precise length of the fragment of SEQ ID NO:16–30 and the region of SEQ ID NO:16–30 to which the fragment corresponds are routinely determinable by one of ordinary skill in the art based on the intended purpose for the fragment. In some cases, a fragment, when translated, would produce polypeptides retaining some functional characteristic, e.g., antigenicity, or structural domain characteristic, e.g., ATP-binding site, of the full-length polypeptide.

The terms "operably associated" and "operably linked" refer to functionally related nucleic acid sequences. A promoter is operably associated or operably linked with a coding sequence if the promoter controls the translation of the encoded poiypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation and may be pegylated to extend their lifespan in the cell.

The term "sample" is used in its broadest sense. A sample suspected of containing nucleic acids encoding TRNSFS, or fragments thereof, or TRNSFS itself, may comprise a bodily fluid; an extract from a cell, chromosome, organelle, or membrane isolated from a cell; a cell; genomic DNA. RNA, or cDNA, in solution or bound to a substrate; a tissue; a tissue print; etc.

The terms "specific binding" and "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of TRNSFS polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to TRNSFS. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding plypeptide may possess additional functional domains or an absence of domains. Species variants are polynucieotide sequences that vary from one species to another. The resulting polypeptides generally will have significant amino acid identity relative to each other. A polymorphic variant is a variation in the poiynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new human human transferase proteins (TRNSFS), the polynucleotides encoding TRNSFS, and the use of these compositions for the diagnosis, treatment, or prevention of cancer, developmental disorders, gastrointestinal disorders, genetic disorders, immunological disorders, neurological disorders, reproductive disorders, and smooth muscle disorders.

Table 1 lists the Incyte clones used to assemble full length nucleotide sequences encoding TRNSFS. Columns 1 and 2 show the sequence identification numbers (SEQ ID NOs) of the polypeptide and nucleotide sequences, respectively. Column 3 shows the clone IDs of the Incyte clones in which nucleic acids encoding each TRNSFS were identified, and column 4 shows the cDNA libraries from which these clones were isolated. Column 5 shows lncyte clones and their corresponding cDNA libraries. Clones for which cDNA libraries are not indicated were derived from pooled cDNA libraries. The clones in column 5 were used to assemble the consensus nucleoide sequence of each TRNSFS and are useful as fragments in hybridization technologies.

The columns of Table 2 show various properties of each of the polypeptides of the invention: column 1 references the SEQ ID NO; column 2 shows the number of amino acid residues, in each polypeptide: column 3 shows potential phosphorylation sites; column 4 shows potential glycosylation sites; column 5 shows the amino acid residues comprising signature sequences and motifs; column 6 shows homologous sequences as identified by BLAST analysis; and column 7 shows analytical methods used to characterize each polypeptide through sequence homology and protein motifs. As shown in FIGS. 1A and 1B, SEQ ID NO:1 has chemical and structural similarity with human myristoyl CoA:protein N-myristoyltransferase (GI 2443814; SEQ ID NO:31). In particular, SEQ ID NO:1 and human myristoyl CoA:protein N-myristoyltransferase share 74% identity, share two potential N-glycosylation sites, three potential casein kinase II phosphorylation sites, seven potential protein kinase C phosphorylation sites, the myristoyl CoA:protein N-myristoyltransferase signatures, and have similar isoelectric points, 7.7 and 8.2, respectively. SEQ ID NO:2 also has one potential bacterial hexapeptide-transferase signature from residue $V_{256}$ to $V_{284}$. This signature is conserved among a number of bacterial transferases which are believed to belong to a single family and are involved in the biosynthesis of glycolipids, polysaccharides, and other macromolecules. As shown in FIGS. 2A, 2B, 2C and 2D. SEQ ID NO:2 has chemical and structural similarity with *Arabidopsis thaliana* MPG (GI 2642159; SEQ ID NO:32), and *Caenorhabditis elegans* MPG (GI 2804432; SEQ ID NO:33). In particular, SEQ ID NO:2 and *Arabidonsis thaliana* MPG share 61% identity, and MPGh and *Caenorhabditis elegans* MPG share 63% identity. Note that the ADP-glucose pyrophosphorylase signature of MPGh is also conserved within both, *Arabidonsis thaliana* and *Caenorhabditis elegans* MPGs. In addition, the potential N-glycosylation site at residue $N_{322}$, the potential casein kinase II phosphorylation sites at residues $S_{78}$, $T_{136}$ and $T_{191}$, the potential tyrosine kinase phosphorylation site at residue $Y_{144}$, and the potential bacterial hexapeptidetransferase signature of SEQ ID NO:2 are conserved in both *Arabidonsis thaliana* and *Caenorhabditis elegans* MPGs.

The columns of Table 3 show the tissue-specificity and diseases, disorders, or conditions associated with nucleotide sequences encoding TRNSFS. The first column of Table 3 lists the nucleotide SEQ ID NOs. Column 2 lists fragments of the nucleotide sequences of column 1. These fragments are useful, for example, in hybridization or amplification technologies to identify SEQ ID NO:16–30 and to distinguish between SEQ ID NO:16–30 and related polynucleotide sequences. The polypeptides encoded by these fragments are useful, for example, as immunogenic peptides. Column 3 lists tissue categories which express TRNSFS as a fraction of total tissues expressing TRNSFS. Column 4 lists diseases, disorders, or conditions associated with those tissues expressing TRNSFS as a fraction of total tissues expressing TRNSFS. Column 5 lists the vectors used to subclone each cDNA library. Of particular note is the expression of SEQ ID NO:1 in reproductive, smooth muscle, and nervous tissue. Of particular note is the expression of SEQ ID NO:2 in reproductive and gastrointestinal tissue.

The columns of Table 4 show descriptions of the tissues used to construct the cDNA libraries from which cDNA clones encoding TRNSFS were isolated. Column 1 references the nucleotide SEQ ID NOs, column 2 shows the cDNA libraries from which these clones were isolated, and column 3 shows the tissue origins and other descriptive information relevant to the cDNA libraries in column 2.

The invention also encompasses TRNSFS variants. A preferred TRNSFS variant is one which has at least about 80%, more preferably at least about 90%, and most preferably at least about 95% amino acid sequence identity to the TRNSFS amino acid sequence, and which contains at least one functional or structural characteristic of TRNSFS.

The invention also encompasses polynucleotides which encode TRNSFS. In a particular embodiment, the invention encompasses a polynucleotide sequence comprising a sequence selected from the group consisting of SEQ ID NO:16–30, which encodes TRNSFS.

The invention also encompasses a variant of a polynucleotide sequence encoding TRNSFS. In particular, such a variant polynucleotide sequence will have at least about 80%, more preferably at least about 90%, and most preferably at least about 95% polynucleotide sequence identity to the polynucleotide sequence encoding TRNSFS. A particular aspect of the invention encompasses a variant of a polynucleotide sequence comprising a sequence selected from the group consisting of SEQ ID NO:16–30 which has at least about 80%, more preferably at least about 90%, and most preferably at least about 95% polynucleotide sequence identity to a nucleic acid sequence selected from the group consisting of SEQ ID NO:16–30. Any one of the polynucleotide variants described above can encode an amino acid sequence which contains at least one functional or structural characteristic of TRNSFS.

It will be appreciated by those skilled in the art that as a result of the degeneracy of the genetic code, a multitude of polynucleotide sequences encoding TRNSFS, some bearing minimal similarity to the polynucleotide sequences of any known and naturally occurring gene, may be produced. Thus, the invention contemplates each and every possible variation of polynucleotide sequence that could be made by selecting combinations based on possible codon choices.

These combinations are made in accordance with the standard triplet genetic code as applied to the polynucleotide sequence of naturally occurring TRNSFS, and all such variations are to be considered as being specifically disclosed.

Although nucleotide sequences which encode TRNSFS and its variants are preferably capable of hybridizing to the nucleotide sequence of the naturally occurring TRNSFS under appropriately selected conditions of stringency, it may be advantageous to produce nucleotide sequences encoding TRNSFS or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding TRNSFS and its derivatives without altering the encoded amino acid sequences include the production of RNA transcripts having more desirable properties, such as a greater half-life, than transcripts produced from the naturally occurring sequence.

The invention also encompasses production of DNA sequences which encode TRNSFS and TRNSFS derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding TRNSFS or any fragment thereof.

Also encompassed by the invention are polynucleotide sequences that are capable of hybridizing to the claimed polynucleotide sequences, and, in particular, to those shown in SEQ ID NO:16–30 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 $\mu$g/ml denatured salmon sperm DNA (ssDNA). In a most preferred embodiment, hybridization will occur at 42° C. in 250 mM NaCl, 25 mM trisodium citrate, 1% SDS, 50% formamide, and 200 $\mu$g/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl. 3 mM trisodium citrate, and 0.1% SDS. In a more preferred embodiment, wash steps will occur at 42° C. in 15 mM NaCl. 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase 1, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.), and ABI CATALYST 800 thermal cycler (Perkin-Elmer). Sequencing is then carried out using the ABI 373 or 377 DNA sequencing systems (Perkin-Elmer), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Bioloey*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding TRNSFS may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA.

This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence-into 5' non-traniscribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode TRNSFS may be cloned in recombinant DNA molecules that direct expression of TRNSFS, or fragments or functional equivalents thereof, in appropriate host cells. Due to the inherent degeneracy of the genetic code, other DNA sequences which encode substantially the same or a functionally equivalent amino acid sequence may be produced and used to express TRNSFS.

The nucleotide sequences of the present invention can be engineered using methods generally known in the art in order to alter TRNSFS-encoding sequences for a variety of purposes including, but not limited to, modification of the cloning, processing, and/or expression of the gene product. DNA shuffling by random fragmentation and PCR reassembly of gene fragments and synthetic oligonucleotide may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding TRNSFS may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, TRNSFS itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin-Elmer). Additionally, the amino acid sequence of TRNSFS, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez. R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins. Structures and Molecular Properties*, WH Freeman, New York N.Y.)

In order to express a biologically active TRNSFS, the nucleotide sequences encoding TRNSFS or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding TRNSFS. Such elements may vary in their strength and specificity. Specific initiation signals may also be used to achieve more efficient translation of sequences encoding TRNSFS. Such signals include the ATG initiation codon and adjacent sequences, e.g. the Kozak sequence. In cases where sequences encoding TRNSFS and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding TRNSFS and appropriate transcriptional and translational control elements. These methods include in vitro recombinant DNA techniques, synthetic techniques, and in vivo genetic recombination. (See, e.g., Sambrook. J. et al. (1989) *Molecular Cloning. A Laboratory Manual*, Cold Sprint Harbor Press, Plainview N.Y., ch. 4, 8, and 16–17; Ausubel, F. M. et al. (.1995) *Current Protocols in Molecular Biology*, John Wiley & Sons, New York N.Y., ch. 9, 13, and 16.)

A variety of expression vector/host systems may be utilized to contain and express sequences encoding TRNSFS. These include, but are not limited to, microorganisms such as vectors, yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus.TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding TRNSFS. For example, routine cloning, subcloning, and propagation of polynucleotide sequences encoding TRNSFS can be achieved using a multifunctional *E. coli* vector such as PBLUESCRIPT (Stratagene, La Jolla Calif.) or PSPORT1 plasmid (Life Technologies). Ligation of sequences encoding TRNSFS into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke. G. and S. M. Schuster (1989) J. Biol. Chem. 264:5503–5509.) When large quantities of TRNSFS are needed, e.g. for the production of antibodies, vectors which direct high level expression of TRNSFS may be used. For example, vectors containing the strong, inducible T5 or T7 bacteriophage promoter may be used.

Yeast expression systems may be used for production of TRNSFS. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of TRNSFS. Transcription of sequences encoding TRNSFS may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Brogile, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding TRNSFS may be ligated into an adenovirus transcription/translation complex consisting of the late promoter and tripartite leader sequence. Insertion in a non-essential E1 or E3 region of the viral genome may be used to obtain infective virus which expresses TRNSFS in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of TRNSFS in cell lines is preferred. For example, sequences encoding TRNSFS can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk or apr cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes C. A. (1995) Methods Mol. Biol. 55:121–131.)

Although the presence/absence of marker gene expression suggests that the gene of interest is also present, the presence and expression of the gene may need to be confirmed. For example, if the sequence encoding TRNSFS is inserted within a marker gene sequence, transformed cells containing sequences encoding TRNSFS can be identified by the absence of marker gene function. Alternatively, a marker gene can be placed in tandem with a sequence encoding TRNSFS under the control of a single promoter. Expression of the marker gene in response to induction or selection usually indicates expression of the tandem gene as well.

In general, host cells that contain the nucleic acid sequence encoding TRNSFS and that express TRNSFS may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of TRNSFS using either specific polyclonal or monoclonal antibodies are known in the art. Examples of such techniques includeenzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on TRNSFS is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunolog*, Greene Pub. Associates and Wiley-lnterscience, New York N.Y.; and Pound, J. D. (1998) *Immunochemical Protocols*. Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding TRNSFS include oligolabeling, nick translation, end-labeling, or PCR amplification using a labeled nucleotide. Alternatively, the sequences encoding TRNSFS, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech. Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding TRNSFS may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode TRNSFS may be designed to contain signal sequences which direct secretion of TRNSFS through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas, Va.) and may be chosen to ensure the correct modification and processing of the foreign protein.

In another embodiment of the invention, natural, modified, or recombinant nucleic acid sequences encoding TRNSFS may be ligated to a heterologous sequence resulting in translation of a fusion protein in any, of the aforementioned host systems. For example, a chimeric TRNSFS protein containing a heterologous moiety that can be recognized by a commercially available antibody may facilitate the screening of peptide libraries for inhibitors of TRNSFS activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenyiarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a protcolvtic cleavage site located between the TRNSFS encoding sequence and the heterologous protein sequence, so that TRN SFS may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled TRNSFS may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of TRNSFS may be produced not only by recombinant production, but also by direct peptide synthesis using solid-phase techniques. (See, e.g., Creighton, supra, pp. 55–60.) Protein synthesis may be performed by manual techniques or by automation. Automated synthesis may be achieved, for example, using the ABI 431A peptide synthesizer (Perkin-Elmer). Various fragments of TRNSFS may be synthesized separately and then combined to produce the full length molecule.

THERAPEUTICS

Chemical and structural similarity, e.g., in the context of sequences and motifs, exists between regions of TRNSFS and human transferase proteins. In addition, the expression of TRNSFS is closely associated with cancerous and proliferating, gastrointestinal, inflamed, immunological, nervous, reproductive and smooth muscle tissue and fetal cell lines. Therefore, TRNSFS appears to play a role in cancer, developmental disorders, gastrointestinal disorders, genetic disorders, immunological disorders, neurological disorders, reproductive disorders, and smooth muscle disorders. In the treatment of disorders associated with increased TRNSFS expression or activity, it is desirable to decrease the expression or activity of TRNSFS. In the treatment of disorders associated with decreased TRNSFS expression or activity, it is desirable to increase the expression or activity of TRNSFS.

Therefore, in one embodiment, TRNSFS or a fragment or derivative thereof may be administered to a subject to treat or prevent a disorder associated with decreased expression or activity of TRNSFS Examples of such disorders include but are not limited to, a cancer, such as adenocarcinoma, leukemia, lymphoma, melanoma, myeloma, sarcoma, teratocarcinoma, and, in particular, cancers of the adrenal gland, bladder bone, bone marrow, brain breast, cervix, gall bladder, ganglia, gastrointestinal tract, heart, kidney, liver, lung, muscle, ovary, pancreas. parathyroid, penis, prostate, salivary glands, skin, spleen, testis, thymus, thyroid, and uterus, a developmental disorder, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary kleratodermas, hereditary neuropathies such as Charcot-Marie-Tooth disease and neurofibromatosis, hypothyroidism, hydrocephalus, seizure disorders such as Syndenham's chorea and cerebral palsy, spina bifida; anencephaly, craniorachischisis, congenital glaucoma, cataract, and sensorineural hearing loss; a gastrointestinal disorder, such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, and acquired immunodeficiency syndrome (AIDS) enteropathy; a genetic disorder, such as Lesch-Nyhan syndrome, mitochondrial camitine palmitoyl transferase deficiency, carnitine deficiency, peroxisomal acyl-CoA oxidase deficiency, peroxisomal thiolase deficiency, peroxisomal bifunctional protein deficiency, mitochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, mitochondrial short-chain 3-hydroxyacyl-CoA dehydrogenase deficiency, adrenoleuklodystrophy, Alport's syndrome, choroideremia, Duchenne and Becker muscular dystrophy, Down's syndrome, cystic fibrosis, chronic granulomatous disease, Gaucher's disease, Huntington's chorea, Marfan's syndrome, muscular dystrophy, myotonic dystrophy, pycnodysostosis, Refsum's syndrome, retinoblastoma, sickle cell anemia, thalassemia, Werner syndrome, von Willebrand's disease, Wilms' tumor, and Zellweger syndrome, an immunological disorder, such as inflammation, actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, crythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjögren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, trauma, and hematopoietic cancer including lymphoma, leukemia, and myeloma; a neurological disorder, such as epilepsy, ischemic cerebrovascular disease, stroke, cerebral neoplasms, Alzheimer's disease, Pick's disease, Hunting-ton's disease, dementia, Parkinson's disease and other extrapyramidal disorders, amyotrophic lateral'sclerosis and other motor neuron disorders, progressive neural muscular atrophy, retinitis pigmentosa, hereditary ataxias, multiple sclerosis and other demyelinating diseases bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorder of the central nervous system, cerebral palsy, a neuroskeletal disorder, an autonomic nervous system disorder a cranial nerve disorder, a spinal cord disease, muscular dystrophy and other neuromuscular disorder, a peripheral nervous system disorder, dermatomyositis and polymyositis; inherited, metabolic, endocrine, and toxic myopathy; myasthenia gravis, periodic paralysis; a mental disorder including mood, anxiety, and schizophrenic disorders; seasonal affective disorder (SAD); akathesia, amnesia, catatonia, diabetic neuropathy, tardive dyskinesia, dystonias, paranoid psychoses, postherpetic neuralgia, and Tourette's disorder; a reproductive disorder, such as disorders of prolactin production; infertility, including tubal disease, ovulatory defects, and endometriosis, disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea, disruptions of spermnatosgenesis, abnormal sperm physiology, cancer of the testis, cancer of the prostate, benign prostatic hyperplasia, prostatitis, Peyronie's disease, impotence, carcinoma of the male breast, and gynecomastia; and a smooth muscle disorder, such as angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Keams-Sayre syndrome, lactic acidosis, myoclonic disorder, and ophthalmoplegia. A smooth muscle disorder is defined as any impairment or alteration in the normal action of smooth muscle and may include those disorders listed above. Smooth muscle includes, but is not limited to, that of the blood vessels, gastrointestinal tract, heart, and uterus.

In another embodiment, a vector capable of expressing TRNSFS or a fragment or derivative thereof may be administered to a subject to treat or prevent a disorder associated with decreased expression or activity of TRNSFS including, but not limited to, those described above.

In a further embodiment, a pharmaceutical composition comprising a substantially purified TRNSFS in conjunction with a suitable pharmaceutical carrier may be administered to a subject to treat or prevent a disorder associated with decreased expression or activity of TRNSFS including, but not limited to, those provided above.

In still another embodiment, an agonist which modulates the activity of TRNSFS may be administered to a subject to treat or prevent a disorder associated with decreased expression or activity of TRNSFS including, but not limited to, those listed above.

In a further embodiment, an antagonist of TRNSFS may be administered to a subject to treat or prevent a disorder associated with increased expression or activity of TRNSFS.

Examples of such disorders include, but are not limited to, those described above. In one aspect, an antibody which specifically binds TRNSFS may be used directly as an antagonist or indirectly as a targeting or delivery mechanism for bringing a pharmaceutical agent to cells or tissue which express TRNSFS.

In an additional embodiment, a vector expressing the complement of the poiynucleotide encoding TRNSFS may be administered to a subject to treat or prevent a disorder associated with increased expression or activity of TRNSFS including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of TRNSFS may be produced using methods which are generally known in the art. In particular, purified TRNSFS may be used to produce antibodies or to screen libraries of pharmaceutical agents to identify those which specifically bind TRNSFS. Antibodies to TRNSFS may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with TRNSFS or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to TRNSFS have an aminoacid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of TRNSFS amino acids may be fused with those of another protein, such as KLH, and antibodies to the chimeric molecule may be produced.

Monoclonal antibodies to TRNSFS may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 31 4:452–454.) Alternatively, techniques described for the production of single chain antibodies may be adapted, using methods known in the art, to produce TRNSFS-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for TRNSFS may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246: 1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between TRNSFS and its specific antibody. A two-site, monoclonal-based immunoassay utilizing monoclonal antibodies reactive to two non-interfering TRNSFS epitopes is preferred, but a competitive binding assay may also be employed, (Pound, supra).

Various methods such as Scatchard analysis in conjunction with radioimmunoassay techniques may be used to assess the affinity of antibodies for TRNSFS. Affinity is expressed as an association constant, $K_a$, which is defined as the molar concentration of TRNSFS-antibody complex divided by the molar concentrations of free antigen and free antibody under equilibrium conditions. The $K_a$ determined for a preparation of polyclonal antibodies, which are heterogeneous in their affinities for multiple TRNSFS epitopes, represents the average affinity, or avidity, of the antibodies for TRNSFS. The $K_a$ determined for a preparation of monoclonal antibodies, which are monospecific for a particular TRNSFS epitope, represents a true measure of affinity. High-affinity antibody preparations with $K_a$ ranging from about $10^9$ to $10^{12}$ L/mole are preferred for use in immunoassays in which the TRNSFS-antibody complex must withstand rigorous manipulations. Low-affinity antibody preparations with $K_a$ ranging from about $10^6$ to $10^7$ L/mole are preferred for use in immunopurification and similar procedures which ultimately require dissociation of TRNSFS, preferably in active form, from the antibody (Catty, D. (1988) *Antibodies Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polygonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of TRNSFS-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding TRNSFS, or any fragment or complement thereof, may be used for therapeutic purposes. In one aspect, the complement of the polynucleotide encoding TRNSFS may be used in situations in which it would be desirable to block the transcription of the mRNA. In particular, cells may be transformed with sequences complementary to polynucleotides encoding TRNSFS. Thus, complementary molecules or fragments may be used to modulate TRNSFS activity, or to achieve regulation of gene function. Such technology is now well known in the art, and sense or antisense oligonucleotides or larger fragments can be designed from various locations along the coding or control regions of sequences encoding TRNSFS.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding TRNSFS. (See, e.g., Sambrook, supra; Ausubel, 1995, supra.)

Genes encoding TRNSFS can be turned off by transforming a cell or tissue with expression vectors which express high levels of a polynucleotide, or fragment thereof, encoding TRNSFS. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-repiicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding TRNSFS. Oligonucleotides derived from the transcription initiation site, e.,g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding TRNSFS.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oiigonucleotides using ribonuclease protection assays.

Complementary ibonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding TRNSFS. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Deliverer by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of TRNSFS, antibodies to TRNSFS, and mimetics, agonists, antagonists, or inhibitors of TRNSFS. The compositions may be administered alone or in combination with at least one other agent, such as a stabilizing compound, which may be administered in any sterile biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth, and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids such as fatty oils, liquid, or liquid polyethylene glycol with or without stabilizers.

Pharrnaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable ipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0. 1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of TRNSFS, such labeling would include amount. frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example TRNSFS or fragments thereof, antibodies of TRNSFS, and agonists, antagonists or inhibitors of TRNSFS, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which, can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmnaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind TRNSFS may be used for the diagnosis of disorders characterized by expression of TRNSFS, or in assays to monitor patients being treated with TRNSFS or agonists, antagonists, or inhibitors of TRNSFS. Antibodies useful for diagnostic purposes may be prepared in the same manner as described above for therapeutics. Diagnostic assays for TRNSFS include methods which utilize the antibody and a label to detect TRNSFS in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring TRNSFS, including ELISAs, RIAs, and FACS, are known in the art and provide a basis for diagnosing altered or abnormal levels of TRNSFS expression. Normal or standard values for TRNSFS expression are established by combining body fluids or cell extracts taken from normal mammalian subjects, preferably human, with antibody to TRNSFS under conditions suitable for complex formation. The amount of standard complex formation may be quantitated by various methods, preferably by photometric means. Quantities of TRNSFS expressed in subject, control, and disease samples from biopsied tissues are compared with the standard values. Deviation between standard and subject v values establishes the parameters for diagnosing disease.

In another embodiment of the invention, the polynucleotides encoding TRNSFS may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of TRNSFS may be correlated with disease. The diagnostic assay may be used to determine absence, presence, and excess expression of TRNSFS, and to monitor regulation of TRNSFS levels during therapeutic intervention.

In one aspect, hybridization with PCR probes which are capable of detecting polynucleotide sequences, including genomic sequences, encoding TRNSFS or closely related molecules may be used to identify nucleic acid sequences which encode TRNSFS. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding TRNSFS, allelic variants, or related sequences.

Probes may also be used for the detection of related sequences, and should preferably have at least 50% sequence identity to any of the TRNSFS encoding sequences. The hybridization probes of the subject invention may be DNA or RNA and may be derived from the sequence of SEQ ID NO:16–30 or from genomic sequences including promoters, enhancers, and introns of the TRNSFS gene.

Means for producing specific hybridization probes for DNAs encoding TRNSFS include the cloning of polynucleotide sequences encoding TRNSFS or TRNSFS derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$p or $^{35}$S, or by enzymatic labels, such as alkaline phosphatase coupled to the probe via avidin/biotin coupling systems, and the like.

Polynucleotide sequences encoding TRNSFS may be used for the diagnosis of disorders associated with expression of TRNSFS. Examples of such disorders include but are not limited to, a cancer, such as adenocarcinoma, leukemia, lymphoma, melanomna, myeloma, sarcoma, teratocarcinoma, and, in particular, cancers of the adrenal gland, bladder, bone, bone marrow, brain breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a developmental disorder, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as CharcotMarie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; a gastrointestinal disorder, such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious coiitis, ulcerative colitis, ulcerative proctitis, Crohn's disease, Whipple's disease, MalloryWeiss syndrome, colonic carcinoma, colonic obstruction, irritable bowel syndrome, short bowel syndrome, diarrhea, constipation, gastrointestinal hemorrhage, and acquired immunodeficiency syndrome (AIDS) enteropathy; a genetic disorder, such as Lesch-Nyhan syndrome, mitochondrial carnitine palmitoyi transferase deficiency, carnitine deficiency, peroxisomal acyl-CoA oxidase deficiency, peroxisomal thiolase deficiency, peroxisomal bifunctional protein deficiency, mitochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, mitochondrial short-chain 3-hydroxyacyl-CoA dehydrogenase deficiency, adrenoleukodystrophy, Alport's syndrome, choroideremia, Duchenne and Becker muscular dystrophy, Down's syndrome, cystic fibrosis, chronic granulomatous disease, Gaucher's disease, Huntington's chorea, Marfan's syndrome, muscular dystrophy, myotonic dystrophy, pycnodvsostosis, Refsurn's syndrome, retinoblastoma, sickle cell anemia, thalassemia, Werner syndrome, von Willebrand's disease, Wilms' tumor, and Zeliweger syndrome; an immunological disorder, such as inflammation, actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjögren's syndrome, systemic anaphylaxis, systemic lupus ernihematosus, systemic sclerosis, primary thrombocythemia, thrombocytopenic purpura, ulcerative colitis, uveitis, Werner syndrome, complications of cancer, hemodialysis, and extracorporeal circulation, trauma, and hematopoietic cancer including lymphoma, leukemia, and myeloma; a neurological disorder, such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess;subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorder of the central nervous system, cerebral palsy, a neuroskeletal disorder, an autonomic nervous system disorder, a cranial nerve disorder, a spinal cord disease, muscular dystrophy and other neuromuscular disorder, a peripheral nervous system disorder, dermatomyositis and polymyositis; inherited, etabolic, endocrine, and toxic myopathy; myasthenia gravis, periodic paralysis; a mental disorder including mood, anxiety, and schizophrenic disorders; seasonal affective disorder (SAD); akathesia, amnesia, catatonia, diabetic neuropathy, tardive dyskinesia, dystonias, paranoid psychoses, postherpetic neuralgia, and Tourette's disorder; a reproductive disorder, such as disorders of prolactin production; infertility, including tubal disease, ovulatory defects, and endometriosis, disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactdrrhea, disruptions of spermatogenesis, abnormal sperm physiology, cancer of the testis, cancer of the prostate, benign prostatic hyperplasia, prostatitis, Peyronie's disease, impotence, carcinoma of the male breast, and vynecomastia, and a smooth muscle disorder, such as angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Keams-Sayre syndrome, lactic acidosis, myoclonic disorder, and ophthalmoplegia. The polynucleotide sequences encoding TRNSFS may be used in Southern or Northern analysis, dot blot, or other membrane-based technologies, in PCR technologies; in dipstick, pin, and multiformat ELISA-like assays, and in microarrays utilizing fluids or tissues from patients to detect altered TRNSFS expression. Such qualitative or quantitative methods are well known in the art.

In a particular aspect, the nucleotide sequences encoding TRNSFS may be useful in assays that detect the presence of associated disorders, particularly those mentioned above. The nucleotide sequences encoding TRNSFS may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding TRNSFS in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of TRNSFS, a normal or standard profile for expression is established. This may be accomplished by combining body fluids or cell extracts taken from normal subjects, either animal or human, with a sequence, or a fragment thereof, encoding TRNSFS, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated. hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding TRNSFS may involve the use of PCR. These oligomers may be chemically synthesized, generated enzymatically, or produced in vitro. Oligomers will preferably contain a fragment of a polynucleotide encoding TRNSFS, or a fragment of a polynucleotide complementary to the polynucleotide encoding TRNSFS, and will be employed under optimized conditions for identification of a specific gene or condition. Oligomers may also be employed under less stringent conditions for detection or quantitation of closely related DNA or RNA sequences.

Methods which may also be used to quantify the expression of TRNSFS include radiolabeling or biotinylating nucleotides; coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci.93:10614–10619, Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding TRNSFS may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355, Price, C. M. (1993) Blood Rev. 7:127–134, and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correiation between the location of the gene encoding TRNSFS on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, TRNSFS, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between TRNSFS and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with TRNSFS, or fragments thereof, and washed. Bound TRNSFS is then detected by methods well known in the art. Purified TRNSFS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding TRNSFS specifically compete with a test compound for binding TRNSFS. In this manner, antibodies can be used to detect the presence of any peptide which shares one or more antigenic determinants with TRNSFS.

In additional embodiments, the nucleotide sequences which encode TRNSFS may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all patents, applications, and publications mentioned above and below, in particular U.S. Ser. No. [Attorney Docket No: PF-0592 P, filed Sep. 10, 1998], U.S.

Ser. No. [Attorney Docket No: PF-0624 P. filed Nov. 4, 1998], and U.S. Ser. No. 60/133,642, are hereby expressly incorporated by reference.

EXAMPLES

1. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies). using the recommended procedures or similar methods known in the art. (See, e.g., Ausubel, 1997 supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected-(300–1000 bp) using SEPHACRYL S1000, SEPHAROSE CL2B, or SEPHAROSE CL4B column chromatography (Amersham Pharmacia Biotech) or preparative agarose gel electrophoresis, cDNAs were ligated into compatible restriction enzyme sites of the polylinker of a suitable plasmid, e.g., PBLUESCRIPT plasmid (Stratagene), pSPORT1 plasmid (Life Technologies), or pINCY (Incyte Pharmaceuticals, Palo Alto Calif.). Recombinant plasmnids were transformed into competent E. coli cells including XL1-Blue, XL1-BlueMRF, or SOLR from Stratagene or DH5α, DH10B, or ElectroMAX DH10B from Life Technologies.

II. Isolation of cDNA Clones

Plasmids were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8, QIAWELL 8 Plus, QIAWELL 8 Ultra plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Sampleswere processed and stored in 384-well plates, and the concentration of amplified plasmid DNA was quantified fluorometrically using PICOGREEN dye (Molecular Probes. Eugene Oreg.) and a FLUOROSKAN II fluorescence scanner (Labsystems Oy, Helsinki, Finland).

III. Sequencing and Analysis cDNA sequencing reactions were processed using standard methods or high-throughput instrumentation such as the ABI CATALYST 800 (Perkin-Elmer) thermal cycler or the PTC-200 thermal cycler (MJ Research) in conjunction with the HYDRA microdispenser (Robbins Scientific) or the MICROLAB 2200 (Hamilton) liquid transfer system, cDNA sequencing reactions were prepared using reagents provided by Amersham Pharmacia Biotech or supplied in ABI sequencing kits such as the ABI PRISM BIGDYE Terminator cycle sequencing ready reaction kit (Perkin-Elmer). Electrophoretic separation of cDNA sequencing reactions and detection of labeled poiynucleotides were carried out using the MEGABACE 1000 DNA sequencing system (Molecular Dynamics); the ABI PRISM 373 or 377 sequencing systems (Perkin-Elmer) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example V.

The polynucleotide sequences derived from cDNA sequencing were assembled and analyzed using a combination of software programs which utilize algorithms well known to those skilled in the art. Table 5 summarizes the tools, programs, and algorithms used and provides applicable descriptions, references, and threshold parameters. The first column of Table 5 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score, the greater the homology between two sequences). Sequences were analyzed using MAcDNASIS PRO software (Hitachi Software Engineering, South San Francisco Calif.) and LASERGENE software (DNASTAR). Polynucleotide and polypeptide sequence alignments were generated using the default parameters specified by the clustal algorithm as incorporated into the MEGALIGN multisequence alignment program (DNASTAR), which also calculates the percent identity between aligned sequences.

The polynucleotide sequences were validated by removing vector, linker, and polyA sequences and by masking ambiguous bases, using algorithms and programs based on BLAST, dynamic programing, and dinucieotide nearest neighbor analysis. The sequences were then queried against a selection of public databases such as the GenBank primate, rodent, mammalian, vertebrate, and eukaryote databases, and BLOCKS to acquire annotation using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide, sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probabilistic approach which analyzes consensus primary structures of gene families. (See, e.g., Eddy, S. R. (1996) Curr. Opin. Str. Biol. 6:361–365.)

The programs described above for the assembly and analvsis of full length polynucleotide and amino acid sequences were also used to identify polynucleotide sequence fragments from SEQ ID NO:16–30. Fragments from about 20 to about 4000 nucleotides which are useful in hybridization and amplification technologies were described in The Invention section above.

IV. Northern Analysis.

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

% sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding TRNSFS occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, fetal, neurological, and pooled. For each category, the number of libraries expressing the sequence of interest was counted and divided by the total numiber of libraries across all categories. Percentage values of tissue-specific and disease- or condition-specific expression are reported in Table 3.

V. Extension of TRNSFS Encoding Polonucleotides

The full length nucleic acid sequences of SEQ ID NO:16 and of SEQ ID NO:18–30 were produced by extension of an appropriate fragment of the full length molecule using oligonucleotide priiners designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C., to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; step 6: 68° C., 5 min; Step 7: storage at 4° C. In the alternative, the parameters for primer pair T7 and SK+ were as follows: Step 1: 94° C,3 mm; Step 2: 94° C. 15 sec; Step 3: 57° C., 1 min; Step 4: 68° C.,2 mmin; Step 5: Steps 2,3, and 4 repeated 20 times; Step 6: 68° C. 5 min; Step 7: storage at 4° C.

The concentration of DNA in each well was determined by dispensing 100 μl PICOGREEN quantitation reagent (0.25% (v/v) PICOGKEEN; Molecular Probes, Eugene Oreg.) dissolved in IX TE and 0.5 μl of undiluted PCR product into each well of an opaque fluorimeter plate (Comning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reactionmixture was analyzed by electrophoresis on a 1% agarose mini-gel to determine which reactions were successful in extending the sequence.

The extended nucleotides were desalted and concentrated, transferred to 384-well plates. digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cellswere selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C. 1 min; Step 4: Step 5: steps 2, 3, and 4 repeated 29 times; Step 6: 72° C, 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharrnacia Biotech) or the ABI PRISM BIGDYE Terminator cycle sequencing ready reaction kit (Perkin-Elmer).

In like manner, the nucleotide sequences of SEQ ID NO:16 and of SEQ ID NO:18–30 are used to obtain 5' regulatory sequences using the procedure above, oligonucleotides designed for such extension, and an appropriate genomic library.

The full length nucleic acid sequence of SEQ ID NO:17 was producedby extension of an appropriate fragment of the full length molecule, using oligonucleotide primers designed from this fragment. One primer was synthesized to initiate extension of an antisense polynucleotide, and the other was synthesized to initiate extension of a sense polynucteotide. Primers were used to facilitatethe extension of the known sequence "outward" generating amplicons containing new unknown nucleotide sequence for the region of interest. The initial primers were designed from the cDNA using OLIGO 4.06 software (National Biosciences, Plymouth, Minn.), or another appropriate program, to be about 22 to 30 nucleotides in length, to have a GC content of about 50% or more, and to anneal to the target sequence at temperatures of about 68° C., to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

Highfidelity amplification was obtained by following the instructions for the XL-PCR kit (Perkin-Eimer Corp., Norwalk, Conn.) and thoroughly mixing the enzyme and reaction mix. PCR was performed using the PTC-200 thermal cycler (MJ Research, Inc. Watertown, Mass.), beginning with 40 pmol of each primer and the recommended concentrations of all other components of the kit, with the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat steps 4 through 6 for an additional 15 cycles
Step 8 94° C. for 15 sec
Step 9 65° C. for 1 min
Step 10 68° C. for 7:15 min
Step 11 Repeat steps 8 through 10 for an additional 12 cycles
Step 12 72° C. for 8 min
Step 13 4° C. (and holding)

A 5 μl to 10 μaliquot of the reaction mixture was analyzed by electrophoresis on a low concentration (about 0.6% to 0.8%) agarose mini-gel to determine which reactions were successful in extending the sequenrce. Bands thought to contain the largest products were excised from the gel, purified using QIAQUICK DNA gel purification kit (Qiagen, Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent *E. coli* cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2 through 4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:17 is used to obtain 5' regulatory sequences using the procedure above, oligonucleotides designed for 5' extension, and an appropriate genomic library.

VI. Labeling and Use of individual Hybridization Probes

Hybridization probes derived from SEQ ID NO:16–30 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN).

The DNA from each digest is fractionaied on a 0.7% agarose gel and transferred to nvion membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1 × saline sodium citrate and 0.5% sodium dodecyl sulfate. Hybridization patterns are visualized using autoradiography and compared.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs. Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV-cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the TRNSFS-encoding sequences, or any parts thereof, are used to detect, decrease, or inhibit expression of naturally occurring TRNSFS. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of TRNSFS. To inhibit transcription, a complementary oligonucleotide is designed from the most unique 5' sequence and used to prevent promoter binding to the coding sequence. To inhibit translation, a complementary oligonucleotide is designed to prevent ribosomal binding to the TRNSFS-encoding transcript.

IX. Expression of TRNSFS

Expression and purification of TRNSFS is achieved using bacterial or virus-based expression systems. For expression of TRNSFS in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express TRNSFS upon induction with isopropyl beta-D-thiogalactopyranoside (IPTG). Expression of TRNSFS in eukaryotic cells is achieved by infecting insect or mammalian cell lines with recombinant *Autoizrahica californica* nuclear polyhedrosis virus (AcMNPV), commonly known as baculovirus. The nonessential polyhedrin geneof baculovirus is replaced with cDNA encoding TRNSFS by either homologous recombination or bacterial-mediated transposition involving transfer plasmid intermediates. Viral infectivity is maintained and the strong poyhedrin promoter drives high levels of cDNA transcription. Recombinant baculovirus is used to infect *Spodontera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, TRNSFS is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions, that maintain protein activity and antigenicity (Amersham Pharmacia Biotech). Following purification, the GST moiety can be proteolytically cleaved from TRNSFS at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified TRNSFS obtained by these methods can be used directly in the following activity assay.

X. Demonstration of TRNSFS Activity

TRNSFS activity is determined by measuring the transfer of a radiolabeled molecular group from a donor to an acceptor molecule in the presence of TRNSFS. For example, HNK sulfotransferase activity is determined in a reaction mixture that contains 0.02 mM [$^{35}$S]PAPS, 25 µl of IgG bead-bound enzyme suspension, 0.1 mM acceptor oligosaccharides or 0.0265 mM acceptor glycolipids in 100 mM TRIS-HCl, pH 7.2, 0.1% Triton X-100, 10 mM $MnCl_2$, and 2.5 mM ATP. The mixture is incubated for two hours at 37° C. The reaction products are adjusted to 0.25 M ammonium formate, pH 4.0, and separated on a C18 reverse phase chromatography column. The column is washed and the products are eluted with 70% methanol. The radioactivity recovered in the acceptor molecule is measured using a liquid scintillation counter and, is proportional to the activity of HNK sulfotransferase in the assay.

Alternatively, myristoyl CoA:protein N-myristoyltransferase activity is demonstrated as the ability of TRNSFS to myristoylate a synthetic peptide substrate using the methods known in the art. (Giang, D. K. and Cravatt, B. F. (1998) J. Biol. Chem. $2_73$:6595–65$_{98}$; and Towler and Glaser (1986) Proc. Natl. Acad. Sci., 83:2812–2816.) [$^3$H]Myristoyl-CoA (0.75 µCi; 52.Ci/mmol; 0.3 µM; Amersham Pharmacia Biotech) is added to a mixture of COS-7 total cell protein (7.5 µg) and peptide substrate (200 µM; Towler and Glaser, supra) in a reaction buffer of 30 mM tris-HCl, pH 7.5, with 0.5 mM EDTA, 0.5 mM EGTA, 1.0% (v/v) Triton X-100, and 4.5 mM mercaptoethanol (total reaction volume of 50 µl). The reaction is allowed to proceed for 10 min at 25° C., then quenched with 50 µl of methanol followed by 5 µl of 100% trichloroacetic acid, placed on ice for 10 min, and spun at 10,000 × g for 5 min. Aliquots (25 µl) of the supernatant are analyzed by reverse-phase high pressure liquid chromatography. A myristoylated peptide is synthesized as described (Towler and Glaser, supra) and used as a standard to define the elution times for myristoylated peptide products. Column fractions (1 ml) are collected and counted by scintillation counting. In all cases, control reactions without peptide are also analyzed and subtracted from reactions with peptide to provide myristoyl-transferase reaction rates. Initial rates are determrined from reactions in which less than 20% myristoylated product is formed. Myristoyltransferase reaction rate is proportional to the amount of TRNSFS present in the sample.

Alternatively, mannose-1-phosphate guanyltransferase activity is determined by combining TRNSFS with its substrates GTP and α-D-mannose-1-phosphate at stoichometric quantities under buffered conditions. At appropriate time points the products, CDP-ethanolamine and diphosphate are measured with chromatographic methods, whereby the reaction products are separated from the substrates. Under the standardized conditions of the assay, the amounts of CDP-ethanolamine and diphosphate produced are directly proportional to the activity of TRNSFS in biological samples.

XI. Functional Assays

TRNSFS function is assessed by expressing the sequences encoding TRNSFS at physiologically elevated levels in mammalian cell culture systems, cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide: changes in cell size and granularity as measured by forward light scatter and 90 degree side light scatter: down-regulation of DNA synthesis as measured by decrease in bromodeoxyuridine uptake; alterations in expression of cell surface and intracellular proteins as measured by reactivity with specific antibodies; and alterations in plasma-membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of TRNSFS on gene expression can be assessed using highly purified populations of cells transfected with sequences encoding TRNSFS and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.), mRNA can be purified from the cells using methods well known by those of skill in the art. Expression of mRNA encoding TRNSFS and other genes of interest can be analyzed by Northern analysis or microarray techniques.

XII. Production of TRNSFS Specific Antibodies

TRNSFS substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the TRNSFS amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A peptide synthesizer (Perkin-Elmer) using fmoc-chemistry and coupled to KLH (Sigma-Aldrich. St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic blocking with 1% BSA, reacting with rabbit antisera, washing, and reacting with radio-iodinated goat anti-rabbit IgG.

XIII. Purification of Naturally Occurring TRNSFS Using Specific Antibodies

Naturally occurring or recombinant TRNSFS is substantially purified by immunoaffinity chromatography using antibodies specific for TRNSFS. An immunoaffinity column is constructed by covalently coupling anti-TRNSFS antibddy to an activated chromatographic resin, such as CNBr-activated SEPHAROSE (Amersham Pharmacia Biotech). After the coupling, the resin is blocked and washed according to the manufacturer's instructions.

Media containing TRNSFS are passed over the immunoaffinity column, and the column is washed under conditions that allow the preferential absorbance of TRNSFS (e.g., high ionic strength buffers in the presence of detergent). The column is eluted under conditions, that disrupt antibody/TRNSFS binding (e.g., a buffer of pH 2 to pH 3, or a high concentration of a chaotrope such as urea or thiocyanate ion), and TRNSFS is collected.

XIV. Identification of Molecules Which Interact with TRNSFS

TRNSFS, or biologically active fragments thereof, are labeled with $^{125}$I Bolton-Hunter reagent. (See, e.g., Bolton et al. (1973) Biochem, J. 133:529.) Candidate molecules previously arrayed in the wells of a multi-well plate are incubated with the labeled TRNSFS, washed, and any wells with labeled TRNSFS complex are assayed. Data obtained using different concentrations of TRNSFS are used to calculate values for the number, affinity, and association of TRNSFS with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which, are obvious to those skilled in molecular biology or related fields are intended to be within the scope of the following claims.

TABLE 1

| Protein SEQ ID NO: | Nucleotide SEQ ID NO: | Clone ID | Library | Fragments |
|---|---|---|---|---|
| 1 | 16 | 1632930 | COLNNOT19 | 1632930H1, 1632930T6.COMP, and 1632930F6 (COLNNOT19), 2616972T6.comp (GBLANOT01), 1001793H1 (BRSTNOT03), 132272H1 (BLADNOT04), 2535979H1 (BRAINOT18), 2779012T6.comp (OVARTUT03) |
| 2 | 17 | 2682663 | SINIUCT01 | 2682663H1 (SINIUCT01), 2483825H1 (SMCANOT01), 78548R1 (PROSNOT05), 2643432F6 (LUNGTUT08), 1214388H1 (BRSTTUT01), 2122443T6 (BRSTNOT07), 2278985R6 (PROSNON01) |
| 3 | 18 | 1265094 | SYNORAT05 | 266269H1 (HNT2NOT01), 605479R6 and 605479T6 (BRSTTUT01), 870033R6 (LUNGAST01), 928166R6 (BRAINOT04), 1265094111 (SYNORAT05), 1914656H1 (PROSTUT04), 2737452H1 (OVARNOT09), 3351376H1 (PROSNOT28), 4998035H1 (MYEPTXT02), 5121429H1 (SMCBUNT01) |
| 4 | 19 | 1404963 | LATRTUT02 | 1404963H1 and 1404963T6 (LATRTUT02), 1742179T6 (HIPONON01), 2055278X19R1 (BEPINOT01), SBMA02021F1, SBMA03096F1, SBMA01345F1 |
| 5 | 20 | 1405058 | LATRTUT02 | 154037H1 (THPIPLB02), 1405058F6, 1405058H1, and 14050586T6 (LATRTUT02), 2371445F6 (ADRENOT07), 3235888F7 (COLNUCT03), 3674493H1 (PLACNOT07), 4985152H1 (LIVRTUT10) |
| 6 | 21 | 1420940 | KIDNNOT09 | 493640X19 (HNT2NOT01), 983695H1 (TONGTUT01), 1361219F6, 1361219X11, 1361219X13, and 1362434X11 (LUNGNOT12), 1420940H1 (KIDNNOT09), 1499443T6 (SINTBST01), 3655410F6 (ENDINOT02) |
| 7 | 22 | 1784742 | BRAINOT10 | 1286822H1 (BRAINOT11), 1784742H1 (BRAINOT10), 3243626H1 and 3244456F6 (BRAINOT19), 5013854F6 (BRAXNOT03) |
| 8 | 23 | 1967138 | BRSTNOT04 | 1513726T6 (PANCTUT01), 1967138H1 (BRSTNOT04), SAE03142R1, SAE01673F1 |
| 9 | 24 | 2124351 | BRSTNOT07 | 288743F1 (EQSIHET02), 582937H1 (PROSNOT02), 890499R1 (STOMTUT01), 1380837F1 (BRAITUT08), 144442F1 (THYRNOT03), 2124351H1 (BRSTNOT07), 2159702F6 (ENDCNOT02) |
| 10 | 25 | 2153162 | BRAINOT09 | 269898X29R1, 495807F1 and 495807R1 (HNT2NOT01), 1450490F1 (PENITUT01), 2153162H1, 2153162X14F1, 2153162X22F1, 2153162X40F1, and 2153162X46F1 (BRAINOT09), 3114632H1 (BRSTNOT17) |
| 11 | 26 | 2617407 | GBLANOT01 | 2039925T6 (HIPONON02), 2617407F6 and 2617407H1 (GBLANOT01), 2620445R6 (KERANOT02), SBGA01193F1, SBGA05513F1, SBGA02306F1, SBGA03105F1 |
| 12 | 27 | 2963717 | SCORNOT04 | 1627889X24F1 (COLNPOT01), 2963717H1 and 2963717T6 (SCORNOT04), SBZA04180V1, SBZA00122V1, SBZA04721V1, SBZA00694V1 |
| 13 | 28 | 3360857 | PROSTUT16 | 538662R6 (LNODNOT02) 830729R1 and 830729T1 (PROSTUT04), 3360857H1 (PROSTUT16), 5069726H1 (PANCNOT23) |
| 14 | 29 | 3449671 | UTRSNON03 | 1418639T1 (KIDNNOT09), 1626239F6 (COLNPOT01), 1726392T6 (PROSNOT14), 2643253F6 (LUNGTUT08), 3049827F6 (LUNGNOT25), 3449671H1 (UTRSNON03), SBHA030521F1, SBHA03552F1, SBHA02654F1 |
| 15 | 30 | 5497787 | BRABDIR01 | 358882R6 (SYNORAB01), 773882R6 (COLNNOT05), 5497787H1 (BRABDIR01), 5673443H1 (182TF2T01) |

TABLE 2

| SEQ ID NO: | Amino Acid Residues | Potential Phosphorylation Sites | Potential Glycosylation Sites | Signature Sequence | Homologous Sequences | Analytical Methods |
|---|---|---|---|---|---|---|
| 1 | 498 | T64 S68 S166 S350 T462 T488 S220 S240 S258 T270 S295 T325 S350 S417 S490 | N319 N460 | Myristoyl-CoA protein N-myristoyltransferase: E246 - K254 K468 - G474 Myristoyl-CoA protein N-myristoyltransferase: E150 - I228 S240 - A285 G286 - F362 L436 - T488 | Myristoyl CoA:protein N-myristoyltransferase (g2443814) [Homo sapiens] | BLAST, Motifs, BLOCKS |
| 2 | 360 | T290 S78 T136 T191 S301 S348 S352 T21 T153 S168 S235 S259 Y144 | N265 N271 N322 | Bacterial hexapeptide-transferase: V256 - V284 Putative ADP-glucose pyrophosphorylase: V7 - A44 V106 - Y144 | Mannose-1-phosphate guanyltransferase (g2642159) [Arabidopsis thaliana] Mannose-1-phosphate guanyltransferase (g2804432) [Caenorhabditis elegans] | BLAST, Motifs, BLOCKS |
| 3 | 519 | S403 T248 T349 S409 S508 S18 T452 | N408 | TPR Domains: Y171 - P199 L205 - P223 W273 - P301 | O-linked GlnNAc transferase [Methanobacterium thermoautotrophicum] (g2521120) | BLAST, PFAM, Motifs |
| 4 | 225 | S176 S4 S117 S155 S96 S101 S111 T146 T149 T175 | N91 | Purine/pyrimidine phosphoribosyl-transferase Domain: Y35 - V225 | hypoxanthine (guanine) phosphoribosyl-transferase (g461344) | BLAST, PFAM, BLOCKS, Motifs |

TABLE 2-continued

| SEQ ID NO: | Amino Acid Residues | Potential Phosphorylation Sites | Potential Glycosylation Sites | Signature Sequence | Homologous Sequences | Analytical Methods |
|---|---|---|---|---|---|---|
| 5 | 338 | T103 T120 S239 T18 S41 T312 | N232 | Transmembrane Domain: G177 - A202 | octaprenyltransferase (g4982095) | BLAST, HMM, Motifs |
| 6 | 619 | S92 T176 S180 T198 T250 T285 S308 T313 T394 T453 T527 T548 T430 Y439 | N195 N298 | ATP/GTP-binding site (P-loop): G49 - T56 | ATP sulfurylase/APS kinase 2 [Homo sapiens] (g3342266) | BLAST, Motifs |
| 7 | 284 | S4 T11 T157 S174 T205 S260 S104 S148 S153 Y172 | | Sulfotransferase Protein Domain: H23 - K272 | Sulfotransferase-like protein (g1173670) | BLAST, PFAM, Motifs, BLOCKS |
| 8 | 205 | S49 T45 S201 | | Transmembrane Domain: L105 - L124 L169 - Y185 | phosphatidylethanol-amine N-methyl-transferase [Rattus norvegicus] (g310195) | BLAST, HMM, Motifs |
| 9 | 414 | T88 T239 S64 S96 S107 S257 S287 T344 S374 S375 S100 T312 S367 | N134 N209 N280 N370 | Signal Peptide: M1 - A31 Transmembrane Domain: L9 - D27 | HNK-1 sulfotransferase [Rattus norvegicus] (g1550716) | BLAST, SPScan, HMM, Motifs |
| 10 | 660 | S20 S93 T118 S153 T176 S233 S247 S248 S270 S280 T285 T433 S550 T24 T61 S105 T188 S362 S535 S632 Y104 | | Transmembrane Domain: T41 - I58 | N-acetylglucosaminyl-transferase I [Mus musculus] (g193527) | BLAST, HMM, Motifs |
| 11 | 386 | S121 S107 T217 S252 S364 T380 S35 S50 T81 T287 Y243 | N30 N308 N329 | Transmembrane Domain: M7 - F23 | N-acetylglucosamine 6-O-sulfotransferase (g4927116) [Mus musculus] | BLAST, HMM, Motifs |
| 12 | 803 | S739 S178 S195 T425 S471 T740 S775 T799 S38 S158 T182 S189 T313 S354 S396 T601 S734 S735 S744 | N312 | Acyltransferases ChoActase/COT/CPT family: S170 - A759 | carnitine palmitoyltransferase I [Rattus norvegicus] (g294521) | BLAST, PFAM, Motifs, BLOCKS, ProfileScan |
| 13 | 295 | T68 T83 S252 S88 | | | glycine N-methyltransferase [Sus scrofa] (g217690) | BLAST, Motifs |
| 14 | 575 | S350 S40 S57 S210 T233 S273 S305 T494 T2 S3 S44 T284 T345 S371 S549 | N110 N247 N250 | Transmembrane Domain: T73 - R94 | putative 3,4-dihydroxy-2-butanone kinase [Lycopersicon esculentum] (g1929056) | BLAST, HMM, Motifs |
| 15 | 180 | T15 | | | O-GlcNAc transferase p110 subunit (g1931579) | BLAST, Motifs |

TABLE 3

| Nucleotide SEQ ID NO: | Useful Fragments of Nucleotide Sequence | Tissue Expression (Fraction of Total) | Disease/Condition-Specific Expression (Fraction of Total) | Vector |
|---|---|---|---|---|
| 16 | 170–214 | Reproductive Nervous Smooth Muscle | Cancer Inflammation | pINCY |
| 17 | 377–406 | Reproductive Gastrointestinal | Cancer (0.530) Inflammation (0.280) | pINCY |
| 18 | 711–770, 915–959 1503–1562 | Reproductive (0.346) Nervous (0.212) | Cancer (0.519) Inflammation (0.173) | PSPORT1 |
| 19 | 649–693 | Nervous (0.368) Cardiovascular (0.263) Gastrointestinal (0.105) Reproductive (0.105) Hematopoietic/Immune (0.105) | Cancer (0.789) Inflammation (0.105) | pINCY |
| 20 | 833–892 | Gastrointestinal (0.238) Hematopoietic/Immune (0.190) Cardiovascular (0.143) | Inflammation (0.429) Cancer (0.381) Cell proliferation (0.238) | pINCY |
| 21 | 942–986 | Cardiovascular (0.245) Gastrointestinal (0.170) Reproductive (0.170) Endocrine (0.151) | Cancer (0.396) Inflammation (0.302) Cell Proliferation (0.170) | pINCY |
| 22 | 2–97 | Nervous (0.882) Endocrine (0.059) Developmental (0.059) | Neurological (0.294) Inflammation (0.235) Cancer (0.176) | pINCY |
| 23 | 3–62 | Reproductive (0.390) Nervous (0.186) Gastrointestinal (0.119) Cardiovascular (0.119) | Cancer (0.559) Trauma (0.136) Inflammation (0.102) | PSPORT1 |
| 24 | 396–440 444–503 | Reproductive (0.286) Nervous (0.265) Musculoskeletal (0.122) Hematopoietic/Immune (0.102) | Cancer (0.551) Inflammation (0.245) Cell proliferation (0.143) | pINCY |
| 25 | 207–266 321–380 | Reproductive (0.218) Nervous (0.188) Gastrointestinal (0.139) | Cancer (0.545) Inflammation (0.168) | pINCY |
| 26 | 264–323 1272–1331 | Dermatologic (0.500) Gastrointestinal (0.500) | Inflammation (0.500) Cell proliferation (0.500) | pINCY |
| 27 | 310–370 505–547 | Nervous (0.600) Gastrointestinal (0.133) Musculoskeletal (0.133) Reproductive (0.133) | Cancer (0.333) Trauma (0.200) Inflammation (0.133) Neurological (0.133) | pINCY |
| 28 | 368–412 | Gastrointestinal (0.417) Reproductive (0.417) Hematopoietic/Immune (0.167) | Cancer (0.333) Trauma (0.333) Inflammation (0.250) | pINCY |

TABLE 3-continued

| Nucleotide SEQ ID NO: | Useful Fragments of Nucleotide Sequence | Tissue Expression (Fraction of Total) | Disease/Condition-Specific Expression (Fraction of Total) | Vector |
|---|---|---|---|---|
| 29 | 458–502, 1196–1381 1460–1513 | Reproductive (0.279) Gastrointestinal (0.197) Nervous (0.131) | Cancer (0.492) Inflammation (0.164) Cell proliferation (0.164) | pINCY |
| 30 | 236–280 | Gastrointestinal (0.375) Endocrine (0.125) Hematopoietic/Immune (0.125) Musculoskeletal (0.125) Nervous (0.125) | Cancer (0.375) Inflammation (0.375) Neurological (0.125) | pINCY |

TABLE 4

| Polynucleotide SEQ ID NO: | Library | Library Description |
|---|---|---|
| 16 | COLNNOT19 | The library was constructed using RNA isolated from the cecal tissue of an 18-year-old Caucasian female. The cecal tissue, along with the appendix and ileum tissues, were removed during bowel anastomosis. Pathology indicated Crohn's disease of the ileum, involving 15 cm of the small bowel. |
| 17 | SINIUCT01 | The library ws constructed using RNA isolated from ileum tissue removed from a 420year-old Caucasian male during a total intra-abdominal colectomy and endoscopic jejunostomy. Pathology indicated that the disease was most severe in the colon with the distal end completely ulcerated. Patient history included tobacco abuse. Previous surgeries included polypectomy, colonoscopy, and spinal canal exploration. Family history included benign hypertension, cerebrovascular disease, athersclerotic coronary artery disease, and type II diabetes. |
| 18 | SYNORAT05 | The library was constructed using RNA isolated from the knee synovial tissue of a 62-year-old female with rheumatoid arthritis. |
| 19 | LATRTUT02 | The library was constructed using RNA isolated from a myxoma removed from the left atrium of a 43-year-old Caucasian male during annuloplasty. Pathology indicated atrial myxoma. Patient history included pulmonary insufficiency, acute myocardial infarction, atheroselerotic coronary artery disease, hyperlipidemia, and tobacco use. Family history included benign hypertension, acute myocardial infarction, atherosclerotic coronary artery disease, and type II diabetes. |
| 20 | LATRTUT02 | The library was constructed using RNA isolated from a myxoma removed from the left atrium of a 43-year-old Caucasian male during annuloplasty. Pathology indicated atrial myxoma. Patient history included pulmonary insufficiency, acute myocardial infarction, atheroselerotic coronary artery disease, hyperlipidemia, and tobacco use. Family history included benign hypertension, acute myocardial infarction, atherosclerotic coronary artery disease, and type II diabetes. |
| 21 | KIDNNOT09 | The library was constructed using RNA isolated from the kidney tissue of a Caucasian male fetus, who died at 23 weeks' gestation. |
| 22 | BARINOT10 | The library was constructed using RNA isolated from diseased cerebellum tissue removed from the brain of a 74-year-old Caucasian male, who died from Alzheimer's disease. |
| 23 | BRSTNOT04 | The library was constructed using RNA isolated from breast tissue removed from a 62-year-old East Indian female during a unilateral extended simple mastectomy. Pathology for the associated tumor tissue indicated an invasive grade 3 ductal carcinoma. Patient history included benign hypertension, hyperlipidemia, and hematuria. Family history included cerebrovascular and cardiovascular disease, hyperlipidemia, and liver cancer. |
| 24 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, cardiovascular disease, and type II diabetes. |
| 25 | BRAINOT09 | The library was constructed using RNA isolated from brain tissue removed from a Caucasian male fetus, who died at 23 weeks' gestation. |
| 26 | GBLANOT01 | The library was constructed using RNA isolated from diseased gallbladder tissue removed from a 53-year-old Caucasian female during a cholecystectomy. Pathology indicated mild chronic cholecystitis and cholelithiasis with approximately 150 mixed gallstones. Family history included benign hypertension. |
| 27 | SCORNOT04 | The library was constructed using RNA isolated from cervical spinal cord tissue removed from a 32-year-old Caucasian male who died from acute pulmonary edema and bronchopneumonia, bilateral pleural and pericardial effusions, and malignant lymphoma (natural killer cell type). Patient history included probable cytomegalovrius infection, hepatic congestion and steatosis, splenomegaly, hemorrhagic cystitis, thyriod hemorrhage, and Bell's palsy. Surgeries included colonoscopy, large intestine biopsy, adenotonsillectomy, and nasopharyngeal endoscopy and biopsy; treatment included radiation therapy. |
| 28 | PROSTUT16 | The library was constructed using RNA isolated from prostate tumor tissue removed from a 55-year-old Caucasian male. Pathology indicated adenocarcinoma, Gleason grade 5+4. Adenofibromatous hyperplasia was also present. The patient presented with elevated prostate specific antigen (PSA). Patient history included calculus of the kidney. Family history included lung cancer and breast cancer. |
| 29 | UTRSNON03 | The normalized library was constructed from 6.4 million independent clones from a uterus library. RNA was isolated from uterine myometrial tissue removed from a 41-year-old Caucasian female during a vaginal hysterectomy with dilation and curettage. The endometrium was secretory and contained fragments of endometrial polyps. Benign endo- ectocervical mucosa were identified in the endocervix. Pathology for the associated tumor tissue indicated uterine leiomyoma. Patient history included ventral hernia and a benign ovarian neoplasm. The normalization and hybridization conditions were adapted from Soares et al. (PNAS (1994) 91:9928). |
| 30 | BRABDIR01 | The library was constructed using RNA isolated from diseased cerebellum tissue removed from the brain of a 57-year-old Caucasian male, who died from a cerebrovascular accident. Patient history included Huntington's disease, emphysema, and tobacco abuse. |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/ PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblasin, and tblstx. | Altschul, S. F. et al. (1990) J. Mol. Biol. 215:403–410; Altschul, S. F. et al. (1997) Nucleic Acids Res. 25: 3389–3402. | ESTs: Probability value = 1.0E–8 or less Full Length sequences: Probability value = 1.0E–10 or less |
| FASTA | A Pearson and Lipman alogrithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W. R. (1990) Methods Enzymol. 183: 63–98; and Smith, T. F. and M. S. Waterman (1981) Adv. Appl. Math. 2:482–489. | ESTs: fasta E value = 1.06E–6 Assembled ESTs: fasta Identity = 95% or greater and Match length = 200 bases or greater; fastx E value = 1.0E–8 or less Full Length sequences: fastx score = 100 or greater |
| BLIMPS | A Blocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37: 417–424. | Score = 1000 or greater; Ratio of Score/Strength = 0.75 or larger; and Probability value = 1.0E–3 or less |
| PFAM | A Hidden Markov Models-based application useful for protein family search. | Krogh, A. et al. (1994) J. Mol. Biol. 235:1501–1531; Sonnhammer, E. L. I., et al. (1988) Nucleic Acids Res. 26:320–322. | Score = 10–50 bits, depending on individual protein families |
| ProfileScan | An algorithm that searches for structural sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington. Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claveric J. M. and S. Audic (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, pate M51–59, Genetics Computer Group, Madison, WI. | |

What is claimed is:

1. An isolated polynucleotide encoding a polypeptide comprising the amino acid sequence of SEQ ID NO:1.

2. A recombinant polynucleotide comprising a promoter sequence operably linked to the polynucleotide of claim 1.

3. A cell transformed with the recombinant polynucleotide of claim 2.

4. A method of producing a polypeptide comprising the amino acid sequence of SEQ ID NO:1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide comprising the anino acid sequence of SEQ ID NO:1, and
   b) recovering the polypeptide so expressed.

5. An isolated polynucleotide selected from the group consisting of:
   a) a polynucleotide comprising the polynucleotide sequence of SEQ ID NO:16,
   b) a polynucleotide completely complementary to the polynucleotide of a),
   c) an RNA equivalent of a) or b).

* * * * *

SEQUENCE LISTING

```
<160> NUMBER OF SEQ ID NOS: 33

<210> SEQ ID NO 1
<211> LENGTH: 498
<212> TYPE: PRT
<213> ORGANISM: Homo sapiens
<220> FEATURE:
<221> NAME/KEY: misc_feature
<223> OTHER INFORMATION: Incyte ID No: 1632930CD1

<400> SEQUENCE: 1

Met Ala Glu Asp Ser Glu Ser Ala Ala Ser Gln Gln Ser Leu Glu
  1               5                  10                  15

Leu Asp Asp Gln Asp Thr Cys Gly Ile Asp Gly Asp Asn Glu Glu
                 20                  25                  30
```

```
Glu Thr Glu His Ala Lys Gly Ser Pro Gly Gly Tyr Leu Gly Ala
                35                  40                  45

Lys Lys Lys Lys Lys Gln Lys Arg Lys Glu Lys Pro Asn
                50                  55                  60

Ser Gly Gly Thr Lys Ser Asp Ser Ala Ser Asp Ser Gln Glu Ile
                65                  70                  75

Lys Ile Gln Gln Pro Ser Lys Asn Pro Ser Val Pro Met Gln Lys
                80                  85                  90

Leu Gln Asp Ile Gln Arg Ala Met Glu Leu Leu Ser Ala Cys Gln
                95                 100                 105

Gly Pro Ala Arg Asn Ile Asp Glu Ala Ala Lys His Arg Tyr Gln
               110                 115                 120

Phe Trp Asp Thr Gln Pro Val Pro Lys Leu Asp Glu Val Ile Thr
               125                 130                 135

Ser His Gly Ala Ile Glu Pro Asp Lys Val Asn Val Arg Gln Glu
               140                 145                 150

Pro Tyr Ser Leu Pro Gln Gly Phe Met Trp Asp Thr Leu Asp Leu
               155                 160                 165

Ser Asp Ala Glu Val Leu Lys Glu Leu Tyr Thr Leu Leu Asn Glu
               170                 175                 180

Asn Tyr Val Glu Asp Asp Asn Met Phe Arg Phe Asp Tyr Ser
               185                 190                 195

Pro Glu Phe Leu Leu Trp Ala Leu Arg Pro Pro Gly Trp Leu Leu
               200                 205                 210

Gln Trp His Cys Gly Val Arg Val Ser Ser Asn Lys Lys Leu Val
               215                 220                 225

Gly Phe Ile Ser Ala Ile Pro Ala Asn Ile Arg Ile Tyr Asp Ser
               230                 235                 240

Val Lys Lys Met Val Glu Ile Asn Phe Leu Cys Val His Lys Lys
               245                 250                 255

Leu Arg Ser Lys Arg Val Ala Pro Val Leu Ile Arg Glu Ile Thr
               260                 265                 270

Arg Arg Val Asn Leu Glu Gly Ile Phe Gln Ala Val Tyr Thr Ala
               275                 280                 285

Gly Val Val Leu Pro Lys Pro Ile Ala Thr Cys Arg Tyr Trp His
               290                 295                 300

Arg Ser Leu Asn Pro Arg Lys Leu Val Glu Val Lys Phe Ser His
               305                 310                 315

Leu Ser Arg Asn Met Thr Leu Gln Arg Thr Met Lys Leu Tyr Arg
               320                 325                 330

Leu Pro Asp Val Thr Lys Thr Ser Gly Leu Arg Pro Met Glu Pro
               335                 340                 345

Lys Asp Ile Lys Ser Val Arg Glu Leu Ile Asn Thr Tyr Leu Lys
               350                 355                 360

Gln Phe His Leu Ala Pro Val Met Asp Glu Glu Val Ala His
               365                 370                 375

Trp Phe Leu Pro Arg Glu His Ile Ile Asp Thr Phe Val Val Glu
               380                 385                 390

Ser Pro Asn Gly Lys Leu Thr Asp Phe Leu Ser Phe Tyr Thr Leu
               395                 400                 405

Pro Ser Thr Val Met His His Pro Ala His Lys Ser Leu Lys Ala
               410                 415                 420

Ala Tyr Ser Phe Tyr Asn Ile His Thr Glu Thr Pro Leu Leu Asp
```

```
                        425                 430                 435
Leu Met Ser Asp Ala Leu Ile Leu Ala Lys Ser Lys Gly Phe Asp
                440                 445                 450

Val Phe Asn Ala Leu Asp Leu Met Glu Asn Lys Thr Phe Leu Glu
            455                 460                 465

Lys Leu Lys Phe Gly Ile Gly Asp Gly Asn Leu Gln Tyr Tyr Leu
        470                 475                 480

Tyr Asn Trp Arg Cys Pro Gly Thr Asp Ser Glu Lys Val Gly Leu
    485                 490                 495

Val Leu Gln

<210> SEQ ID NO 2
<211> LENGTH: 360
<212> TYPE: PRT
<213> ORGANISM: Homo sapiens
<220> FEATURE:
<221> NAME/KEY: misc_feature
<223> OTHER INFORMATION: Incyte ID No: 2682663CD1

<400> SEQUENCE: 2

Met Lys Ala Leu Ile Leu Val Gly Gly Tyr Gly Thr Arg Leu Arg
  1               5                  10                  15

Pro Leu Thr Leu Ser Thr Pro Lys Pro Leu Val Asp Phe Cys Asn
                 20                  25                  30

Lys Pro Ile Leu Leu His Gln Val Glu Ala Leu Ala Ala Ala Gly
             35                  40                  45

Val Asp His Val Ile Leu Ala Val Ser Tyr Met Ser Gln Val Leu
         50                  55                  60

Glu Lys Glu Met Lys Ala Gln Glu Gln Arg Leu Gly Ile Arg Ile
     65                  70                  75

Ser Met Ser His Glu Glu Glu Pro Leu Gly Thr Ala Gly Pro Leu
 80                  85                  90

Ala Leu Ala Arg Asp Leu Leu Ser Glu Thr Ala Asp Pro Phe Phe
             95                 100                 105

Val Leu Asn Ser Asp Val Ile Cys Asp Phe Pro Phe Gln Ala Met
            110                 115                 120

Val Gln Phe His Arg His His Gly Gln Glu Gly Ser Ile Leu Val
            125                 130                 135

Thr Lys Val Glu Glu Pro Ser Lys Tyr Gly Val Val Val Cys Glu
            140                 145                 150

Ala Asp Thr Gly Arg Ile His Arg Phe Val Glu Lys Pro Gln Val
            155                 160                 165

Phe Val Ser Asn Lys Ile Asn Ala Gly Met Tyr Ile Leu Ser Pro
            170                 175                 180

Ala Val Leu Arg Arg Ile Gln Leu Gln Pro Thr Ser Ile Glu Lys
            185                 190                 195

Glu Val Phe Pro Ile Met Ala Lys Glu Gly Gln Leu Tyr Ala Met
            200                 205                 210

Glu Leu Gln Gly Phe Trp Met Asp Ile Gly Gln Pro Lys Asp Phe
            215                 220                 225

Leu Thr Gly Met Cys Leu Phe Leu Gln Ser Leu Arg Gln Lys Gln
            230                 235                 240

Pro Glu Arg Leu Cys Ser Gly Pro Gly Ile Val Gly Asn Val Leu
            245                 250                 255

Val Asp Pro Ser Ala Arg Ile Gly Gln Asn Cys Ser Ile Gly Pro
```

```
                              260                 265                 270
Asn Val Ser Leu Gly Pro Gly Val Val Glu Asp Gly Val Cys
                  275                 280                 285
Ile Arg Arg Cys Thr Val Leu Arg Asp Ala Arg Ile Arg Ser His
              290                 295                 300
Ser Trp Leu Glu Ser Cys Ile Val Gly Trp Arg Cys Arg Val Gly
              305                 310                 315
Gln Trp Val Arg Met Glu Asn Val Thr Val Leu Gly Glu Asp Val
              320                 325                 330
Ile Val Asn Asp Glu Leu Tyr Leu Asn Gly Ala Ser Val Leu Pro
              335                 340                 345
His Lys Ser Ile Gly Glu Ser Val Pro Glu Pro Arg Ile Ile Met
              350                 355                 360

<210> SEQ ID NO 3
<211> LENGTH: 519
<212> TYPE: PRT
<213> ORGANISM: Homo sapiens
<220> FEATURE:
<221> NAME/KEY: misc_feature
<223> OTHER INFORMATION: Incyte ID No: 1265094CD1

<400> SEQUENCE: 3

Met Ala Glu Glu Arg Val Ala Thr Arg Thr Gln Phe Pro Val Ser
 1               5                  10                  15
Thr Glu Ser Gln Lys Pro Arg Gln Lys Lys Ala Pro Glu Phe Pro
              20                  25                  30
Ile Leu Glu Lys Gln Asn Trp Leu Ile His Leu His Tyr Ile Arg
              35                  40                  45
Lys Asp Tyr Glu Ala Cys Lys Ala Val Ile Lys Glu Gln Leu Gln
              50                  55                  60
Glu Thr Gln Gly Leu Cys Glu Tyr Ala Ile Tyr Val Gln Ala Leu
              65                  70                  75
Ile Phe Arg Leu Glu Gly Asn Ile Gln Glu Ser Leu Glu Leu Phe
              80                  85                  90
Gln Thr Cys Ala Val Leu Ser Pro Gln Ser Ala Asp Asn Leu Lys
              95                 100                 105
Gln Val Ala Arg Ser Leu Phe Leu Leu Gly Lys His Lys Ala Ala
             110                 115                 120
Ile Glu Val Tyr Asn Glu Ala Ala Lys Leu Asn Gln Lys Asp Trp
             125                 130                 135
Glu Ile Ser His Asn Leu Gly Val Cys Tyr Ile Tyr Leu Lys Gln
             140                 145                 150
Phe Asn Lys Ala Gln Asp Gln Leu His Asn Ala Leu Asn Leu Asn
             155                 160                 165
Arg His Asp Leu Thr Tyr Ile Met Leu Gly Lys Ile His Leu Leu
             170                 175                 180
Glu Gly Asp Leu Asp Lys Ala Ile Glu Val Tyr Lys Lys Ala Val
             185                 190                 195
Glu Phe Ser Pro Glu Asn Thr Glu Leu Leu Thr Thr Leu Gly Leu
             200                 205                 210
Leu Tyr Leu Gln Leu Gly Ile Tyr Gln Lys Ala Phe Glu His Leu
             215                 220                 225
Gly Asn Ala Leu Thr Tyr Asp Pro Thr Asn Tyr Lys Ala Ile Leu
             230                 235                 240
```

-continued

```
Ala Ala Gly Ser Met Met Gln Thr His Gly Asp Phe Asp Val Ala
            245                 250                 255

Leu Thr Lys Tyr Arg Val Val Ala Cys Ala Val Pro Glu Ser Pro
            260                 265                 270

Pro Leu Trp Asn Asn Ile Gly Met Cys Phe Phe Gly Lys Lys Lys
            275                 280                 285

Tyr Val Ala Ala Ile Ser Cys Leu Lys Arg Ala Asn Tyr Leu Ala
            290                 295                 300

Pro Phe Asp Trp Lys Ile Leu Tyr Asn Leu Gly Leu Val His Leu
            305                 310                 315

Thr Met Gln Gln Tyr Ala Ser Ala Phe His Phe Leu Ser Ala Ala
            320                 325                 330

Ile Asn Phe Gln Pro Lys Met Gly Glu Leu Tyr Met Leu Leu Ala
            335                 340                 345

Val Ala Leu Thr Asn Leu Glu Asp Thr Glu Asn Ala Lys Arg Ala
            350                 355                 360

Tyr Ala Glu Ala Val His Leu Asp Lys Cys Asn Pro Leu Val Asn
            365                 370                 375

Leu Asn Tyr Ala Val Leu Leu Tyr Asn Gln Gly Lys Lys Asn
            380                 385                 390

Ala Leu Ala Gln Tyr Gln Glu Met Glu Lys Lys Val Ser Leu Leu
            395                 400                 405

Lys Asp Asn Ser Ser Leu Glu Phe Asp Ser Glu Met Val Glu Met
            410                 415                 420

Ala Gln Lys Leu Gly Ala Ala Leu Gln Val Gly Glu Ala Leu Val
            425                 430                 435

Trp Thr Lys Pro Val Lys Asp Pro Lys Ser Lys His Gln Thr Thr
            440                 445                 450

Ser Thr Ser Lys Pro Ala Ser Phe Gln Gln Pro Leu Gly Ser Asn
            455                 460                 465

Gln Ala Leu Gly Gln Ala Met Ser Ser Ala Ala Ala Tyr Arg Thr
            470                 475                 480

Leu Pro Ser Gly Ala Gly Gly Thr Ser Gln Phe Thr Lys Pro Pro
            485                 490                 495

Ser Leu Pro Leu Glu Pro Glu Pro Ala Val Ser Ser Pro Thr
            500                 505                 510

Glu Thr Ser Glu Gln Ile Arg Glu Lys
            515

<210> SEQ ID NO 4
<211> LENGTH: 225
<212> TYPE: PRT
<213> ORGANISM: Homo sapiens
<220> FEATURE:
<221> NAME/KEY: misc_feature
<223> OTHER INFORMATION: Incyte ID No: 1404963CD1

<400> SEQUENCE: 4

Met Ala Gly Ser Ser Glu Glu Ala Pro Asp Tyr Gly Arg Gly Val
  1               5                  10                  15

Val Ile Met Asp Asp Trp Pro Gly Tyr Asp Leu Asn Leu Phe Thr
                 20                  25                  30

Tyr Pro Gln His Tyr Tyr Gly Asp Leu Glu Tyr Val Leu Ile Pro
                 35                  40                  45

His Gly Ile Ile Val Asp Arg Ile Glu Arg Leu Ala Lys Asp Ile
                 50                  55                  60
```

```
Met Lys Asp Ile Gly Tyr Ser Asp Ile Met Val Leu Cys Val Leu
                65                  70                  75

Lys Gly Gly Tyr Lys Phe Cys Ala Asp Leu Val Glu His Leu Lys
            80                  85                  90

Asn Ile Ser Arg Asn Ser Asp Arg Phe Val Ser Met Lys Val Asp
            95                 100                 105

Phe Ile Arg Leu Lys Ser Tyr Arg Asn Asp Gln Ser Met Gly Glu
           110                 115                 120

Met Gln Ile Ile Gly Gly Asp Leu Ser Thr Leu Ala Gly Lys
           125                 130                 135

Asn Val Leu Ile Val Glu Asp Val Val Gly Thr Gly Arg Thr Met
           140                 145                 150

Lys Ala Leu Leu Ser Asn Ile Glu Lys Tyr Arg Pro Asn Met Ile
           155                 160                 165

Lys Val Ala Ser Leu Leu Val Lys Arg Thr Ser Arg Ser Asp Gly
           170                 175                 180

Phe Arg Pro Asp Tyr Ala Gly Phe Glu Ile Pro Asn Leu Phe Val
           185                 190                 195

Val Gly Tyr Ala Leu Asp Tyr Asn Glu Tyr Phe Arg Asp Leu Asn
           200                 205                 210

His Ile Cys Val Ile Asn Glu His Gly Lys Glu Lys Tyr Arg Val
           215                 220                 225

<210> SEQ ID NO 5
<211> LENGTH: 338
<212> TYPE: PRT
<213> ORGANISM: Homo sapiens
<220> FEATURE:
<221> NAME/KEY: misc_feature
<223> OTHER INFORMATION: Incyte ID No: 1405058CD1

<400> SEQUENCE: 5

Met Ala Ala Ser Gln Val Leu Gly Glu Lys Ile Asn Ile Leu Ser
  1               5                  10                  15

Gly Glu Thr Val Lys Ala Gly Asp Arg Asp Pro Leu Gly Asn Asp
             20                  25                  30

Cys Pro Glu Gln Asp Arg Leu Pro Gln Arg Ser Trp Arg Gln Lys
             35                  40                  45

Cys Ala Ser Tyr Val Leu Ala Leu Arg Pro Trp Ser Phe Ser Ala
             50                  55                  60

Ser Leu Thr Pro Val Ala Leu Gly Ser Ala Leu Ala Tyr Arg Ser
             65                  70                  75

His Gly Val Leu Asp Pro Arg Leu Leu Val Gly Cys Ala Val Ala
             80                  85                  90

Val Leu Ala Val His Gly Ala Gly Asn Leu Val Asn Thr Tyr Tyr
             95                 100                 105

Asp Phe Ser Lys Gly Ile Asp His Lys Lys Ser Asp Asp Arg Thr
            110                 115                 120

Leu Val Asp Arg Ile Leu Glu Pro Gln Asp Val Val Arg Phe Gly
            125                 130                 135

Val Phe Leu Tyr Thr Leu Gly Cys Val Cys Ala Ala Cys Leu Tyr
            140                 145                 150

Tyr Leu Ser Pro Leu Lys Leu Glu His Leu Ala Leu Ile Tyr Phe
            155                 160                 165

Gly Gly Leu Ser Gly Ser Phe Leu Tyr Thr Gly Gly Ile Gly Phe
```

-continued

```
                170                 175                 180
Lys Tyr Val Ala Leu Gly Asp Leu Ile Ile Leu Ile Thr Phe Gly
            185                 190                 195
Pro Leu Ala Val Met Phe Ala Tyr Ala Ile Gln Val Gly Ser Leu
        200                 205                 210
Ala Ile Phe Pro Leu Val Tyr Ala Ile Pro Leu Ala Leu Ser Thr
    215                 220                 225
Glu Ala Ile Leu His Ser Asn Asn Thr Arg Asp Met Glu Ser Asp
230                 235                 240
Arg Glu Ala Gly Ile Val Thr Leu Ala Ile Leu Ile Gly Pro Thr
            245                 250                 255
Phe Ser Tyr Ile Leu Tyr Asn Thr Leu Leu Phe Leu Pro Tyr Leu
        260                 265                 270
Val Phe Ser Ile Leu Ala Thr His Cys Thr Ile Ser Leu Ala Leu
    275                 280                 285
Pro Leu Leu Thr Ile Pro Met Ala Phe Ser Leu Glu Arg Gln Phe
290                 295                 300
Arg Ser Gln Ala Phe Asn Lys Leu Pro Gln Arg Thr Ala Lys Leu
            305                 310                 315
Asn Leu Leu Leu Gly Leu Phe Tyr Val Phe Gly Ile Ile Leu Ala
        320                 325                 330
Pro Ala Gly Ser Leu Pro Lys Ile
            335

<210> SEQ ID NO 6
<211> LENGTH: 619
<212> TYPE: PRT
<213> ORGANISM: Homo sapiens
<220> FEATURE:
<221> NAME/KEY: misc_feature
<223> OTHER INFORMATION: Incyte ID No: 1420940CD1

<400> SEQUENCE: 6

Met Ser Gly Ile Lys Lys Gln Lys Thr Glu Asn Gln Gln Lys Ser
  1               5                  10                  15
Thr Asn Val Val Tyr Gln Ala His His Val Ser Arg Asn Lys Arg
                 20                  25                  30
Gly Gln Val Val Gly Thr Arg Gly Gly Phe Arg Gly Cys Thr Val
             35                  40                  45
Trp Leu Thr Gly Leu Ser Gly Ala Gly Lys Thr Thr Ile Ser Phe
         50                  55                  60
Ala Leu Glu Glu Tyr Leu Val Ser His Ala Ile Pro Cys Tyr Ser
     65                  70                  75
Leu Asp Gly Asp Asn Val Arg His Gly Leu Asn Arg Asn Leu Gly
 80                  85                  90
Ser Ser Pro Gly Asp Arg Glu Glu Asn Ile Arg Arg Ile Ala Glu
             95                 100                 105
Val Ala Lys Leu Phe Ala Asp Ala Gly Leu Val Cys Ile Thr Ser
        110                 115                 120
Phe Ile Ser Pro Phe Ala Lys Asp Arg Glu Asn Ala Arg Lys Ile
    125                 130                 135
His Glu Ser Ala Gly Leu Pro Phe Phe Glu Ile Phe Val Asp Ala
140                 145                 150
Pro Leu Asn Ile Cys Glu Ser Arg Asp Val Lys Gly Leu Tyr Lys
            155                 160                 165
```

```
Arg Ala Arg Ala Gly Glu Ile Lys Gly Phe Thr Gly Ile Asp Ser
                170                 175                 180

Asp Tyr Glu Lys Pro Glu Thr Pro Glu Arg Val Leu Lys Thr Asn
                185                 190                 195

Leu Ser Thr Val Ser Asp Cys Val His Gln Val Val Glu Leu Leu
                200                 205                 210

Gln Glu Gln Asn Ile Val Pro Tyr Thr Ile Ile Lys Asp Ile His
                215                 220                 225

Glu Leu Phe Val Pro Glu Asn Lys Leu Asp His Val Arg Ala Glu
                230                 235                 240

Ala Glu Thr Leu Pro Ser Leu Ser Ile Thr Lys Leu Asp Leu Gln
                245                 250                 255

Trp Val Gln Val Leu Ser Glu Gly Trp Ala Thr Pro Leu Lys Gly
                260                 265                 270

Phe Met Arg Glu Lys Glu Tyr Leu Gln Val Met His Phe Asp Thr
                275                 280                 285

Leu Leu Asp Gly Met Ala Leu Pro Asp Gly Val Ile Asn Met Ser
                290                 295                 300

Ile Pro Ile Val Leu Pro Val Ser Ala Glu Asp Lys Thr Arg Leu
                305                 310                 315

Glu Gly Cys Ser Lys Phe Val Leu Ala His Gly Gly Arg Arg Val
                320                 325                 330

Ala Ile Leu Arg Asp Ala Glu Phe Tyr Glu His Arg Lys Glu Glu
                335                 340                 345

Arg Cys Ser Arg Val Trp Gly Thr Thr Cys Thr Lys His Pro His
                350                 355                 360

Ile Lys Met Val Met Glu Ser Gly Asp Trp Leu Val Gly Gly Asp
                365                 370                 375

Leu Gln Val Leu Glu Lys Ile Arg Trp Asn Asp Gly Leu Asp Gln
                380                 385                 390

Tyr Arg Leu Thr Pro Leu Glu Leu Lys Gln Lys Cys Lys Glu Met
                395                 400                 405

Asn Ala Asp Ala Val Phe Ala Phe Gln Leu Arg Asn Pro Val His
                410                 415                 420

Asn Gly His Ala Leu Leu Met Gln Asp Thr Arg Arg Arg Leu Leu
                425                 430                 435

Glu Arg Gly Tyr Lys His Pro Val Leu Leu Leu His Pro Leu Gly
                440                 445                 450

Gly Trp Thr Lys Asp Asp Val Pro Leu Asp Trp Arg Met Lys
                455                 460                 465

Gln His Ala Ala Val Leu Glu Glu Gly Val Leu Asp Pro Lys Ser
                470                 475                 480

Thr Ile Val Ala Ile Phe Pro Ser Pro Met Leu Tyr Ala Gly Pro
                485                 490                 495

Thr Glu Val Gln Trp His Cys Arg Ser Arg Met Ile Ala Gly Ala
                500                 505                 510

Asn Phe Tyr Ile Val Gly Arg Asp Pro Ala Gly Met Pro His Pro
                515                 520                 525

Glu Thr Lys Lys Asp Leu Tyr Glu Pro Thr His Gly Gly Lys Val
                530                 535                 540

Leu Ser Met Ala Pro Gly Leu Thr Ser Val Glu Ile Ile Pro Phe
                545                 550                 555

Arg Val Ala Ala Tyr Asn Lys Ala Lys Lys Ala Met Asp Phe Tyr
```

```
                    560                 565                 570
Asp Pro Ala Arg His Asn Glu Phe Asp Phe Ile Ser Gly Thr Arg
                575                 580                 585

Met Arg Lys Leu Ala Arg Glu Gly Glu Asn Pro Pro Asp Gly Phe
                590                 595                 600

Met Ala Pro Lys Ala Trp Lys Val Leu Thr Asp Tyr Tyr Arg Ser
                605                 610                 615

Leu Glu Lys Asn

<210> SEQ ID NO 7
<211> LENGTH: 284
<212> TYPE: PRT
<213> ORGANISM: Homo sapiens
<220> FEATURE:
<221> NAME/KEY: misc_feature
<223> OTHER INFORMATION: Incyte ID No: 1784742CD1

<400> SEQUENCE: 7

Met Ala Glu Ser Glu Ala Glu Thr Pro Ser Thr Pro Gly Glu Phe
  1               5                  10                  15

Glu Ser Lys Tyr Phe Glu Phe His Gly Val Arg Leu Pro Pro Phe
                 20                  25                  30

Cys Arg Gly Lys Met Glu Glu Ile Ala Asn Phe Pro Val Arg Pro
                 35                  40                  45

Ser Asp Val Trp Ile Val Thr Tyr Pro Lys Ser Gly Thr Ser Leu
                 50                  55                  60

Leu Gln Glu Val Val Tyr Leu Val Ser Gln Gly Ala Asp Pro Asp
                 65                  70                  75

Glu Ile Gly Leu Met Asn Ile Asp Glu Gln Leu Pro Val Leu Glu
                 80                  85                  90

Tyr Pro Gln Pro Gly Leu Asp Ile Ile Lys Glu Leu Thr Ser Pro
                 95                 100                 105

Arg Leu Ile Lys Ser His Leu Pro Tyr Arg Phe Leu Pro Ser Asp
                110                 115                 120

Leu His Asn Gly Asp Ser Lys Val Ile Tyr Met Ala Arg Asn Pro
                125                 130                 135

Lys Asp Leu Val Val Ser Tyr Tyr Gln Phe His Arg Ser Leu Arg
                140                 145                 150

Thr Met Ser Tyr Arg Gly Thr Phe Gln Glu Phe Cys Arg Arg Phe
                155                 160                 165

Met Asn Asp Lys Leu Gly Tyr Gly Ser Trp Phe Glu His Val Gln
                170                 175                 180

Glu Phe Trp Glu His Arg Met Asp Ser Asn Val Leu Phe Leu Lys
                185                 190                 195

Tyr Glu Asp Met His Arg Asp Leu Val Thr Met Val Glu Gln Leu
                200                 205                 210

Ala Arg Phe Leu Gly Val Ser Cys Asp Lys Ala Gln Leu Glu Ala
                215                 220                 225

Leu Thr Glu His Cys His Gln Leu Val Asp Gln Cys Asn Ala
                230                 235                 240

Glu Ala Leu Pro Val Gly Arg Gly Arg Val Gly Leu Trp Lys Asp
                245                 250                 255

Ile Phe Thr Val Ser Met Asn Glu Lys Phe Asp Leu Val Tyr Lys
                260                 265                 270

Gln Lys Met Gly Lys Cys Asp Leu Thr Phe Asp Phe Tyr Leu
```

```
                            275                 280

<210> SEQ ID NO 8
<211> LENGTH: 205
<212> TYPE: PRT
<213> ORGANISM: Homo sapiens
<220> FEATURE:
<221> NAME/KEY: misc_feature
<223> OTHER INFORMATION: Incyte ID No: 1967138CD1

<400> SEQUENCE: 8

Met Ala Asp Phe Cys Val Met Thr Arg Leu Leu Gly Tyr Val Asp
 1               5                  10                  15

Pro Leu Asp Pro Ser Phe Val Ala Val Ile Thr Ile Thr Phe
                20                  25                  30

Asn Pro Leu Tyr Trp Asn Val Val Ala Arg Trp Glu His Lys Thr
                35                  40                  45

Arg Lys Leu Ser Arg Ala Phe Gly Ser Pro Tyr Leu Ala Cys Tyr
                50                  55                  60

Ser Leu Ser Val Thr Ile Leu Leu Leu Asn Phe Leu Arg Ser His
                65                  70                  75

Cys Phe Thr Gln Ala Met Leu Ser Gln Pro Arg Met Glu Ser Leu
                80                  85                  90

Asp Thr Pro Ala Ala Tyr Ser Leu Gly Leu Ala Leu Leu Gly Leu
                95                 100                 105

Gly Val Val Leu Val Leu Ser Ser Phe Ala Leu Gly Phe Ala
                110                115                 120

Gly Thr Phe Leu Gly Asp Tyr Phe Gly Ile Leu Lys Glu Ala Arg
                125                130                 135

Val Thr Val Phe Pro Phe Asn Ile Leu Asp Asn Pro Met Tyr Trp
                140                145                 150

Gly Ser Thr Ala Asn Tyr Leu Gly Trp Ala Ile Met His Ala Ser
                155                160                 165

Pro Thr Gly Leu Leu Thr Val Leu Ala Leu Thr Tyr Ile
                170                175                 180

Val Ala Leu Leu Tyr Glu Glu Pro Phe Thr Ala Glu Ile Tyr Arg
                185                190                 195

Gln Lys Ala Ser Gly Ser His Lys Arg Ser
                200                205

<210> SEQ ID NO 9
<211> LENGTH: 414
<212> TYPE: PRT
<213> ORGANISM: Homo sapiens
<220> FEATURE:
<221> NAME/KEY: misc_feature
<223> OTHER INFORMATION: Incyte ID No: 2124351CD1

<400> SEQUENCE: 9

Met Thr Lys Ala Arg Leu Phe Arg Leu Trp Val Leu Gly Ser
 1               5                  10                  15

Val Phe Met Ile Leu Leu Ile Ile Val Tyr Trp Asp Ser Ala Gly
                20                  25                  30

Ala Ala His Phe Tyr Leu His Thr Ser Phe Ser Arg Pro His Thr
                35                  40                  45

Gly Pro Pro Leu Pro Thr Pro Gly Pro Asp Arg Asp Arg Glu Leu
                50                  55                  60

Thr Ala Asp Ser Asp Val Asp Glu Phe Leu Asp Lys Phe Leu Ser
```

```
                        65                  70                  75
Ala Gly Val Lys Gln Ser Asp Leu Pro Arg Lys Glu Thr Glu Gln
                80                  85                  90

Pro Pro Ala Pro Gly Ser Met Glu Glu Ser Val Arg Gly Tyr Asp
                95                 100                 105

Trp Ser Pro Arg Asp Ala Arg Arg Ser Pro Asp Gln Gly Arg Gln
               110                 115                 120

Gln Ala Glu Arg Ser Val Leu Arg Gly Phe Cys Ala Asn Ser
               125                 130                 135

Ser Leu Ala Phe Pro Thr Lys Glu Arg Ala Phe Asp Asp Ile Pro
               140                 145                 150

Asn Ser Glu Leu Ser His Leu Ile Val Asp Asp Arg His Gly Ala
               155                 160                 165

Ile Tyr Cys Tyr Val Pro Lys Val Ala Cys Thr Asn Trp Lys Arg
               170                 175                 180

Val Met Ile Val Leu Ser Gly Ser Leu Leu His Arg Gly Ala Pro
               185                 190                 195

Tyr Arg Asp Pro Leu Arg Ile Pro Arg Glu His Val His Asn Ala
               200                 205                 210

Ser Ala His Leu Thr Phe Asn Lys Phe Trp Arg Arg Tyr Gly Lys
               215                 220                 225

Leu Ser Arg His Leu Met Lys Val Lys Leu Lys Lys Tyr Thr Lys
               230                 235                 240

Phe Leu Phe Val Arg Asp Pro Phe Val Arg Leu Ile Ser Ala Phe
               245                 250                 255

Arg Ser Lys Phe Glu Leu Glu Asn Glu Glu Phe Tyr Arg Lys Phe
               260                 265                 270

Ala Val Pro Met Leu Arg Leu Tyr Ala Asn His Thr Ser Leu Pro
               275                 280                 285

Ala Ser Ala Arg Glu Ala Phe Arg Ala Gly Leu Lys Val Ser Phe
               290                 295                 300

Ala Asn Phe Ile Gln Tyr Leu Leu Asp Pro His Thr Glu Lys Leu
               305                 310                 315

Ala Pro Phe Asn Glu His Trp Arg Gln Val Tyr Arg Leu Cys His
               320                 325                 330

Pro Cys Gln Ile Asp Tyr Asp Phe Val Gly Lys Leu Glu Thr Leu
               335                 340                 345

Asp Glu Asp Ala Ala Gln Leu Leu Gln Leu Leu Gln Val Asp Arg
               350                 355                 360

Gln Leu Arg Phe Pro Pro Ser Tyr Arg Asn Arg Thr Ala Ser Ser
               365                 370                 375

Trp Glu Glu Asp Trp Phe Ala Lys Ile Pro Leu Ala Trp Arg Gln
               380                 385                 390

Gln Leu Tyr Lys Leu Tyr Glu Ala Asp Phe Val Leu Phe Gly Tyr
               395                 400                 405

Pro Lys Pro Glu Asn Leu Leu Arg Asp
               410

<210> SEQ ID NO 10
<211> LENGTH: 660
<212> TYPE: PRT
<213> ORGANISM: Homo sapiens
<220> FEATURE:
<221> NAME/KEY: misc_feature
<223> OTHER INFORMATION: Incyte ID No: 2153162CD1
```

<400> SEQUENCE: 10

```
Met Asp Asp Trp Lys Pro Ser Pro Leu Ile Lys Pro Phe Gly Ala
  1               5                  10                  15

Arg Lys Lys Arg Ser Trp Tyr Leu Thr Trp Lys Tyr Lys Leu Thr
                 20                  25                  30

Asn Gln Arg Ala Leu Arg Arg Phe Cys Gln Thr Gly Ala Val Leu
                 35                  40                  45

Phe Leu Leu Val Thr Val Ile Val Asn Ile Lys Leu Ile Leu Asp
                 50                  55                  60

Thr Arg Arg Ala Ile Ser Glu Ala Asn Glu Asp Pro Glu Pro Glu
 65                              70                      75

Gln Asp Tyr Asp Glu Ala Leu Gly Arg Leu Glu Pro Pro Arg Arg
                 80                  85                  90

Arg Gly Ser Gly Pro Arg Arg Val Leu Asp Val Glu Val Tyr Ser
                 95                 100                 105

Ser Arg Ser Lys Val Tyr Val Ala Val Asp Gly Thr Thr Val Leu
                110                 115                 120

Glu Asp Glu Ala Arg Glu Gln Gly Arg Gly Ile His Val Ile Val
                125                 130                 135

Leu Asn Gln Ala Thr Gly His Val Met Ala Lys Arg Val Phe Asp
                140                 145                 150

Thr Tyr Ser Pro His Glu Asp Glu Ala Met Val Leu Phe Leu Asn
                155                 160                 165

Met Val Ala Pro Gly Arg Val Leu Ile Cys Thr Val Lys Asp Glu
                170                 175                 180

Gly Ser Phe His Leu Lys Asp Thr Ala Lys Ala Leu Leu Arg Ser
                185                 190                 195

Leu Gly Ser Gln Ala Gly Pro Ala Leu Gly Trp Arg Asp Thr Trp
                200                 205                 210

Ala Phe Val Gly Arg Lys Gly Gly Pro Val Phe Gly Glu Lys His
                215                 220                 225

Ser Lys Ser Pro Ala Leu Ser Ser Trp Gly Asp Pro Val Leu Leu
                230                 235                 240

Lys Thr Asp Val Pro Leu Ser Ser Ala Glu Glu Ala Glu Cys His
                245                 250                 255

Trp Ala Asp Thr Glu Leu Asn Arg Arg Arg Arg Arg Phe Cys Ser
                260                 265                 270

Lys Val Glu Gly Tyr Gly Ser Val Cys Ser Cys Lys Asp Pro Thr
                275                 280                 285

Pro Ile Glu Phe Ser Pro Asp Pro Leu Pro Asp Asn Lys Val Leu
                290                 295                 300

Asn Val Pro Val Ala Val Ile Ala Gly Asn Arg Pro Asn Tyr Leu
                305                 310                 315

Tyr Arg Met Leu Arg Ser Leu Leu Ser Ala Gln Gly Val Ser Pro
                320                 325                 330

Gln Met Ile Thr Val Phe Ile Asp Gly Tyr Tyr Glu Glu Pro Met
                335                 340                 345

Asp Val Val Ala Leu Phe Gly Leu Arg Gly Ile Gln His Thr Pro
                350                 355                 360

Ile Ser Ile Lys Asn Ala Arg Val Ser Gln His Tyr Lys Ala Ser
                365                 370                 375

Leu Thr Ala Thr Phe Asn Leu Phe Pro Glu Ala Lys Phe Ala Val
```

-continued

```
                    380                 385                 390

Val Leu Glu Glu Asp Leu Asp Ile Ala Val Asp Phe Phe Ser Phe
                395                 400                 405

Leu Ser Gln Ser Ile His Leu Leu Glu Glu Asp Asp Ser Leu Tyr
                410                 415                 420

Cys Ile Ser Ala Trp Asn Asp Gln Gly Tyr Glu His Thr Ala Glu
                425                 430                 435

Asp Pro Ala Leu Leu Tyr Arg Val Glu Thr Met Pro Gly Leu Gly
                440                 445                 450

Trp Val Leu Arg Arg Ser Leu Tyr Lys Glu Glu Leu Glu Pro Lys
                455                 460                 465

Trp Pro Thr Pro Glu Lys Leu Trp Asp Trp Asp Met Trp Met Arg
                470                 475                 480

Met Pro Glu Gln Arg Arg Gly Arg Glu Cys Ile Ile Pro Asp Val
                485                 490                 495

Ser Arg Ser Tyr His Phe Gly Ile Val Gly Leu Asn Met Asn Gly
                500                 505                 510

Tyr Phe His Glu Ala Tyr Phe Lys Lys His Lys Phe Asn Thr Val
                515                 520                 525

Pro Gly Val Gln Leu Arg Asn Val Asp Ser Leu Lys Lys Glu Ala
                530                 535                 540

Tyr Glu Val Glu Val His Arg Leu Leu Ser Glu Ala Glu Val Leu
                545                 550                 555

Asp His Ser Lys Asn Pro Cys Glu Asp Ser Phe Leu Pro Asp Thr
                560                 565                 570

Glu Gly His Thr Tyr Val Ala Phe Ile Arg Met Glu Lys Asp Asp
                575                 580                 585

Asp Phe Thr Thr Trp Thr Gln Leu Ala Lys Cys Leu His Ile Trp
                590                 595                 600

Asp Leu Asp Val Arg Gly Asn His Arg Gly Leu Trp Arg Leu Phe
                605                 610                 615

Arg Lys Lys Asn His Phe Leu Val Val Gly Val Pro Ala Ser Pro
                620                 625                 630

Tyr Ser Val Lys Lys Pro Pro Ser Val Thr Pro Ile Phe Leu Glu
                635                 640                 645

Pro Pro Pro Lys Glu Glu Gly Ala Pro Gly Ala Pro Glu Gln Thr
                650                 655                 660

<210> SEQ ID NO 11
<211> LENGTH: 386
<212> TYPE: PRT
<213> ORGANISM: Homo sapiens
<220> FEATURE:
<221> NAME/KEY: misc_feature
<223> OTHER INFORMATION: Incyte ID No: 2617407CD1

<400> SEQUENCE: 11

Met Leu Leu Pro Lys Lys Met Lys Leu Leu Phe Leu Val Ser
  1               5                  10                  15

Gln Met Ala Ile Leu Ala Leu Phe Phe His Met Tyr Ser His Asn
                 20                  25                  30

Ile Ser Ser Leu Ser Met Lys Ala Gln Pro Glu Arg Met His Val
                 35                  40                  45

Leu Val Leu Ser Ser Trp Arg Ser Gly Ser Ser Phe Val Gly Gln
                 50                  55                  60
```

```
Leu Phe Gly Gln His Pro Asp Val Phe Tyr Leu Met Glu Pro Ala
                65                  70                  75

Trp His Val Trp Met Thr Phe Lys Gln Ser Thr Ala Trp Met Leu
            80                  85                  90

His Met Ala Val Arg Asp Leu Ile Arg Ala Val Phe Leu Cys Asp
        95                  100                 105

Met Ser Val Phe Asp Ala Tyr Met Glu Pro Gly Pro Arg Arg Gln
    110                 115                 120

Ser Ser Leu Phe Gln Trp Glu Asn Ser Arg Ala Leu Cys Ser Ala
125                 130                 135

Pro Ala Cys Asp Ile Ile Pro Gln Asp Glu Ser Ser Pro Gly Leu
                140                 145                 150

Thr Ala Gly Ser Cys Ala Val Asn Ser Pro Leu Lys Leu Leu Glu
            155                 160                 165

Lys Ala Cys Arg Ser Tyr Ser His Val Val Leu Lys Glu Val Arg
        170                 175                 180

Phe Phe Asn Leu Gln Ser Leu Tyr Pro Leu Leu Lys Asp Pro Ser
    185                 190                 195

Leu Asn Leu His Ile Val His Leu Val Arg Asp Pro Arg Ala Val
200                 205                 210

Phe Arg Ser Arg Glu Arg Thr Lys Gly Asp Leu Met Ile Asp Ser
                215                 220                 225

Arg Ile Val Met Gly Gln His Glu Gln Lys Leu Lys Lys Glu Asp
            230                 235                 240

Gln Pro Tyr Tyr Val Met Gln Val Ile Cys Gln Ser Gln Leu Glu
        245                 250                 255

Ile Tyr Lys Thr Ile Gln Ser Leu Pro Lys Ala Leu Gln Glu Arg
    260                 265                 270

Tyr Leu Leu Val Arg Tyr Glu Asp Leu Ala Arg Ala Pro Val Ala
275                 280                 285

Gln Thr Ser Arg Met Tyr Glu Phe Val Gly Leu Glu Phe Leu Pro
                290                 295                 300

His Leu Gln Thr Trp Val His Asn Ile Thr Arg Gly Lys Gly Met
            305                 310                 315

Gly Asp His Ala Phe His Thr Asn Ala Arg Asp Ala Leu Asn Val
        320                 325                 330

Ser Gln Ala Trp Arg Trp Ser Leu Pro Tyr Glu Lys Val Ser Arg
    335                 340                 345

Leu Gln Lys Ala Cys Gly Asp Ala Met Asn Leu Leu Gly Tyr Arg
350                 355                 360

His Val Arg Ser Glu Gln Glu Gln Arg Asn Leu Leu Leu Asp Leu
                365                 370                 375

Leu Ser Thr Trp Thr Val Pro Glu Gln Ile His
            380                 385

<210> SEQ ID NO 12
<211> LENGTH: 803
<212> TYPE: PRT
<213> ORGANISM: Homo sapiens
<220> FEATURE:
<221> NAME/KEY: misc_feature
<223> OTHER INFORMATION: Incyte ID No: 2963717CD1

<400> SEQUENCE: 12

Met Ala Glu Ala His Gln Ala Val Gly Phe Arg Pro Ser Leu Thr
1               5                   10                  15
```

-continued

```
Ser Asp Gly Ala Glu Val Glu Leu Ser Ala Pro Val Leu Gln Glu
            20                  25                  30

Ile Tyr Leu Ser Gly Leu Arg Ser Trp Lys Arg His Leu Ser Arg
            35                  40                  45

Phe Trp Asn Asp Phe Leu Thr Gly Val Phe Pro Ala Ser Pro Leu
            50                  55                  60

Ser Trp Leu Phe Leu Phe Ser Ala Ile Gln Leu Ala Trp Phe Leu
            65                  70                  75

Gln Leu Asp Pro Ser Leu Gly Leu Met Glu Lys Ile Lys Glu Leu
            80                  85                  90

Leu Pro Asp Trp Gly Gly Gln His His Gly Leu Arg Gly Val Leu
            95                 100                 105

Ala Ala Ala Leu Phe Ala Ser Cys Leu Trp Gly Ala Leu Ile Phe
           110                 115                 120

Thr Leu His Val Ala Leu Arg Leu Leu Leu Ser Tyr His Gly Trp
           125                 130                 135

Leu Leu Glu Pro His Gly Ala Met Ser Ser Pro Thr Lys Thr Trp
           140                 145                 150

Leu Ala Leu Val Arg Ile Phe Ser Gly Arg His Pro Met Leu Phe
           155                 160                 165

Ser Tyr Gln Arg Ser Leu Pro Arg Gln Pro Val Pro Ser Val Gln
           170                 175                 180

Asp Thr Val Arg Lys Tyr Leu Glu Ser Val Arg Pro Ile Leu Ser
           185                 190                 195

Asp Glu Asp Phe Asp Trp Thr Ala Val Leu Ala Gln Glu Phe Leu
           200                 205                 210

Arg Leu Gln Ala Ser Leu Leu Gln Trp Tyr Leu Arg Leu Lys Ser
           215                 220                 225

Trp Trp Ala Ser Asn Tyr Val Ser Asp Trp Trp Glu Glu Phe Val
           230                 235                 240

Tyr Leu Arg Ser Arg Asn Pro Leu Met Val Asn Ser Asn Tyr Tyr
           245                 250                 255

Met Met Asp Phe Leu Tyr Val Thr Pro Thr Pro Leu Gln Ala Ala
           260                 265                 270

Arg Ala Gly Asn Ala Val His Ala Leu Leu Leu Tyr Arg His Arg
           275                 280                 285

Leu Asn Arg Gln Glu Ile Pro Pro Thr Leu Leu Met Gly Met Arg
           290                 295                 300

Pro Leu Cys Ser Ala Gln Tyr Glu Lys Ile Phe Asn Thr Thr Arg
           305                 310                 315

Ile Pro Gly Val Gln Lys Asp Tyr Ile Arg His Leu His Asp Ser
           320                 325                 330

Gln His Val Ala Val Phe His Arg Gly Arg Phe Phe Arg Met Gly
           335                 340                 345

Thr His Ser Arg Asn Ser Leu Leu Ser Pro Arg Ala Leu Glu Gln
           350                 355                 360

Gln Phe Gln Arg Ile Leu Asp Asp Pro Ser Pro Ala Cys Pro His
           365                 370                 375

Glu Glu His Leu Ala Ala Leu Thr Ala Ala Pro Arg Gly Thr Trp
           380                 385                 390

Ala Gln Val Arg Thr Ser Leu Lys Thr Gln Ala Ala Glu Ala Leu
           395                 400                 405
```

```
Glu Ala Val Glu Gly Ala Ala Phe Phe Val Ser Leu Asp Ala Glu
                410                 415                 420

Pro Ala Gly Leu Thr Arg Glu Asp Pro Ala Ala Ser Leu Asp Ala
                425                 430                 435

Tyr Ala His Ala Leu Leu Ala Gly Arg Gly His Asp Arg Trp Phe
                440                 445                 450

Asp Lys Ser Phe Thr Leu Ile Val Phe Ser Asn Gly Lys Leu Gly
                455                 460                 465

Leu Ser Val Glu His Ser Trp Ala Asp Cys Pro Ile Ser Gly His
                470                 475                 480

Met Trp Glu Phe Thr Leu Ala Thr Glu Cys Phe Gln Leu Gly Tyr
                485                 490                 495

Ser Thr Asp Gly His Cys Lys Gly His Pro Asp Pro Thr Leu Pro
                500                 505                 510

Gln Pro Gln Arg Leu Gln Trp Asp Leu Pro Asp Gln Ile His Ser
                515                 520                 525

Ser Ile Ser Leu Ala Leu Arg Gly Ala Lys Ile Leu Ser Glu Asn
                530                 535                 540

Val Asp Cys His Val Val Pro Phe Ser Leu Phe Gly Lys Ser Phe
                545                 550                 555

Ile Arg Arg Cys His Leu Ser Ser Asp Ser Phe Ile Gln Ile Ala
                560                 565                 570

Leu Gln Leu Ala His Phe Arg Asp Arg Gly Gln Phe Cys Leu Thr
                575                 580                 585

Tyr Glu Ser Ala Met Thr Arg Leu Phe Leu Glu Gly Arg Thr Glu
                590                 595                 600

Thr Val Arg Ser Cys Thr Arg Glu Ala Cys Asn Phe Val Arg Ala
                605                 610                 615

Met Glu Asp Lys Glu Lys Thr Asp Pro Gln Cys Leu Ala Leu Phe
                620                 625                 630

Arg Val Ala Val Asp Lys His Gln Ala Leu Leu Lys Ala Ala Met
                635                 640                 645

Ser Gly Gln Gly Val Asp Arg His Leu Phe Ala Leu Tyr Ile Val
                650                 655                 660

Ser Arg Phe Leu His Leu Gln Ser Pro Phe Leu Thr Gln Val His
                665                 670                 675

Ser Glu Gln Trp Gln Leu Ser Thr Ser Gln Ile Pro Val Gln Gln
                680                 685                 690

Met His Leu Phe Asp Val His Asn Tyr Pro Asp Tyr Val Ser Ser
                695                 700                 705

Gly Gly Gly Phe Gly Pro Ala Asp Asp His Gly Tyr Gly Val Ser
                710                 715                 720

Tyr Ile Phe Met Gly Asp Gly Met Ile Thr Phe His Ile Ser Ser
                725                 730                 735

Lys Lys Ser Ser Thr Lys Thr Asp Ser His Arg Leu Gly Gln His
                740                 745                 750

Ile Glu Asp Ala Leu Leu Asp Val Ala Ser Leu Phe Gln Ala Gly
                755                 760                 765

Gln His Phe Lys Arg Arg Phe Arg Gly Ser Gly Lys Glu Asn Ser
                770                 775                 780

Arg His Arg Cys Gly Phe Leu Ser Arg Gln Thr Gly Ala Ser Lys
                785                 790                 795

Ala Ser Met Thr Ser Thr Asp Phe
```

-continued

```
                                    800

<210> SEQ ID NO 13
<211> LENGTH: 295
<212> TYPE: PRT
<213> ORGANISM: Homo sapiens
<220> FEATURE:
<221> NAME/KEY: misc_feature
<223> OTHER INFORMATION: Incyte ID No: 3360857CD1

<400> SEQUENCE: 13
```

Met Val Asp Ser Val Tyr Arg Thr Arg Ser Leu Gly Val Ala Ala
 1               5                  10                  15

Glu Gly Leu Pro Asp Gln Tyr Ala Asp Gly Glu Ala Ala Arg Val
                20                  25                  30

Trp Gln Leu Tyr Ile Gly Asp Thr Arg Ser Arg Thr Ala Glu Tyr
                35                  40                  45

Lys Ala Trp Leu Leu Gly Leu Leu Arg Gln His Gly Cys Gln Arg
                50                  55                  60

Val Leu Asp Val Ala Cys Gly Thr Gly Val Asp Ser Ile Met Leu
                65                  70                  75

Val Glu Glu Gly Phe Ser Val Thr Ser Val Asp Ala Ser Asp Lys
                80                  85                  90

Met Leu Lys Tyr Ala Leu Lys Glu Arg Trp Asn Arg Arg His Glu
                95                  100                 105

Pro Ala Phe Asp Lys Trp Val Ile Glu Glu Ala Asn Trp Met Thr
                110                 115                 120

Leu Asp Lys Asp Val Pro Gln Ser Ala Glu Gly Gly Phe Asp Ala
                125                 130                 135

Val Ile Cys Leu Gly Asn Ser Phe Ala His Leu Pro Asp Cys Lys
                140                 145                 150

Gly Asp Gln Ser Glu His Arg Leu Ala Leu Lys Asn Ile Ala Ser
                155                 160                 165

Met Val Arg Ala Gly Gly Leu Leu Val Ile Asp His Arg Asn Tyr
                170                 175                 180

Asp His Ile Leu Ser Thr Gly Cys Ala Pro Pro Gly Lys Asn Ile
                185                 190                 195

Tyr Tyr Lys Ser Asp Leu Thr Lys Asp Val Thr Thr Ser Val Leu
                200                 205                 210

Ile Val Asn Asn Lys Ala His Met Val Thr Leu Asp Tyr Thr Val
                215                 220                 225

Gln Val Pro Gly Ala Gly Gln Asp Gly Ser Pro Gly Leu Ser Lys
                230                 235                 240

Phe Arg Leu Ser Tyr Tyr Pro His Cys Leu Ala Ser Phe Thr Glu
                245                 250                 255

Leu Leu Gln Ala Ala Phe Gly Gly Lys Cys Gln His Ser Val Leu
                260                 265                 270

Gly Asp Phe Lys Pro Tyr Lys Pro Gly Gln Thr Tyr Ile Pro Cys
                275                 280                 285

Tyr Phe Ile His Val Leu Lys Arg Thr Asp
                290                 295

```
<210> SEQ ID NO 14
<211> LENGTH: 575
<212> TYPE: PRT
<213> ORGANISM: Homo sapiens
<220> FEATURE:
```

-continued

```
<221> NAME/KEY: misc_feature
<223> OTHER INFORMATION: Incyte ID No: 3449671CD1

<400> SEQUENCE: 14

Met Thr Ser Lys Lys Leu Val Asn Ser Val Ala Gly Cys Ala Asp
  1               5                  10                  15

Asp Ala Leu Ala Gly Leu Val Ala Cys Asn Pro Asn Leu Gln Leu
                 20                  25                  30

Leu Gln Gly His Arg Val Ala Leu Arg Ser Asp Leu Asp Ser Leu
                 35                  40                  45

Lys Gly Arg Val Ala Leu Leu Ser Gly Gly Gly Ser Gly His Glu
                 50                  55                  60

Pro Ala His Ala Gly Phe Ile Gly Lys Gly Met Leu Thr Gly Val
                 65                  70                  75

Ile Ala Gly Ala Val Phe Thr Ser Pro Ala Val Gly Ser Ile Leu
                 80                  85                  90

Ala Ala Ile Arg Ala Val Ala Gln Ala Gly Thr Val Gly Thr Leu
                 95                 100                 105

Leu Ile Val Lys Asn Tyr Thr Gly Asp Arg Leu Asn Phe Gly Leu
                110                 115                 120

Ala Arg Glu Gln Ala Arg Ala Glu Gly Ile Pro Val Glu Met Val
                125                 130                 135

Val Ile Gly Asp Asp Ser Ala Phe Thr Val Leu Lys Lys Ala Gly
                140                 145                 150

Arg Arg Gly Leu Cys Gly Thr Val Leu Ile His Lys Val Ala Gly
                155                 160                 165

Ala Leu Ala Glu Ala Gly Val Gly Leu Glu Glu Ile Ala Lys Gln
                170                 175                 180

Val Asn Val Val Thr Lys Ala Met Gly Thr Leu Gly Val Ser Leu
                185                 190                 195

Ser Ser Cys Ser Val Pro Gly Ser Lys Pro Thr Phe Glu Leu Ser
                200                 205                 210

Ala Asp Glu Val Glu Leu Gly Leu Gly Ile His Gly Glu Ala Gly
                215                 220                 225

Val Arg Arg Ile Lys Met Ala Thr Ala Asp Glu Ile Val Lys Leu
                230                 235                 240

Met Leu Asp His Met Thr Asn Thr Thr Asn Ala Ser His Val Pro
                245                 250                 255

Val Gln Pro Gly Ser Ser Val Val Met Met Val Asn Asn Leu Gly
                260                 265                 270

Gly Leu Ser Phe Leu Glu Leu Gly Ile Ile Ala Asp Ala Thr Val
                275                 280                 285

Arg Ser Leu Glu Gly Arg Gly Val Lys Ile Ala Arg Ala Leu Val
                290                 295                 300

Gly Thr Phe Met Ser Ala Leu Glu Met Pro Gly Ile Ser Leu Thr
                305                 310                 315

Leu Leu Leu Val Asp Glu Pro Leu Leu Lys Leu Ile Asp Ala Glu
                320                 325                 330

Thr Thr Ala Ala Ala Trp Pro Asn Val Ala Ala Val Ser Ile Thr
                335                 340                 345

Gly Arg Lys Arg Ser Arg Val Ala Pro Ala Glu Pro Gln Glu Ala
                350                 355                 360

Pro Asp Ser Thr Ala Ala Gly Gly Ser Ala Ser Lys Arg Met Ala
                365                 370                 375
```

```
Leu Val Leu Glu Arg Val Cys Ser Thr Leu Leu Gly Leu Glu Glu
                380                 385                 390

His Leu Asn Ala Leu Asp Arg Ala Ala Gly Asp Gly Asp Cys Gly
                395                 400                 405

Thr Thr His Ser Arg Ala Ala Arg Ala Ile Gln Glu Trp Leu Lys
                410                 415                 420

Glu Gly Pro Pro Ala Ser Pro Ala Gln Leu Leu Ser Lys Leu
                425                 430                 435

Ser Val Leu Leu Leu Glu Lys Met Gly Gly Ser Ser Gly Ala Leu
                440                 445                 450

Tyr Gly Leu Phe Leu Thr Ala Ala Gln Pro Leu Lys Ala Lys
                455                 460                 465

Thr Ser Leu Pro Ala Trp Ser Ala Ala Met Asp Ala Gly Leu Glu
                470                 475                 480

Ala Met Gln Lys Tyr Gly Lys Ala Ala Pro Gly Asp Arg Thr Met
                485                 490                 495

Leu Asp Ser Leu Trp Ala Ala Gly Gln Glu Leu Gln Ala Trp Lys
                500                 505                 510

Ser Pro Gly Ala Asp Leu Leu Gln Val Leu Thr Lys Ala Val Lys
                515                 520                 525

Ser Ala Glu Ala Ala Ala Glu Ala Thr Lys Asn Met Glu Ala Gly
                530                 535                 540

Ala Gly Arg Ala Ser Tyr Ile Ser Ser Ala Arg Leu Glu Gln Pro
                545                 550                 555

Asp Pro Gly Ala Val Ala Ala Ala Ile Leu Arg Ala Ile Leu
                560                 565                 570

Glu Val Leu Gln Ser
                575

<210> SEQ ID NO 15
<211> LENGTH: 180
<212> TYPE: PRT
<213> ORGANISM: Homo sapiens
<220> FEATURE:
<221> NAME/KEY: misc_feature
<223> OTHER INFORMATION: Incyte ID No: 5497787CD1

<400> SEQUENCE: 15

Met Ala Ser Ser Val Gly Asn Val Ala Asp Ser Thr Glu Pro Thr
  1               5                  10                  15

Lys Arg Met Leu Ser Phe Gln Gly Leu Ala Glu Leu Ala His Arg
                 20                  25                  30

Glu Tyr Gln Ala Gly Asp Phe Glu Ala Ala Glu Arg His Cys Met
                 35                  40                  45

Gln Leu Trp Arg Gln Glu Pro Asp Asn Thr Gly Val Leu Leu Leu
                 50                  55                  60

Leu Ser Ser Ile His Phe Gln Cys Arg Arg Leu Asp Arg Ser Ala
                 65                  70                  75

His Phe Ser Thr Leu Ala Ile Lys Gln Asn Pro Leu Leu Ala Glu
                 80                  85                  90

Ala Tyr Ser Asn Leu Gly Asn Val Tyr Lys Glu Arg Gly Gln Leu
                 95                 100                 105

Gln Glu Ala Ile Glu His Tyr Arg His Ala Leu Arg Leu Lys Pro
                110                 115                 120

Asp Phe Ile Asp Gly Tyr Ile Asn Leu Ala Ala Ala Leu Val Ala
```

|  | 125 |  |  | 130 |  |  |  | 135 |  |
|---|---|---|---|---|---|---|---|---|---|

Ala Gly Asp Met Glu Gly Ala Val Gln Ala Tyr Val Ser Ala Leu
                140                 145                 150

Gln Tyr Asn Pro Asp Leu Tyr Cys Val Arg Ser Asp Leu Gly Asn
                155                 160                 165

Leu Leu Lys Ala Leu Gly Arg Leu Glu Glu Ala Lys Val Gly Val
                170                 175                 180

<210> SEQ ID NO 16
<211> LENGTH: 2120
<212> TYPE: DNA
<213> ORGANISM: Homo sapiens
<220> FEATURE:
<221> NAME/KEY: misc_feature
<223> OTHER INFORMATION: Incyte ID No: 1632930CB1

<400> SEQUENCE: 16

| | | | | | |
|---|---|---|---|---|---|
| gatggcggag | gacagcgagt | ctgcggccag | ccagcagagc | ctggaactgg | acgaccagga | 60 |
| cacgtgcggg | atagacgggg | acaatgagga | ggagacggag | cacgccaaag | gaagtcctgg | 120 |
| agggtatttg | ggagccaaaa | agaaaaagaa | gaaacagaag | agaaaaaagg | agaaaccaaa | 180 |
| ttccggaggc | accaagtcag | actcggcatc | tgattcccag | gagattaaaa | ttcagcagcc | 240 |
| ttcgaaaaat | cccagtgttc | caatgcagaa | gttgcaggat | atccagagag | caatggagct | 300 |
| gctatccgca | tgccagggcc | cagccaggaa | cattgatgag | gctgcaaagc | acagatacca | 360 |
| gttttgggac | acacaaccgg | taccaaaact | agatgaagtc | ataacatctc | atggtgcaat | 420 |
| tgaaccagat | aaagtcaacg | tacggcaaga | accgtattct | ttgccacagg | gttttatgtg | 480 |
| ggacacttta | gacttgagtg | atgccgaagt | gctcaaggag | ttatacacgt | tgttaaatga | 540 |
| gaattacgta | gaagatgatg | acaatatgtt | ccgatttgac | tattcacccg | agttcctgtt | 600 |
| gtgggctctc | cgtccaccag | gctggctcct | gcagtggcac | tgtggggtca | gagtgtcttc | 660 |
| aaataaaaaa | ctggtcgggt | tcataagtgc | catcccagca | aacattcgga | tttatgacag | 720 |
| tgtgaagaag | atggtagaaa | tcaactttct | ttgtgttcat | aagaagttga | gatcgaaacg | 780 |
| ggtagcccca | gtgctaatcc | gagagatcac | tagaagagtg | aacctggaag | ggatcttcca | 840 |
| ggctgtgtac | accgcgggag | tggttcttcc | taagcccata | gccacatgca | gatactggca | 900 |
| tcgatcacta | aaccccagaa | aattggtaga | agtgaaattt | tctcacttga | gtagaaatat | 960 |
| gactttacag | agaacaatga | agctatacag | acttccagat | gttacaaaga | cttcaggttt | 1020 |
| gagaccaatg | gaaccaaaag | atatcaaatc | agttcgagaa | ttaatcaaca | cttacctgaa | 1080 |
| gcagtttcat | ctggctccag | tgatggatga | agaggaagta | gcccactggt | tcctcccccg | 1140 |
| ggagcacatt | attgacacgt | ttgtagtgga | gagccccaac | ggtaaactga | ctgatttcct | 1200 |
| gagcttctat | acgctcccct | ccacggtgat | gcaccaccct | gctcacaaga | gcctcaaagc | 1260 |
| cgcctactca | ttctacaaca | tccacacaga | gacgcccctg | ctggacctca | tgagcgacgc | 1320 |
| gctcatcctg | gctaaatcga | aaggatttga | tgtattcaat | gcactggatt | tgatggaaaa | 1380 |
| taagacattc | ttgaaaaac | tcaagtttgg | tataggagat | ggcaatttgc | agtattacct | 1440 |
| gtacaattgg | aggtgtccag | gtacagattc | tgaaaaggtt | ggactagtac | tacaatagat | 1500 |
| ggatattttt | atttctagaa | ctctgacatc | atcatttgtt | aatatttaat | gatttctgga | 1560 |
| actgccattc | caaagaagaa | taaaagcaca | actcaagtga | aattgaagta | gtcgataatc | 1620 |
| agaaaagatg | acaaaagtcc | acatgtgaca | tttgtacgtt | tctagctaga | atgttaaact | 1680 |
| tcatcctttt | tttactgttg | acctatttgt | gggagggatg | aaaggctaca | agagcacat | 1740 |

```
tcttgtaatt ttcaaatttt tgcctgtctc ttgaagaggt attttttcac ccttagaaaa    1800
gggactgttt ttctatggac taagtagaag ttacagagtc atgtaagaaa atctttgcta    1860
ttgtgtggag agaaattgct gcatttctgt ttcttaagtg atggtacatt tgtccatgta    1920
acagaacaaa agatccattt ggaaattttt tttactggta tcaccttaca tggtatcact    1980
gggaacattt atggaatcaa cacttctgta gctcagtgac aggtggtggt tgtttaagtg    2040
cagagcaata ttaaaatgta ctggtgacta gtacatgtat ttctccataa gcagagttgc    2100
cgaatcaata aacatgcaat                                                2120
```

<210> SEQ ID NO 17
<211> LENGTH: 1559
<212> TYPE: DNA
<213> ORGANISM: Homo sapiens
<220> FEATURE:
<221> NAME/KEY: misc_feature
<223> OTHER INFORMATION: Incyte ID No: 2682663CB1

<400> SEQUENCE: 17

```
gcagccgtct acccggtgtc gcgttctgtg ttgtggcggc cctggatccg gcgtcagggc      60
gaccgggcgg acgaggtgga gccagagtct gtcaggcggg ttggtgaagg gcgcggggcc     120
gggcacggcg ttgggagtgc gcggcaggga ccggccaggc gggctgcagg cacctcagag     180
cccgggacac cccctcaacg tccgcaggcg cgatgaaggc actgatctta gtgggggggct    240 atgggacgcg gctacggccg ctgacgctga gcaccccgaa gccactggtg gacttctgca    300
ataagcccat cttgctgcac caagtggagg cgctagccgc ggcaggcgtg gaccacgtga    360
tcctggccgt gagctacatg tcgcaggtgc tggagaagga aatgaaggca caggagcaga    420
ggctgggaat ccgaatctcc atgtcccatg aagaggagcc tttggggaca gctgggcccc    480
tggcgctggc ccgtgaccta ctctctgaga ctgcagaccc tttcttcgtc ctcaacagtg    540
acgtgatctg cgatttcccc ttccaagcca tggtgcagtt ccaccggcac catggccagg    600
agggctccat cctggtgacc aagtggagg aaccctccaa gtacgtgtg tggtgtgtg      660 aggctgacac aggccgcatt caccggttcg tggagaagcc acaggtgttt gtgtccaata    720
agatcaacgc aggcatgtac atcctgagcc ctgcagtgct gcggcgcatc cagctgcagc    780
ctacgtccat tgagaaggag gtcttcccca ttatggccaa ggaggggcag ctatatgcca    840
tggagttaca gggcttctgg atggacattg gcagcccaa ggacttcctc actggcatgt    900
gcctcttcct gcagtcactg aggcagaagc agcctgagcg gctgtgctca ggccctggca    960
ttgtgggcaa cgtgctggtg gacccaagtg cccgcatcgg ccagaactgc agcattggcc   1020
ccaatgtgag cctgggacct ggcgtggtgg tcgaagatgg tgtgtgtatc cggcggtgca   1080
cggtgctgcg ggatgcccgg atccgttccc attcctggct tgagtcctgc attgtgggct   1140
ggcgctgccg cgtgggtcag tgggtacgca tggagaacgt gacagtgctg ggtgaggacg   1200
tcatagttaa tgatgagctc tacctcaacg gagccagcgt gctgccccac aagtctattg   1260
gcgagtcagt gccagagcct cgtatcatca tgtgagggga tgcagtgggg ctggccgagc   1320 cccggtttc ccatcagcaa ggggagtgct ggcctgacac atcagaagac cctggacttg   1380
tcattatttg tctgggggc actgggtgaa gctgaagctg ttggacacct gccttctcat   1440
gtggacatca tctggcagga tccctgctgg gcacacccca caaacccccac tccctcaaga   1500 agggccaggg ccagggctgt atggaataat aatttaatgc tcactgtgaa aaaaaaaaa    1559
```

<210> SEQ ID NO 18
<211> LENGTH: 2465
<212> TYPE: DNA
<213> ORGANISM: Homo sapiens
<220> FEATURE:
<221> NAME/KEY: misc_feature
<223> OTHER INFORMATION: Incyte ID No: 1265094CB1

<400> SEQUENCE: 18

| | | | | | |
|---|---|---|---|---|---|
| gctgagctaa | aatggctgag | gagagagtcg | cgacgagaac | tcaatttcct | gtatctactg | 60 |
| agtctcaaaa | accccggcag | aaaaaagctc | cagagtttcc | tattttggag | aagcagaact | 120 |
| ggttgattca | tcttcattat | atccggaaag | attatgaagc | ctgcaaggct | gttatcaaag | 180 |
| aacagcttca | agagactcag | ggattgtgtg | aatatgctat | ctatgtccaa | gcattgatat | 240 |
| ttcgcctaga | aggaaatatc | caagaatccc | tagaactctt | ccagacatgt | gcagttctta | 300 |
| gtcctcagag | tgctgataac | ctcaagcagg | tggccagatc | tttatttctt | ttgggaaaac | 360 |
| ataaagctgc | cattgaagta | tataatgaag | cagctaaact | caaccagaaa | gattgggaga | 420 |
| tcagccataa | cctaggagtt | tgctacatat | acctgaagca | gttcaacaag | gcacaagacc | 480 |
| agttgcacaa | tgccctgaat | cttaataggc | acgatctgac | ttatataatg | ctggggaaga | 540 |
| tccacttgct | ggagggagac | ttggacaagg | ccattgaagt | ctacaagaaa | gcagtggagt | 600 |
| tctcaccaga | aaatacagag | cttcttacaa | ctttaggatt | actctactta | cagctcggca | 660 |
| tttaccagaa | ggcatttgaa | catcttggca | atgcactgac | ttatgaccct | accaactaca | 720 |
| aggccatctt | ggcagcaggc | agcatgatgc | agacccacgg | ggactttgat | gttgccctca | 780 |
| ccaaatacag | agttgtggct | tgtgctgttc | cagaaagtcc | tccactctgg | aataacattg | 840 |
| gaatgtgttt | ctttggcaag | aagaaatatg | tggcggccat | cagctgcctg | aaacgagcca | 900 |
| actacttggc | acccttcgat | tggaagattc | tgtataattt | gggccttgtc | catttgacca | 960 |
| tgcagcagta | tgcatcagct | tttcattttc | tcagtgcggc | catcaacttc | cagccaaaga | 1020 |
| tgggggagct | ctacatgctc | ttggcagtgg | ctctgaccaa | tctggaagat | acagaaaatg | 1080 |
| ccaagagagc | ctacgcagaa | gcagtccacc | tggataagtg | taaccctta | gtaaacctga | 1140 |
| actatgctgt | gctgctgtac | aaccagggcg | agaagaagaa | cgccctggcc | caatatcagg | 1200 |
| agatggagaa | gaaagtcagc | ctactcaagg | acaatagctc | tctggaattt | gactctgaga | 1260 |
| tggtggagat | ggctcagaag | ttgggagctg | ctctccaggt | tggggaggca | ctggtctgga | 1320 |
| ccaaaccagt | taaagatccc | aaatcaaagc | accagaccac | ttcaaccagc | aaacctgcca | 1380 |
| gtttccagca | gcctctgggc | tctaatcaag | ctctaggaca | ggcaatgtct | tcagcagctg | 1440 |
| catacaggac | gctcccctca | ggtgctggag | gaacatccca | gttcacaaag | ccccatctc | 1500 |
| ttcctctgga | gccagagcct | gcggtggaat | caagtccaac | tgaaacatca | gaacaaataa | 1560 |
| gagagaaata | agaatagaat | gaatgacccc | aaaatagggt | tttcttgggc | gaggatgtgc | 1620 |
| tggattagga | aaggtgacat | gacacaggca | gagcagagtg | gcacccacca | cagaatacag | 1680 |
| tgtgtgttat | tacgagggagc | cagcagttga | gcctaaggtc | cttctaccta | cctggtattg | 1740 |
| gcatttgagg | tcggaaaccc | tctactgccc | cataagccag | gaaaagtgaa | aagagaacac | 1800 |
| agttcctta | agaactggca | gcaaggcttg | aggccttatg | tatgtagctg | agtcagcaag | 1860 |
| gtacatgatg | ctgtctgctt | tcaaaggac | ttttctctcc | tagctgactg | actccttcct | 1920 |
| tagttcaagg | aacagctgag | acagacctct | gctgagtagc | tctgtgatga | caaagccttg | 1980 |
| gtttaactga | ggtgatcctc | aggttgtgag | gtttattagt | ccccaaggca | aacacaaata | 2040 |
| ttagattaat | aatccaactt | taatagtata | catttaaaag | aaaaaaaaca | aaagccctgg | 2100 |

| | | |
|---|---|---|
| aagttgaggc caagcctgct gagtattgca gctgcatttg cccaaaggga atccagaaca | 2160 |
| agtccctccc tgtatttgt tcttgagagg ggtcagtcta gaagctagat cctatcagga | 2220 |
| tgaggagcag cagcccaggg cttgtctgga tcagcaccaa cgatttaaa gaaaaaagga | 2280 |
| agagtttctt agatgagtaa ttgttattga agatagtcag tgataaccac tgaccagatg | 2340 |
| ctatcaatac actatgtgtc cttttagaa taaagattac atatcatcat tcctttgggg | 2400 |
| aaaattgtta ttcaggtata aaacaagag atcataataa aaacctaaaa gaacctaaaa | 2460 |
| aaaaa | 2465 |

<210> SEQ ID NO 19
<211> LENGTH: 1927
<212> TYPE: DNA
<213> ORGANISM: Homo sapiens
<220> FEATURE:
<221> NAME/KEY: misc_feature
<223> OTHER INFORMATION: Incyte ID No: 1404963CB1

<400> SEQUENCE: 19

| | | |
|---|---|---|
| gcgttccccg ggagaaacat ggccgggagc agcgaggagg cgccagacta cgggcgaggc | 60 |
| gtcgtgatta tggatgattg gccagggtat gacttgaatt tattcacgta cccacagcac | 120 |
| tattatggag acttggagta tgtcctcatc cctcatggta tcattgtgga cagaattgag | 180 |
| cggctggcca aggatattat gaaagacata ggatatagtg acatcatggt cctgtgtgtg | 240 |
| cttaaggag gttacaaatt ctgtgctgat ctcgtagaac ccttaagaa catcagccga | 300 |
| aattcagatc gatttgtctc aatgaaggtt gatttcatca gactaaaaag ttacaggaat | 360 |
| gaccagtcca tgggtgagat gcagataatc ggaggcggtg atctttcaac gctggctgga | 420 |
| aagaatgttc tcattgttga ggatgttgtc ggaactggga ggaccatgaa agcactactc | 480 |
| agcaatatag agaaatacag gcccaacatg attaaggtag ccagtttgtt ggtgaagaga | 540 |
| acatccagaa gtgacggctt tagacctgac tatgctggat ttgagattcc aaacttattt | 600 |
| gtggtgggat atgccttaga ttacaatgaa tacttcagag atctgaatca catatgcgtc | 660 |
| atcaatgagc acggtaaaga aaaatatcga gtctaaagac atgaattctc accactaaag | 720 |
| tcccagatag catcatattt acgcctgtac ttgggaagcc agctgtcaag tttgtccccc | 780 |
| caggcatctt cactcagcag gatataaaag aaaaaaatgt tcaaatgaga gagctttctt | 840 |
| ttctgaggtt aatataaaga gtatcaaagg ttcctaagga aaagaaagca gtgcttttat | 900 |
| ttgacttgtt ccaaattaaa cactccgcct tgtgactcag caatgctatc taccttcaca | 960 |
| ctcctgagct ccgccttcct ttgttttgat acagtcatta tatttgatta gtattcccag | 1020 |
| gaataccccc acctagttac tcaaatattt ttcacttaac tttttatact cttatttgg | 1080 |
| taataagctt acaatattaa gaagctgggg acttttttt aactgaagac ttgagtcccc | 1140 |
| tataccggga atgcagctat taatagattc ccatattta aaggaggga aggacaatt | 1200 |
| taatataaat ttctgtttgt gcatttctga caggccatta ttatctgctt tgacaaagcc | 1260 |
| tttctgaaac gcagtgtaca atgaatctta atgatgttat gaaacgagct ttgctcgggg | 1320 |
| ctcttgattg gagcttccgg tatgtgatga cggtatgtca tgtatgcatg gatgtactca | 1380 |
| actgtgttta atactctgaa ttttaattag aaaaaaatac aatagcagca aggccctggt | 1440 |
| ttctaagctg tatccttta ttcatgtggg acatgagcaa atggcagaat tagggggcgag | 1500 |
| tgctttcaat gctcgaaact aagcaagtat aaattttcc tcttatttgc atgaaaggac | 1560 |
| aagcacactgt tatgccctgt cctaaatgtg aagacagagg ttgaatttt taaaaaatat | 1620 |

| | |
|---|---|
| ctttaaaaga ctgatcacaa aatccaaggt gctacaggaa acaagcacac tcaagaaagt | 1680 |
| tttttttctga ataacatttt tttccaattt ctccgttttta taagacattt cctaattttat | 1740 |
| ggggatttta attgaaaata aacttgagtc ccaatagagc tgttttttttc tcacttccta | 1800 |
| caaaatgcaa atgcaaaata aataactaag cagcttttgt ttggttctga accgtatgtg | 1860 |
| gcgtattgtt attaggttct agcttccttt aaactaataa agaataagaa aacttaaaaa | 1920 |
| aaaaaaa | 1927 |

<210> SEQ ID NO 20
<211> LENGTH: 1715
<212> TYPE: DNA
<213> ORGANISM: Homo sapiens
<220> FEATURE:
<221> NAME/KEY: misc_feature
<223> OTHER INFORMATION: Incyte ID No: 1405058CB1

<400> SEQUENCE: 20

| | |
|---|---|
| ggctcagccg tgggctctaa cgcggggctg ggggccggag acagacttcg cccaggtgac | 60 |
| gggtagtagg ggcggcgccg cttggcctcg tggggtgtaa gacccacttg ctgttgcccc | 120 |
| cggaccttgc cgccacacca gccctgtcct ggggcggaac cgaaggaagg tcgggccctg | 180 |
| ctgccccgcc ccgtccttcc tccttcccgg gcggtcactg tgcgtggctc acttttagag | 240 |
| tttacttcaa ccacgtggag cttccatggc ggcctctcag gtcctggggg agaagattaa | 300 |
| catcttgtcg ggagagactg tcaaagctgg ggacaggggacc ccgctgggga acgactgtcc | 360 |
| cgagcaagat aggctccccc agcgctcctg gaggcagaag tgtgcctcct acgtgttggc | 420 |
| cctgaggccc tggagcttca gtgcctcact cacaccggtg gccctgggca gtgcccttgc | 480 |
| ctacagatcc cacggtgtcc tggatcccag gctcttggtg ggttgtgccg tggctgtcct | 540 |
| ggctgtgcac ggggccggta atttggtcaa cacttactat gacttttcca agggcattga | 600 |
| ccacaaaaag agtgatgaca ggacacttgt ggaccgaatc ttggagccgc aggatgtcgt | 660 |
| ccggttcgga gtcttcctct acacgttggg ctgcgtctgt gccgcttgcc tctactacct | 720 |
| gtcccctctg aaactggagc acttggctct tatctacttt ggaggcctgt ctggctcctt | 780 |
| tctctacaca ggaggaattg gattcaagta cgtggctctg ggagacctca tcatcctcat | 840 |
| cacttttggc ccgctggctg tgatgttcgc ctacgccatc caggtgggggt ccctggccat | 900 |
| cttcccactg tctatgcca tcccccctcgc cctcagcacc gaggccattc tccattccaa | 960 |
| caacaccagg gacatggagt ccgaccggga ggctggtatc gtcacgctgg ccatcctcat | 1020 |
| cggccccacg ttctccctaca ttctctacaa cacactgctc ttcctgccct acctggtctt | 1080 |
| cagcatcctg gccacacact gcaccatcag cctggcactc ccctgctta ccattcccat | 1140 |
| ggccttctcc cttgagagac agtttcgaag ccaggccttc aacaaactgc ccagaggac | 1200 |
| tgccaagctc aacctcctgc tgggactttt ctatgtcttt ggcatcattc tggcaccagc | 1260 |
| aggcagtctg cccaaaattt aaggggacaa gtagctcccc ccacgacatg tctcccttttc | 1320 |
| ttagaatata ttaaagtcag agtctctgag gaaggaatgt gatttggcag tcagggtact | 1380 |
| aagcatgggt gggaactcct gccttataaa aattgttttt gtgttcttaa agataatatg | 1440 |
| ttgttttttct gttttttgtt ttttccattt tatgggggaat ttaaaaacca ttcttgtatc | 1500 |
| agaaggtgaa ttaggcgcat ggtctttgtt ttattaataa tttccactag agggtgttct | 1560 |
| caggtcactt ttcagtgaag tggacttagt tcctccttgt tctgtacaaa atgtctccag | 1620 |
| actttgtaaa ggagctgccc agtttggcct cctgtcccga aaagacccta ataactaggc | 1680 |

```
agagtgttgt cctgctttct tcgtctcgta ggata                                 1715
```

<210> SEQ ID NO 21
<211> LENGTH: 2617
<212> TYPE: DNA
<213> ORGANISM: Homo sapiens
<220> FEATURE:
<221> NAME/KEY: misc_feature
<223> OTHER INFORMATION: Incyte ID No: 1420940CB1

<400> SEQUENCE: 21

```
tgctgctgct gctgctgccg ccgccgccgc cgccgtccct gcgtccttcg gtctctgctc        60
ccgggacccg ggctccgccg cagccagcca gcatgtcggg gatcaagaag caaaagacgg       120
agaaccagca gaaatccacc aatgtagtct atcaggccca ccatgtgagc aggaataaga       180
gagggcaagt ggttggaaca aggggtgggt tccgaggatg taccgtgtgg ctaacaggtc       240
tctctggtgc tggaaaaaca acgataagtt ttgccctgga ggagtacctt gtctcccatg       300
ccatcccttg ttactccctg gatggggaca atgtccgtca tggccttaac agaaatctcg       360
gatcctctcc tggggacaga gaggaaaata tccgccggat tgctgaggtg gctaagctgt       420
ttgctgatgc tggtctggtc tgcattacca gctttatttc tccattcgca aaggatcgtg       480
agaatgcccg caaaatacat gaatcagcag ggctgccatt ctttgaaata tttgtagatg       540
cacctctaaa tatttgtgaa agcagagacg taaaaggcct ctataaaggg ccagagctg       600
gggagattaa aggatttaca ggtattgatt ctgattatga gaaacctgaa actcctgagc       660
gtgtgcttaa aaccaatttg tccacagtga gtgactgtgt ccaccaggta gtggaacttc       720
tgcaagagca gaacattgta ccctatacta taatcaaaga tatccacgaa ctctttgtgc       780
cggaaaacaa acttgaccac gtccgagctg aggctgaaac tctcccttca ttatcaatta       840
ctaagctgga tctccagtgg gtccaggttt tgagcgaagc tgggccact ccctcaaag        900
gtttcatgcg ggagaaagag tacttacagg ttatgcactt tgacaccctg ctagatggca       960
tggcccttcc tgatggcgtg atcaacatga gcatccccat tgtactgccc gtctctgcag      1020
aggataagac acggctggaa gggtgcagca gtttgtcct ggcacatggt ggacggaggg       1080
tagctatctt acgagacgct gaattctatg aacacagaaa agaggaacgc tgttcccgtg      1140
tttgggggac aacatgtaca aaacaccccc atatcaaaat ggtgatggaa agtggggact      1200
ggctggttgg tggagacctt caggtgctgg agaaaataag atggaatgat gggctggacc      1260
aataccgtct gacacctctg gagctcaaac agaaatgtaa agaaatgaat gctgatgcgg      1320
tgtttgcatt ccagttgcgc aatcctgtcc acaatggcca tgccctgttg atgcaggaca      1380
ctcgccgcag gctcctagag agggggctaca agcacccggt cctcctacta caccctctgg      1440
gcggctggac caaggatgac gatgtgcctc tagactggcg gatgaagcag cacgcggctg      1500
tgctcgagga agggtcctg gatcccaagt caaccattgt tgccatcttt ccgtctccca       1560
tgttatatgc tggccccaca gaggtccagt ggcactgcag gtcccggatg attgcgggtg      1620
ccaatttcta cattgtgggg agggaccctg caggaatgcc ccatcctgaa accaagaagg      1680
atctgtatga acccactcat gggggcaagg tcttgagcat ggcccctggc ctcacctctg      1740
tggaaatcat tccattccga gtggctgcct acaacaaagc caaaaaagcc atggacttct      1800
atgatccagc aaggcacaat gagtttgact tcatctcagg aactcgaatg aggaagctcg      1860
cccgggaagg agagaatccc ccagatggct tcatggccca caaagcatgg aaggtcctga      1920
cagattatta caggtccctg gagaagaact aagcctttgg ctccagagtt tctttctgaa      1980
```

```
gtgctctttg attaccttt  ctatttttat gattagatgc tttgtattaa attgcttctc      2040
aatgatgcat tttaatcttt tataatgaag taaaagttgt gtctataatt aaaaaaaaat      2100
atatatatat acacacacac atatacatac aaagtcaaac tgaagaccaa atcttagcag      2160
gtaaaagcaa tattcttata catttcataa taaaattagc tctatgtatt ttctactgca      2220
cctgagcagg caggtcccag atttcttaag gctttgtttg accatgtgtc tagttacttg      2280
ctgaaaagtg aatatatttt ccagcatgtc ttgacaacct gtactcttcc aatgtcattt      2340
atcagttgta aaatatatca gattgtgtcc tcttctgtac aattgacaaa aaaaaaaatt      2400 ttttttctc  actctaaaag aggtgtggct cacatcaaga ttcttcctga tattttacct      2460
catgctgtac aaagccttaa tgttgtaatc atatcctacg tgttgaagac ctgactggag      2520
aaacaaaatg tggcataacg tgaatttat  cttagggatc tgtgcagcct atttctgtca      2580
caaaggtaaa ttgtccaata agggagtctt aatgggc                              2617
```

<210> SEQ ID NO 22
<211> LENGTH: 1130
<212> TYPE: DNA
<213> ORGANISM: Homo sapiens
<220> FEATURE:
<221> NAME/KEY: misc_feature
<223> OTHER INFORMATION: Incyte ID No: 1784742CB1

<400> SEQUENCE: 22

```
ggcggcgacg gcgacggcgg cggcatggcg gagagcgagg ccgagacccc cagcaccccg        60
ggggagttcg agagcaagta cttcgagttc catggcgtgc ggctgccgcc cttctgccgc       120
gggaagatgg aggagatcgc caacttcccg gtgcggccca cgacgtgtg  gatcgtcacc       180 taccccaagt ccggcaccag cttgctgcag gaggtggtct acttggtgag ccagggcgct       240
gaccccgatg agatcggctt gatgaacatc gacgagcagc tcccggtcct ggagtaccca       300
cagccgggcc tggacatcat caaggaactg acctctcccc gcctcatcaa gagccacctg       360
ccctaccgct ttctgccctc tgacctccac aatggagact ccaaggtcat ctatatggct       420 cgcaaccca  aggatctggt ggtgtcttat tatcagttcc accgctctct gcggaccatg       480
agctaccgag gcacctttca agaattctgc cggaggttta tgaatgataa gctgggctac       540
ggctcctggt ttgagcacgt gcaggagttc tgggagcacc gcatggactc gaacgtgctt       600
tttctcaagt atgaagacat gcatcgggac ctggtgacga tggtggagca gctggccaga       660
ttcctggggg tgtcctgtga caaggcccag ctggaagccc tgacggagca gctgccaccag       720 ctggtggacc agtgctgcaa cgctgaggcc ctgcccgtgg gccggggaag agttgggctg       780
tggaaggaca tcttcaccgt ctccatgaat gagaagtttg acttggtgta taaacagaag       840
atgggaaagt gtgacctcac gtttgacttt tatttataat aacagaaaca acaacctgca       900
tgctcacaat acccagacag tctactagcc aaaagtcctg tatgcattca tttattcctt       960
gctggacaaa ctctggaagc agcgtgtgaa acagcggggg aagggaagag cggcgtgatc      1020
ggagggagtg tgatgattcc caaccgaaag cagctgtctc gcctttagaa cgtgcagcct      1080
ctccatgtct gattacaaac agtctccaca ttgcagttcc aatgggctgg                 1130
```

<210> SEQ ID NO 23
<211> LENGTH: 872
<212> TYPE: DNA
<213> ORGANISM: Homo sapiens
<220> FEATURE:
<221> NAME/KEY: misc_feature
<223> OTHER INFORMATION: Incyte ID No: 1967138CB1

<400> SEQUENCE: 23

| | | | | | |
|---|---|---|---|---|---|
| gttcccaggc | ctcccagtgt | gttcccagat | ggcagacttc | tgcgttatga | cccggctgct | 60 |
| gggctacgtg | gaccccctgg | atcccagctt | tgtggctgcc | gtcatcacca | tcaccttcaa | 120 |
| tccgctctac | tggaatgtgg | ttgcacgatg | gaaacacaag | acccgcaagc | tgagcagggc | 180 |
| cttcggatcc | ccctacctgg | cctgctactc | tctaagcgtc | accatcctgc | tcctgaactt | 240 |
| cctgcgctcg | cactgcttca | cgcaggccat | gctgagccag | cccaggatgg | agagcctgga | 300 |
| caccccgcg | gcctacagcc | tgggcctcgc | gctcctggga | ctgggcgtcg | tgctcgtgct | 360 |
| ctccagcttc | tttgcactgg | ggttcgctgg | aactttccta | ggtgattact | cgggatcct | 420 |
| caaggaggcg | agagtgaccg | tgttcccctt | caacatcctg | acaaccccca | tgtactgggg | 480 |
| aagcacagcc | aactacctgg | gctgggccat | catgcacgcc | agcccacgg | gcctgctcct | 540 |
| gacggtgctg | gtggccctca | cctacatagt | ggctctccta | tacgaagagc | ccttcaccgc | 600 |
| tgagatctac | cggcagaaag | cctccgggtc | cacaagagg | agctgattga | gctgcaacag | 660 |
| ctttgctgaa | ggcctggcca | gctcctggc | ctgcccaag | tggcaggccc | tgcgcagggc | 720 |
| gagaatggtg | cctgctgctc | agggctcgcc | cccggcgtgg | gctgcccag | tgccttggaa | 780 |
| cctgctgcct | tggggaccct | ggacgtgccg | acatatggcc | attgagctcc | aacccacaca | 840 |
| ttcccattca | ccaataaagg | caccctgacc | cc | | | 872 |

<210> SEQ ID NO 24
<211> LENGTH: 1552
<212> TYPE: DNA
<213> ORGANISM: Homo sapiens
<220> FEATURE:
<221> NAME/KEY: misc_feature
<223> OTHER INFORMATION: Incyte ID No: 2124351CB1

<400> SEQUENCE: 24

| | | | | | |
|---|---|---|---|---|---|
| ggggtccgct | agtcgcgggg | cggcggcggc | ggctgcgggc | gcgaggttcc | cagcaggatg | 60 |
| ccccggctct | gcaggaagct | gaagtgagag | gcccggagag | ggcccagccc | gcccggggca | 120 |
| ggatgaccaa | ggcccggctg | ttccggctgt | ggctggtgct | ggggtcggtg | ttcatgatcc | 180 |
| tgctgatcat | cgtgtactgg | gacagcgcag | gcgccgcgca | cttctacttg | cacacgtcct | 240 |
| tctctaggcc | gcacacgggg | ccgccgctgc | ccacgcccgg | gccggacagg | acagggagc | 300 |
| tcacggccga | ctccgatgtc | gacgagtttc | tggacaagtt | tctcagtgct | ggcgtgaagc | 360 |
| agagcgacct | tcccagaaag | gagacggagc | agccgcctgc | gccggggagc | atggaggaga | 420 |
| gcgtgagagg | ctacgactgg | tccccgcgcg | acgcccggcg | cagcccagac | cagggccggc | 480 |
| agcaggcgga | gcggaggagc | gtgctgcggg | gcttctgcgc | caactccagc | ctggccttcc | 540 |
| ccaccaagga | gcgcgcattc | gacgacatcc | ccaactcgga | gctgagccac | ctgatcgtgg | 600 |
| acgaccggca | cggggccatc | tactgctacg | tgcccaaggt | ggcctgcacc | aactggaagc | 660 |
| gcgtgatgat | cgtgctgagc | ggaagcctgc | tgcaccgcg | tgcgccctac | gcgacccgc | 720 |
| tgcgcatccc | gcgcgagcac | gtgcacaacg | ccagcgcgca | cctgaccttc | aacaagttct | 780 |
| ggcgccgcta | cggaagctc | tcccgccacc | tcatgaaggt | caagctcaag | aagtacacca | 840 |
| agttcctctt | cgtgcgcgac | cccttcgtgc | gcctgatctc | cgccttccgc | agcaagttcg | 900 |
| agctggagaa | cgaggagttc | taccgcaagt | tcgccgtgcc | catgctgcgg | ctgtacgcca | 960 |
| accacaccag | cctgccccgcc | tcggcgcgcg | aggccttccg | cgctggcctc | aaggtgtcct | 1020 |

-continued

| | |
|---|---|
| tcgccaactt catccagtac ctgctggacc cgcacacgga gaagctggcg cccttcaacg | 1080 |
| agcactggcg gcaggtgtac cgcctctgcc acccgtgcca gatcgactac gacttcgtgg | 1140 |
| ggaagctgga gactctggac gaggacgccg cgcagctgct gcagctactc caggtggacc | 1200 |
| ggcagctccg cttccccccg agctaccgga acaggaccgc cagcagctgg gaggaggact | 1260 |
| ggttcgccaa gatcccctg gcctggaggc agcagctgta taaactctac gaggccgact | 1320 |
| ttgttctctt cggctacccc aagcccgaaa acctcctccg agactgaaag ctttcgcgtt | 1380 |
| gcttttctc gcgtgcctgg aacctgacgc acgcgcactc cagttttttt atgacctacg | 1440 |
| attttgcaat ctgggcttct tgttcactcc actgcctcta tccattgagt actgtatcga | 1500 |
| tattgttttt taagattaat atatttcagg tatttaatac gaaaaaaaaa aa | 1552 |

<210> SEQ ID NO 25
<211> LENGTH: 2731
<212> TYPE: DNA
<213> ORGANISM: Homo sapiens
<220> FEATURE:
<221> NAME/KEY: misc_feature
<223> OTHER INFORMATION: Incyte ID No: 2153162CB1

<400> SEQUENCE: 25

| | |
|---|---|
| gccgcaagcg gcatggagga ggcggaggcc gcggcgagcc gggccgagca gtgagggccc | 60 |
| tagcggggcc cgagcggggc ccggggcccc taagccattc ctgaagtcat gggctggcca | 120 |
| ggacattggt gacccgccaa tccggtatgg acgactggaa gccagcccc ctcatcaagc | 180 |
| cctttgggc tcggaagaag cggagctggt accttacctg gaagtataaa ctgacaaacc | 240 |
| agcgggccct gcggagattc tgtcagacag gggccgtgct tttcctgctg gtgactgtca | 300 |
| ttgtcaatat caagttgatc ctggacactc ggcgagccat cagtgaagcc aatgaagacc | 360 |
| cagagccaga gcaagactat gatgaggccc taggccgcct ggagccccca cggcgcagag | 420 |
| gcagtggtcc ccggcgggtc ctggacgtag aggtgtattc aagtcgcagc aaagtatatg | 480 |
| tggcagtgga tggcaccacg gtgctggagg atgaggcccg ggagcagggc cggggcatcc | 540 |
| atgtcattgt cctcaaccag gccacgggcc acgtgatggc aaaacgtgtg tttgacacgt | 600 |
| actcacctca tgaggatgag gccatggtgc tattcctcaa catggtagcg cccggccgag | 660 |
| tgctcatctg cactgtcaag gatgagggct ccttccacct caaggacaca gccaaggctc | 720 |
| tgctgaggag cctgggcagc caggctggcc ctgccctggg ctggagggac acatgggcct | 780 |
| tcgtgggacg aaaaggaggt cctgtcttcg gggagaaaca ttctaagtca cctgccctct | 840 |
| cttcctgggg ggacccagtc ctgctgaaga cagatgtgcc attgagctca gcagaagagg | 900 |
| cagagtgcca ctgggcagac acagagctga accgtcgccg ccggcgcttc tgcagcaaag | 960 |
| ttgagggcta tggaagtgta tgcagctgca aggaccccac acccatcgag ttcagccctg | 1020 |
| acccactccc agacaacaag gtcctcaatg tgcctgtggc tgtcattgca gggaaccgac | 1080 |
| ccaattacct gtacaggatg ctgcgctctc tgctttcagc ccaggggtg tctcctcaga | 1140 |
| tgataacagt tttcattgac ggctactatg aggaaccat ggatgtggtg cactgtttg | 1200 |
| gtctgagggg catccagcat actcccatca gcatcaagaa tgcccgcgtg tctcagcact | 1260 |
| acaaggccag cctcactgcc actttcaacc tgttccgga ggccaagttt gctgtggttc | 1320 |
| tggaagagga cctggacatt gctgtggatt ttttcagttt cctgagccaa tccatccacc | 1380 |
| tactggagga ggatgacagc ctgtactgca tctctgcctg gaatgaccag gggtatgaac | 1440 |
| acacggctga ggacccagca ctactgtacc gtgtggagac catgcctggg ctgggctggg | 1500 |

-continued

```
tgctcaggag gtccttgtac aaggaggagc ttgagcccaa gtggcctaca ccggaaaagc      1560
tctgggattg ggacatgtgg atgcggatgc ctgaacaacg ccggggccga gagtgcatca      1620
tccctgacgt ttcccgatcc taccactttg gcatcgtcgg cctcaacatg aatggctact      1680
ttcacgaggc ctacttcaag aagcacaagt tcaacacggt tccaggtgtc cagctcagga      1740
atgtggacag tctgaagaaa gaagcttatg aagtggaagt tcacaggctg ctcagtgagg      1800
ctgaggttct ggaccacagc aagaaccctt gtgaagactc tttcctgcca gacacagagg      1860
gccacaccta cgtggccttt attcgaatgg agaaagatga tgacttcacc acctggaccc      1920
agcttgccaa gtgcctccat atctgggacc tggatgtgcg tggcaaccat cggggcctgt      1980
ggagattgtt tcggaagaag aaccacttcc tggtggtggg ggtcccggct tcccctact       2040 cagtgaagaa gccaccctca gtcaccccaa ttttcctgga gccaccccca aaggaggagg      2100 gagcccagg agccccagaa cagacatgag acctcctcca ggaccctgcg gggctgggta       2160
ctgtgtaccc ccaggctggc tagcccttcc ctccatcctg taggattttg tagatgctgg      2220 tagggggctgg ggctaccttg ttttaacat gagacttaat tactaactcc aaggggaggg      2280 ttccctgct ccaacacccc gttcctgagt taaaagtcta tttatttact tccttgttgg       2340
agaagggcag gagagtacct gggaatcatt acgatcccta gcagctcatc ctgcccttg       2400 aataccctca ctttccaggc ctggctcaga atctaaccta tttattgact gtcctgaggg      2460
ccttgaaaac aggccgaacc tggagggcct ggatttcttt ttgggctgga atgctgccct      2520
gagggtgggg ctggctctta tcaggaaac tgctgtgccc aacccatgga caggcccagc      2580
tggggcccac atgctgacac agactcactc agagaccctt agacactgga ccaggcctcc      2640
tctcagcctt ctctttgtcc agatttccaa agctggataa gttggtcatt gattaaaaaa      2700
ggagaagccc tctgggaaaa aaaaaaaaaa a                                    2731
```

<210> SEQ ID NO 26
<211> LENGTH: 2065
<212> TYPE: DNA
<213> ORGANISM: Homo sapiens
<220> FEATURE:
<221> NAME/KEY: misc_feature
<223> OTHER INFORMATION: Incyte ID No: 2617407CB1

<400> SEQUENCE: 26

```
gccaggatgc ctccagtctg ggggaaaatg cttcctcatt tgcttctccc agcccacctc       60
aagcagtctc cccacccctt gagtctcagc agtgttaaag ctgttacttt cacagcttcc      120
tgggagcgag tgctttctca agcccgtctt gcaaggtctt ccacttcagc acaatgctac      180
tgcctaaaaa aatgaagctc ctgctgtttc tggtttccca gatggccatc ttggctctat      240
tcttccacat gtacagccac aacatcagct ccctgtctat gaaggcacag cccgagcgca      300
tgcacgtgct ggttctgtct tcctggcgct ctggctcttc ttttgtgggg cagctttttg      360
ggcagcaccc agatgttttc tacctgatgg agcccgcctg gcacgtgtgg atgaccttca      420
agcagagcac cgcctggatg ctgcacatgg ctgtgcggga tctgatacgg gccgtcttct      480
tgtgcgacat gagcgtcttt gatgcctaca tggaacctgg tccccggaga cagtccagcc      540
tctttcagtg ggagaacagc cgggcccgt gttctgcacc tgcctgtgac atcatcccac       600
aagatgaatc atccccgggg ctcactgcag gctcctgtgc agtcaacagc cctttgaagt      660
tgttggagaa agcctgccgc tcctacagcc acgtggtgct caaggaggtg cgcttcttca      720
acctgcagtc cctctacccg ctgctgaaag acccctccct caacctgcat atcgtgcacc      780
```

```
tggtccggga ccccgggcc gtgttccgtt cccgagaacg cacaaaggga gatctcatga      840
ttgacagtcg cattgtgatg gggcagcatg agcagaaact caagaaggag gaccaaccct      900
actatgtgat gcaggtcatc tgccaaagcc agctggagat ctacaagacc atccagtcct      960
tgcccaaggc cctgcaggaa cgctacctgc ttgtgcgcta tgaggacctg gctcgagccc     1020
ctgtggccca gacttcccga atgtatgaat tcgtgggatt ggaattcttg ccccatcttc     1080
agacctgggt gcataacatc acccgaggca agggcatggg tgaccacgct ttccacacaa     1140
atgccaggga tgcccttaat gtctcccagg cttggcgctg gtctttgccc tatgaaaagg     1200
tttctcgact tcagaaagcc tgtggcgatg ccatgaattt gctgggctac cgccacgtca     1260
gatctgaaca agaacagaga aacctgttgc tggatcttct gtctacctgg actgtccctg     1320
agcaaatcca ctaagagggt tgagaaggct tgctgccac ctggtgtcag cctcagtcac     1380
tttctctgaa tgcttctgag ccttgcctac atctctgagc cttaactaca tgtctgtggg     1440
tatcacactg agtgtgagtt gtgtccacac gtgctcaagc agaaggactt ttgtgtccat     1500
gcttgtgtct agaaaacaga ctggggaacc ttatgtgagc agcacatccc accagtgaaa     1560
cagggtattg ctcttcttct tttcttgatc ttcctgtctg ggcagacttc agagactttg     1620
tggcctggag gcctattaag cacgacacag tatcagtgga attgatccat aaacctccct     1680
gtccacatct tgcccaatgg ggaatggatc tttcaccaaa gagctcacca gcattttcca     1740
cagagatgca aattctgagc ccttggagtt cccagtggat tcaaggaagg aagtgggaac     1800
aaggttggat gcctacttat gagcttgacc atcacagcta tcggtaatca gaaatatgaa     1860
acaaaatctc tgcacaaaag agcaagctct taagttcaca gggtgcctgg gctgcatttg     1920
aatatcactt cccctctgca ttttcccatc acatagaaga ctttgacctg tgaagctgcc     1980
atctgttaat actaaaattc ccaaataagg ttctgtttag aatgtccctt tttatgcttc     2040
ttaattatta gcagtaaatg ttcat                                          2065
```

<210> SEQ ID NO 27
<211> LENGTH: 2748
<212> TYPE: DNA
<213> ORGANISM: Homo sapiens
<220> FEATURE:
<221> NAME/KEY: misc_feature
<223> OTHER INFORMATION: Incyte ID No: 2963717CB1

<400> SEQUENCE: 27

```
cgagagacag gaatcggggt ttctgggtga cggtgatctc ggggtgggca ggactccaaa       60
ggcccgtcga cccggtggtg gactccttgc actgggattg gacatatgca agcgggagat      120
ttggggccgg cgctcaaaat cggggggcgg gggtggactc gggtttggac cccaggatcc      180
gatcagcgga cccttgattc aacgtgggct ccagcgtgac atggctgaag cgcaccaggc      240
cgtgggcttc cgaccctcgc tgacctcgga cggggctgaa gtggaactca gtgcccctgt      300
gctgcaggag atctacctct ctggcctgcg ctcctggaaa aggcatctct cacgtttctg      360
gaatgacttt ctcaccggtg tgtttcctgc cagcccctc agttggcttt tcctcttcag      420
tgccatccag cttgcctggt tcctccagct ggatccttcc ttaggactga tggagaagat      480
caaagagttc tgcctgact ggggtggaca acaccacggg ctccggggg tcctggcagc      540 cgcgctgttt gcctcgtgtt tgtggggagc cctgatcttc acactgcacg tggccctgag      600
gctgcttctg tcctaccacg gctggcttct gagccccac ggagccatgt cctcccccac      660
caagacctgg ctgccctgg tccgcatctt ctctggccgc cacccgatgc tgttcagtta      720
```

-continued

| | |
|---|---|
| ccagcgctcc ctgccacgcc agcccgtgcc ctctgtgcag acaccgtgc gcaagtacct | 780 |
| ggagtcggtc cggcccatcc tctccgacga ggacttcgac tggaccgcgg tcctggcgca | 840 |
| ggaattcctg aggctgcagg cgtcactgct gcagtggtac ctgcggctca agtcctggtg | 900 |
| ggcgtccaat tatgtcagtg actggtggga ggaatttgtg tacctgcgct cccgaaatcc | 960 |
| gctgatggtg aacagcaact attacatgat ggacttcctg tatgtcacac ccacgcctct | 1020 |
| gcaggcagct cgcgctggga atgccgtcca tgccctcctc ctgtaccgcc accgcctgaa | 1080 |
| ccgccaggag ataccccga ctttgctgat gggaatgcgc cccttatgct ctgcccagta | 1140 |
| cgagaagatc ttcaacacca cgcggattcc agggtccaa aaagactaca tccgccacct | 1200 |
| ccatgacagc caacacgtgg ctgtcttcca ccggggccga ttcttccgca tggggaccca | 1260 |
| ctcccgaaac agcctgcttt ccccgagagc cctggagcag cagtttcaga gaatcctgga | 1320 |
| tgatccctca ccggcctgcc ccacgagga acatctggca gctctgacag ctgctcccag | 1380 |
| gggcacgtgg gcccaggtgc ggacatccct gaagacccag gcagcggagg ccctggaggc | 1440 |
| ggtggaaggg gccgctttct ttgtgtcact ggatgctgag cccgcgggc tcaccaggga | 1500 |
| ggacccggca gcgtcgttgg atgcctacgc ccatgctctg ctggctggcc ggggccatga | 1560 |
| tcgctggttt gacaaatcct tcaccctaat cgtcttctct aacgggaagc tgggcctcag | 1620 |
| cgtggagcac tcctgggccg actgccccat ctcaggacac atgtgggagt tcactctggc | 1680 |
| tacagaatgc tttcagctgg gctactcaac agatggccac tgcaagggc acccggaccc | 1740 |
| cacactaccc cagccccagc ggctgcaatg ggaccttcca gaccagatcc actcctccat | 1800 |
| ctctctagcc ctgaggggag ccaagatctt gtctgaaaat gtcgactgcc atgtcgttcc | 1860 |
| attctcccta tttggcaaga gcttcatccg acgctgccac ctctcttcag acagcttcat | 1920 |
| ccagatcgcc ttgcaactgg cccacttccg ggacaggggt caattctgcc tgacttatga | 1980 |
| gtcggccatg actcgcttat tcctggaagg ccggacggga acggtgcggt cttgcacgag | 2040 |
| ggaggcctgc aactttgtca gggccatgga ggacaaagag aagacggacc cacagtgcct | 2100 |
| cgccctgttc cgcgtggcag tggacaagca ccaggctctg ctgaaggcag ccatgagcgg | 2160 |
| gcagggagtt gaccgccacc tgtttgcgct gtacatcgtg tcccgattcc tccacctgca | 2220 |
| gtcgcccttc ctgacccagg tccattcgga gcagtggcag ctgtccacca gccagatccc | 2280 |
| tgttcagcaa atgcatctgt ttgacgtcca caattacccg gactatgttt cctcaggcgg | 2340 |
| tggattcggg cctgctgatg accatggtta tggtgtttct tatatcttca tggggatgg | 2400 |
| catgatcacc ttccacatct ccagcaaaaa atcaagcaca aaaacggatt cccacaggct | 2460 |
| ggggcagcac attgaggacg cactgctgga tgtggcctcc ctgttccagg cgggacagca | 2520 |
| ttttaagcgc cggttcagag ggtcagggaa ggagaactcc aggcacaggt gtggatttct | 2580 |
| ctcccgccag actggggcct ccaaggcctc aatgacatcc accgacttct gactccttcc | 2640 |
| agcaggcagc tggcctctcc aaggaataag ggtgaaattg ccacagctgg ctgacacagg | 2700 |
| acagggcaa ctggtttggc aaccccacat ccaggcaaat aaagatgg | 2748 |

<210> SEQ ID NO 28
<211> LENGTH: 1079
<212> TYPE: DNA
<213> ORGANISM: Homo sapiens
<220> FEATURE:
<221> NAME/KEY: misc_feature
<223> OTHER INFORMATION: Incyte ID No: 3360857CB1

<400> SEQUENCE: 28

-continued

| | |
|---|---|
| caggatggtg gacagcgtgt accggacccg ctccctgggg gtggcggccg aagggctccc | 60 |
| ggaccagtac gcggacgggg aggcggcgcg cgtgtggcag ctgtatatcg agacacccg | 120 |
| cagccgcacc gccgagtaca aggcatggct gcttgggctg ctgcgccagc acggctgcca | 180 |
| gcgggtgctc gacgtagcct gtggcactgg ggtggactcc attatgctgg tggaagaggg | 240 |
| cttcagtgtg acgagtgtgg atgccagtga caagatgctg aagtatgcac ttaaggagcg | 300 |
| ctggaaccgg cggcacgagc ccgccttcga caagtgggtc atcgaagaag ccaactggat | 360 |
| gactctggac aaagatgtgc cccagtcagc agagggtggc tttgatgctg tcatctgcct | 420 |
| tggaaacagt ttcgctcact tgccagactg caaagggac cagagtgagc accggctggc | 480 |
| gctgaaaaac attgcgagca tggtgcgggc agggggccta ctggtcattg atcatcgcaa | 540 |
| ctacgaccac atcctcagta caggctgtgc acccccaggg aagaacatct actataagag | 600 |
| tgacttgacc aaggacgtca acacatcagt gctgatagtg aacaacaagg cccacatggt | 660 |
| gaccctggac tatacggtgc aggtgccggg ggctggccag gatggctctc ctggcttgag | 720 |
| taagttccgg ctctcctact acccacactg tctggcatcc ttcacggagc tgctccaagc | 780 |
| agccttcgga ggtaagtgcc agcacagcgt cctgggcgac ttcaagcctt acaagccagg | 840 |
| ccaaacctac attccctgct acttcatcca cgtgctcaag aggacagact gagtgtggcc | 900 |
| tcagctccca caagcctctg cccaggcact gctaggctct gtctggaaga tggggaccag | 960 |
| cagccccaca ccagggccag cctctagagc agactacagc tggggtgcag ggatgtgggt | 1020 |
| tccacagacg gaagggtaaa caatatagtc tttttcagtt cctgcaaaaa aaaaaaaaa | 1079 |

<210> SEQ ID NO 29
<211> LENGTH: 2340
<212> TYPE: DNA
<213> ORGANISM: Homo sapiens
<220> FEATURE:
<221> NAME/KEY: misc_feature
<223> OTHER INFORMATION: Incyte ID No: 3449671CB1

<400> SEQUENCE: 29

| | |
|---|---|
| gcgcacgctt cggggtctcc gggaagtcgc ggcgccttcg gatgtggcgg atgcggccgt | 60 |
| gagccggcgg gggaggtgct gctgctgcct ccactgtact cagacccagg tagcacagga | 120 |
| ttgtccatcc tccagcagct cagtgcaacg gtgtgaactc agcctgtttc agagcctcca | 180 |
| caccatgacc tccaagaagc tggtgaactc ggtggctggc tgtgctgatg acgctcttgc | 240 |
| tggcctggtg gcctgcaacc ccaacctgca gctcctgcag ggccacgcg tggccctccg | 300 |
| ttctgacctg gacagcctca agggccgggt ggcactgctg tcgggtgggg gctctggcca | 360 |
| tgagcctgcc catgctggtt tcatagggaa ggggatgctg actggggtca tcgcgggagc | 420 |
| tgtgttcacc tccccggcag tgggcagcat cctggcagcc atcagggccg tggcccaggc | 480 |
| cggcacagtg gggacgctcc ttatcgtgaa gaactacact ggggatcggc tcaacttcgg | 540 |
| cctggcccgg gagcaggccc gggctgaagg catcccggtg gagatggtgg tgattgggga | 600 |
| cgacagcgcc ttcactgtcc tgaagaaggc aggccggcgg gggctgtgcg gcaccgtgct | 660 |
| tatacacaag gtggcaggtg ctctggctga ggctggtgtg gggctggagg agatcgcaaa | 720 |
| gcaggtgaac gtggtcacca aggccatggg taccctgggg gtgagcttat cctcctgcag | 780 |
| cgtccctggt tccaaaccca ccttcgagct ctcagccgac gaggtggagc tgggcctggg | 840 |
| gatccacggg gaagctggtg tgcgccggat aaagatggca accgccgatg agattgtgaa | 900 |
| actcatgctc gaccacatga caaacaccac caacgcgtcc catgtgcctg tgcagcccgg | 960 |

-continued

| | |
|---|---|
| ctcctcagtt gtgatgatgg tcaacaacct gggtggcctg tcattcctgg aactgggcat | 1020 |
| catagccgac gctaccgtcc gctccctgga gggccgcggg gtgaagattg cccgtgccct | 1080 |
| ggtgggcacc ttcatgtcag cactggagat gcctggcatt tctctcaccc tcctgctggt | 1140 |
| ggatgagcct ctcctgaaac tgatagatgc tgaaaccact gcagcagcct ggcctaacgt | 1200 |
| ggctgcagtc tccattactg gcggaagcg agccgggta gcccctgccg agccccagga | 1260 |
| ggcccctgat tccactgctg caggaggctc agcctcgaag cggatggcgc tggtgctgga | 1320 |
| acgggtgtgc agcactctcc tgggcctgga ggaacacctg aatgccctgg accgggctgc | 1380 |
| tggtgacggc gactgtggca ccacccacag ccgtgcggcc agagcaatcc aggagtggct | 1440 |
| gaaggagggc ccaccccctg ccagccctgc ccagctgctc tccaagttgt ctgttctgct | 1500 |
| cctggagaag atgggaggct catctgggggc gctctatggc ctgttcctga ctgcggctgc | 1560 |
| acagcccctg aaggccaaga ccagcctccc agcctggtct gctgccatgg atgccggcct | 1620 |
| ggaagccatg cagaagtatg gcaaggctgc tccagggac aggactatgc tggattctct | 1680 |
| gtgggcagcg gggcaggagc tccaagcctg gaagagccca ggagctgatc tgttacaagt | 1740 |
| cctgaccaaa gcagtcaaga gtgccgaagc tgcagccgag gccaccaaga atatggaagc | 1800 |
| tggagccgga agagccagtt atatcagctc agcacggctg gagcagccag accccgggc | 1860 |
| ggtggcagct gctgccatcc tccgggccat cttggaggtc ttgcagagct agggtgtgtg | 1920 |
| actgcctccc ttggcctcag ctcctctcac tgctgtgctg aggtggcctt tgtcacttcc | 1980 |
| ttctgccttc caaccctcac cttccccccgg cctggcccca ttggcccacc ctctaagttg | 2040 |
| agcaggaaat cctccaccaa gcttccagaa ctacagacag cacccagagt gagctggagt | 2100 |
| gggtccccat gcctctccag catgcccttt ccctttgcag gagggtggag tccctgggtc | 2160 |
| atgccctccc ctgccagctc tgggcttcag agataaggca ttttccttgt gcagcctta | 2220 |
| cctggcaatc ctaatttggt tttaagactc cctgtgaaat gctttccgca ccttaacccc | 2280 |
| agtgagcgtg aaaagaaag ttaataaact ataatacatg gaagcaagaa aaaaaaaaa | 2340 |

<210> SEQ ID NO 30
<211> LENGTH: 821
<212> TYPE: DNA
<213> ORGANISM: Homo sapiens
<220> FEATURE:
<221> NAME/KEY: misc_feature
<223> OTHER INFORMATION: Incyte ID No: 5497787CB1

<400> SEQUENCE: 30

| | |
|---|---|
| gccgtcgccg ccatttcaag accgtactag gtagatggtc aattagagtt cccagggttt | 60 |
| gaagcctgta actgctgccg ccgctcaagc cctccagagc attgctacgg ctgctgccct | 120 |
| tgtactacta cctccaaata cgttcttgct ggtagtggcg gcagcaggac caattacctc | 180 |
| ttttttgctc tccctcgaga agctccagat ggcgtcttcc gtgggcaacg tggccgacag | 240 |
| cacagaacca acgaaacgta tgctttcctt ccaagggtta gctgagttgg cacatcgaga | 300 |
| atatcaggca ggagattttg aggcagctga gacactgc atgcagctct ggagacaaga | 360 |
| gccagacaat actggtgtgc ttttattact ttcatctata cacttccagt gtcgaaggct | 420 |
| ggacagatct gctcactta gcactctggc aattaaacag aaccccttc tggcagaagc | 480 |
| ttattcgaat ttggggaatg tgtacaagga agagggcag ttgcaggagg caattgagca | 540 |
| ttatcgacat gcattgcgtc tcaaacctga tttcatcgat ggttatatta acctggcagc | 600 |
| cgccttggta gcagcgggtg acatggaagg ggcagtacaa gcttacgtct ctgctcttca | 660 |

-continued

```
gtacaatcct gatttgtact gtgttcgcag tgacctgggg aacctgctca aagccctggg      720
tcgcttggaa gaagccaagg taggtgtttg atagaacaca tttaaacatc agtattatga      780
aaacttgtac tttttgccaa gtcttcaact cttcattgag c                          821
```

<210> SEQ ID NO 31
<211> LENGTH: 478
<212> TYPE: PRT
<213> ORGANISM: Homo sapiens
<300> PUBLICATION INFORMATION:
<308> DATABASE ACCESSION NUMBER: g2443814

<400> SEQUENCE: 31

```
Met Met Glu Gly Asn Gly Asn Gly His Glu His Cys Ser Asp Cys
 1               5                  10                  15

Glu Asn Glu Glu Asp Asn Ser Tyr Asn Arg Gly Gly Leu Ser Pro
                20                  25                  30

Ala Asn Asp Thr Gly Ala Lys Lys Lys Lys Gln Lys Lys
                35                  40                  45

Lys Lys Glu Lys Gly Ser Glu Thr Asp Ser Ala Gln Asp Gln Pro
                50                  55                  60

Val Lys Met Asn Ser Leu Pro Ala Glu Arg Ile Gln Glu Ile Gln
                65                  70                  75

Lys Ala Ile Glu Leu Phe Ser Val Gly Gln Gly Pro Ala Lys Thr
                80                  85                  90

Met Glu Glu Ala Ser Lys Arg Ser Tyr Gln Phe Trp Asp Thr Gln
                95                 100                 105

Pro Val Pro Lys Leu Gly Glu Val Val Asn Thr His Gly Pro Val
               110                 115                 120

Glu Pro Asp Lys Asp Asn Ile Arg Gln Glu Pro Tyr Thr Leu Pro
               125                 130                 135

Gln Gly Phe Thr Trp Asp Ala Leu Asp Leu Gly Asp Arg Gly Val
               140                 145                 150

Leu Lys Glu Leu Tyr Thr Leu Leu Asn Glu Asn Tyr Val Glu Asp
               155                 160                 165

Asp Asp Asn Met Phe Arg Phe Asp Tyr Ser Pro Glu Phe Leu Leu
               170                 175                 180

Trp Ala Leu Arg Pro Pro Gly Trp Leu Pro Gln Trp His Cys Gly
               185                 190                 195

Val Arg Val Val Ser Ser Arg Lys Leu Val Gly Phe Ile Ser Ala
               200                 205                 210

Ile Pro Ala Asn Ile His Ile Tyr Asp Thr Glu Lys Lys Met Val
               215                 220                 225

Glu Ile Asn Phe Leu Cys Val His Lys Lys Leu Arg Ser Lys Arg
               230                 235                 240

Val Ala Pro Val Leu Ile Arg Glu Ile Thr Arg Arg Val His Leu
               245                 250                 255

Glu Gly Ile Phe Gln Ala Val Tyr Thr Ala Gly Val Val Leu Pro
               260                 265                 270

Lys Pro Val Gly Thr Cys Arg Tyr Trp His Arg Ser Leu Asn Pro
               275                 280                 285

Arg Lys Leu Ile Glu Val Lys Phe Ser His Leu Ser Arg Asn Met
               290                 295                 300

Thr Met Gln Arg Thr Met Lys Leu Tyr Arg Leu Pro Glu Thr Pro
               305                 310                 315
```

```
Lys Thr Ala Gly Leu Arg Pro Met Glu Thr Lys Asp Ile Pro Val
                320                 325                 330

Val His Gln Leu Leu Thr Arg Tyr Leu Lys Gln Phe His Leu Thr
                335                 340                 345

Pro Val Met Ser Gln Glu Val Glu His Trp Phe Tyr Pro Gln
                350                 355                 360

Glu Asn Ile Ile Asp Thr Phe Val Glu Asn Ala Asn Gly Glu
                365                 370                 375

Val Thr Asp Phe Leu Ser Phe Tyr Thr Leu Pro Ser Thr Ile Met
                380                 385                 390

Asn His Pro Thr His Lys Ser Leu Lys Ala Ala Tyr Ser Phe Tyr
                395                 400                 405

Asn Val His Thr Gln Thr Pro Leu Leu Asp Leu Met Ser Asp Ala
                410                 415                 420

Leu Val Leu Ala Lys Met Lys Gly Phe Asp Val Phe Asn Ala Leu
                425                 430                 435

Asp Leu Met Glu Asn Lys Thr Phe Leu Glu Lys Leu Lys Phe Gly
                440                 445                 450

Ile Gly Asp Gly Asn Leu Gln Tyr Tyr Leu Tyr Asn Trp Lys Cys
                455                 460                 465

Pro Ser Met Gly Ala Glu Lys Val Gly Leu Val Leu Gln
                470                 475

<210> SEQ ID NO 32
<211> LENGTH: 361
<212> TYPE: PRT
<213> ORGANISM: Arabidopsis thaliana
<300> PUBLICATION INFORMATION:
<308> DATABASE ACCESSION NUMBER: g2642159

<400> SEQUENCE: 32

Met Lys Ala Leu Ile Leu Val Gly Gly Phe Gly Thr Arg Leu Arg
  1               5                  10                  15

Pro Leu Thr Leu Ser Phe Pro Lys Pro Leu Val Asp Phe Ala Asn
                 20                  25                  30

Lys Pro Met Ile Leu His Gln Ile Glu Ala Leu Lys Ala Val Gly
                 35                  40                  45

Val Asp Glu Val Val Leu Ala Ile Asn Tyr Gln Pro Glu Val Met
                 50                  55                  60

Leu Asn Phe Leu Lys Asp Phe Glu Thr Lys Leu Glu Ile Lys Ile
                 65                  70                  75

Thr Cys Ser Gln Glu Thr Glu Pro Leu Gly Thr Ala Gly Pro Leu
                 80                  85                  90

Ala Leu Ala Arg Asp Lys Leu Leu Asp Gly Ser Gly Glu Pro Phe
                 95                 100                 105

Phe Val Leu Asn Ser Asp Val Ile Ser Glu Tyr Pro Leu Lys Glu
                110                 115                 120

Met Leu Glu Phe His Lys Ser His Gly Gly Glu Ala Ser Ile Met
                125                 130                 135

Val Thr Lys Val Asp Glu Pro Ser Lys Tyr Gly Val Val Met
                140                 145                 150

Glu Glu Ser Thr Gly Arg Val Glu Lys Phe Val Glu Lys Pro Lys
                155                 160                 165

Leu Tyr Val Gly Asn Lys Ile Asn Ala Gly Ile Tyr Leu Leu Asn
                170                 175                 180
```

```
Pro Ser Val Leu Asp Lys Ile Glu Leu Arg Pro Thr Ser Ile Glu
                185                 190                 195

Lys Glu Thr Phe Pro Lys Ile Ala Ala Gln Gly Leu Tyr Ala
                200                 205                 210

Met Val Leu Pro Gly Phe Trp Met Asp Ile Gly Gln Pro Arg Asp
                215                 220                 225

Tyr Ile Thr Gly Leu Arg Leu Tyr Leu Asp Ser Leu Arg Lys Lys
                230                 235                 240

Ser Pro Ala Lys Leu Thr Ser Gly Pro His Ile Val Gly Asn Val
                245                 250                 255

Leu Val Asp Glu Thr Ala Thr Ile Gly Glu Gly Cys Leu Ile Gly
                260                 265                 270

Pro Asp Val Ala Ile Gly Pro Gly Cys Ile Val Glu Ser Gly Val
                275                 280                 285

Arg Leu Ser Arg Cys Thr Val Met Arg Gly Val Arg Ile Lys Lys
                290                 295                 300

His Ala Cys Ile Ser Ser Ile Ile Gly Trp His Ser Thr Val
                305                 310                 315

Gly Gln Trp Ala Arg Ile Glu Asn Met Thr Ile Leu Gly Glu Asp
                320                 325                 330

Val His Val Ser Asp Glu Ile Tyr Ser Asn Gly Val Val Leu
                335                 340                 345

Pro His Lys Glu Ile Lys Ser Asn Ile Leu Lys Pro Glu Ile Val
                350                 355                 360

Met

<210> SEQ ID NO 33
<211> LENGTH: 373
<212> TYPE: PRT
<213> ORGANISM: Caenorhabditis elegans
<300> PUBLICATION INFORMATION:
<308> DATABASE ACCESSION NUMBER: g2804432

<400> SEQUENCE: 33

Met Val Val Ser Pro Leu Pro Ser Met Lys Ala Leu Ile Leu Val
 1               5                  10                  15

Gly Gly Tyr Gly Thr Arg Leu Arg Pro Leu Thr Leu Thr Gln Pro
                20                  25                  30

Lys Pro Leu Val Glu Phe Ala Asn Lys Pro Met Met Leu His Gln
                35                  40                  45

Met Glu Ala Leu Ala Glu Val Gly Val Asp Thr Val Leu Ala
                50                  55                  60

Val Ser Tyr Arg Ala Glu Gln Leu Glu Gln Glu Met Thr Val His
                65                  70                  75

Ala Asp Arg Leu Gly Val Lys Leu Ile Phe Ser Leu Glu Glu Glu
                80                  85                  90

Pro Leu Gly Thr Ala Gly Pro Leu Ala Leu Ala Arg Lys His Leu
                95                  100                 105

Glu Gly Asp Ala Pro Phe Phe Val Leu Asn Ser Asp Val Ile Cys
                110                 115                 120

Asp Phe Pro Phe Lys Gln Met Val Glu Phe His Lys Asn His Gly
                125                 130                 135

Lys Glu Gly Thr Ile Ala Val Thr Lys Val Glu Glu Pro Ser Lys
                140                 145                 150

Tyr Gly Val Val Phe Asp Gln Asp Lys Gly Lys Ile Asp Asp
```

-continued

```
                        155                 160                 165
Phe Val Glu Lys Pro Gln Glu Tyr Val Gly Asn Lys Ile Asn Ala
                170                 175                 180
Gly Leu Tyr Ile Phe Ser Ser Lys Ile Leu Asp Arg Ile Pro Leu
                185                 190                 195
Lys Pro Thr Ser Ile Glu Lys Glu Ile Phe Pro Glu Met Ala Phe
                200                 205                 210
Ser Gly Asn Leu Tyr Ala Phe Val Leu Pro Gly Phe Trp Met Asp
                215                 220                 225
Val Gly Gln Pro Lys Asp Phe Leu Lys Gly Met Ser Leu Phe Leu
                230                 235                 240
Asn His Cys His Thr Thr Lys Ser Asp Lys Leu Glu Thr Gly Ser
                245                 250                 255
Asn Ile His Pro Thr Ala Thr Ile Arg Gly Asn Val Met Val Asp
                260                 265                 270
Pro Ser Ala Thr Val Gly Glu Asn Cys Val Ile Gly Pro Asp Val
                275                 280                 285
Val Ile Gly Pro Arg Val Lys Ile Glu Gly Gly Val Arg Ile Leu
                290                 295                 300
His Ser Thr Ile Leu Ser Asp Ser Ser Ile Gly Asn Tyr Ser Trp
                305                 310                 315
Val Ser Gly Ser Ile Val Gly Arg Lys Cys His Ile Gly Ser Trp
                320                 325                 330
Val Arg Ile Glu Asn Ile Cys Val Ile Gly Asp Asp Val Val Val
                335                 340                 345
Lys Asp Glu Leu Tyr Leu Asn Gly Ala Ser Val Leu Pro His Lys
                350                 355                 360
Ser Ile Ala Val Asn Val Pro Ser Lys Asp Ile Ile Met
                365                 370
```